(12) United States Patent
Burgess et al.

(10) Patent No.: US 11,541,194 B2
(45) Date of Patent: Jan. 3, 2023

(54) FLOW PATH SENSING FOR FLOW THERAPY APPARATUS

(71) Applicant: Fisher & Paykel Healthcare Limited, Auckland (NZ)

(72) Inventors: Russel William Burgess, Auckland (NZ); Dean Antony Barker, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 483 days.

(21) Appl. No.: 16/603,720

(22) PCT Filed: Apr. 13, 2018

(86) PCT No.: PCT/NZ2018/050052
§ 371 (c)(1),
(2) Date: Oct. 8, 2019

(87) PCT Pub. No.: WO2018/190732
PCT Pub. Date: Oct. 18, 2018

(65) Prior Publication Data
US 2020/0054847 A1 Feb. 20, 2020

Related U.S. Application Data

(60) Provisional application No. 62/516,579, filed on Jun. 7, 2017, provisional application No. 62/485,614, filed on Apr. 14, 2017.

(51) Int. Cl.
*A61M 16/00* (2006.01)
*A61M 16/10* (2006.01)

(52) U.S. Cl.
CPC ...... *A61M 16/024* (2017.08); *A61M 16/0003* (2014.02); *A61M 16/0066* (2013.01);
(Continued)

(58) Field of Classification Search
CPC ............ A61M 16/024; A61M 16/0003; A61M 16/1005; A61M 16/0066;
(Continued)

(56) References Cited

U.S. PATENT DOCUMENTS 5,099,837 A * 3/1992 Russel, Sr. ........ A61M 16/0677
128/204.26
8,545,402 B2 * 10/2013 Hafezi ................ H01M 50/138
424/464
(Continued)

FOREIGN PATENT DOCUMENTS

EP 3146897 A1 3/2017
WO WO-2015101788 A1 * 7/2015 ............. G01N 29/04
(Continued)

OTHER PUBLICATIONS

International Search Report in corresponding International Patent Application No. PCT/NZ2018/050052, dated Oct. 12, 2018, in 9 pages.
(Continued)

*Primary Examiner* — Annette Dixon
(74) *Attorney, Agent, or Firm* — Knobbe, Martens, Olson & Bear, LLP

(57) ABSTRACT

A respiratory flow therapy apparatus including a sensor module can measure a flow rate of gases or gases concentration provided to a patient. The sensor module can be located after a blower and/or mixer. The sensor module can include at least an ultrasonic transmitter, a receiver, a temperature sensor, a pressure sensor, a humidity sensor and/or a flow rate sensor. The receivers can be immersed in the gases flow path. The receivers can cancel delays in the transmitters and improve accuracy of measurements of characteristics of the gases flow. The receivers can allow for detection of a fault condition in a blower motor of the apparatus.

23 Claims, 33 Drawing Sheets

(52) U.S. Cl.
CPC . *A61M 16/1005* (2014.02); *A61M 2205/3334* (2013.01); *A61M 2205/3372* (2013.01); *A61M 2205/3375* (2013.01); *A61M 2205/3592* (2013.01); *A61M 2205/70* (2013.01)

(58) Field of Classification Search
CPC .. A61M 2205/3334; A61M 2205/3372; A61M 2205/3375; A61M 2205/3592; A61M 2205/70; A61M 16/0051; A61M 16/0057; A61M 16/0063; A61M 16/0069; A61M 16/026; A61M 2205/42; G01N 2291/011; G01N 2291/012; G01N 2291/0215; G01N 2291/02809; G01N 2291/02836; G01N 2291/104; G01N 29/024; G01N 29/326; G01N 29/348
See application file for complete search history.

(56) References Cited

U.S. PATENT DOCUMENTS

| | | | | |
|---|---|---|---|---|
| 2002/0062681 | A1* | 5/2002 | Livingston | G01N 29/326 73/24.01 |
| 2008/0110459 | A1* | 5/2008 | Farbarik | A61M 16/026 128/204.18 |
| 2008/0208056 | A1 | 8/2008 | Kuhn et al. | |
| 2009/0266359 | A1* | 10/2009 | Flint | G10K 11/17857 128/204.18 |
| 2010/0152580 | A1 | 6/2010 | Ganshorn | |
| 2011/0313689 | A1 | 12/2011 | Holley et al. | |
| 2012/0055483 | A1 | 3/2012 | Wilkinson et al. | |
| 2012/0312302 | A1* | 12/2012 | Cardelius | A61M 16/104 128/203.14 |
| 2015/0059745 | A1* | 3/2015 | Barker | A61M 16/0066 128/203.14 |
| 2016/0354040 | A1* | 12/2016 | Aarts | A61B 5/4836 |

FOREIGN PATENT DOCUMENTS

| | | |
|---|---|---|
| WO | WO 2016/157105 A1 | 10/2016 |
| WO | WO 2018/190732 A2 | 10/2018 |

OTHER PUBLICATIONS

Written Opinion in corresponding International Patent Application No. PCT/NZ2018/050052, dated Oct. 12, 2018, in 14 pages.
International Preliminary Report on Patentability in corresponding International Patent Application No. PCT/NZ2018/050052, dated Oct. 15, 2019, in 15 pages.

* cited by examiner

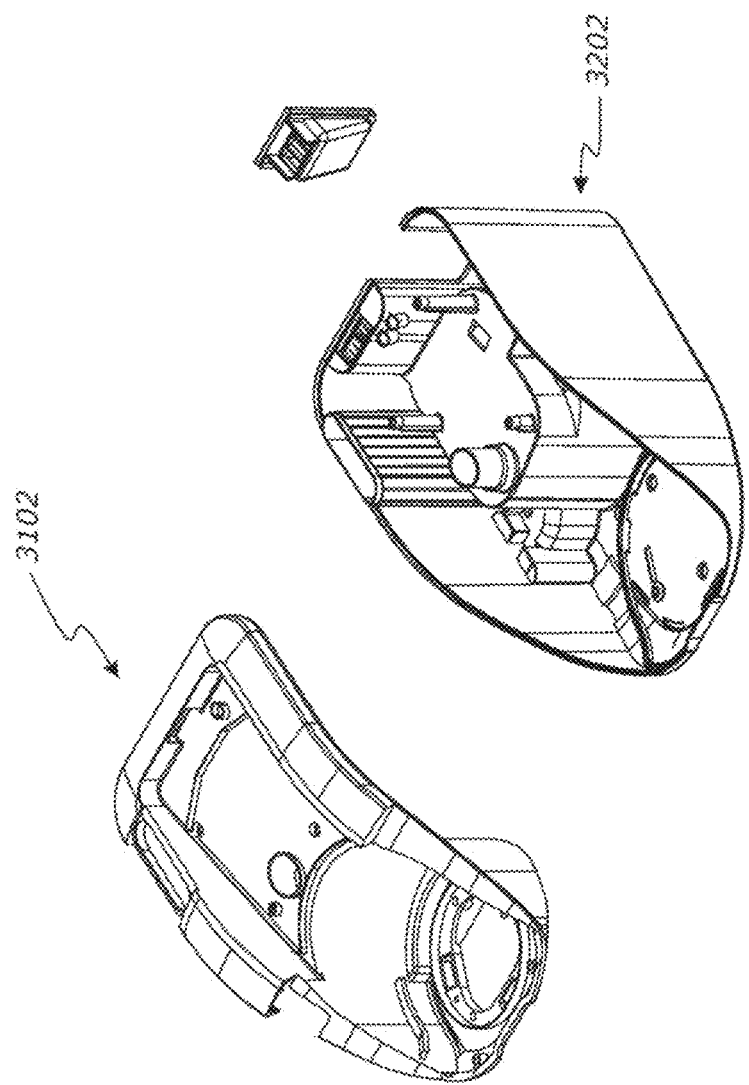
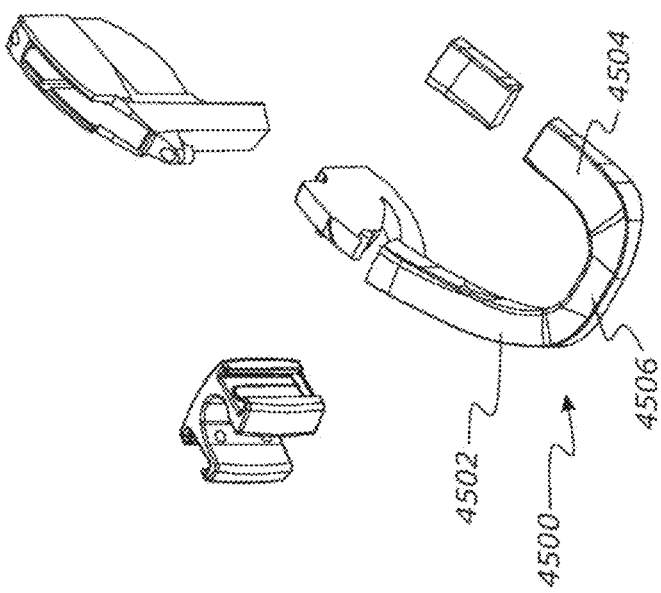
FIG. 18B

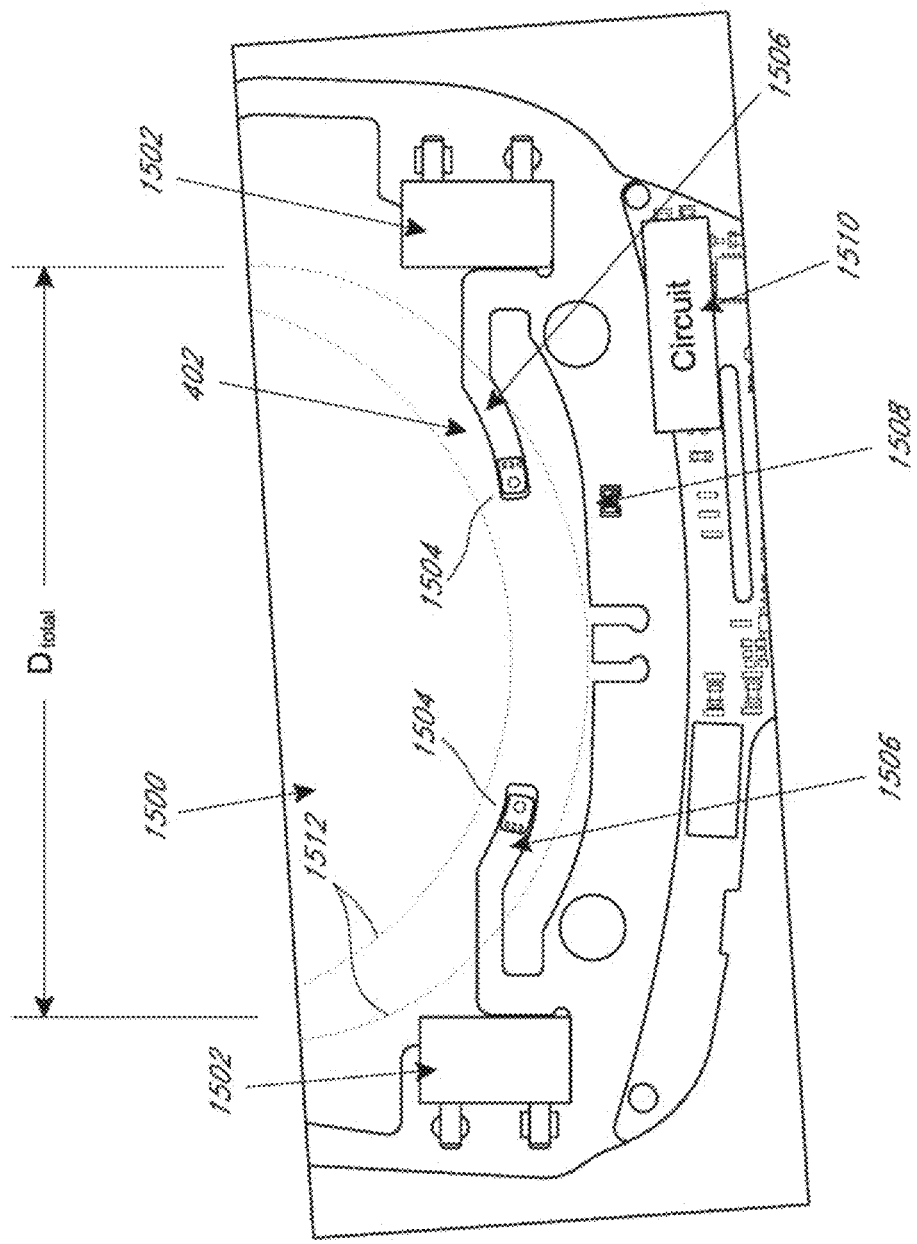

FLOW PATH SENSING FOR FLOW THERAPY APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a U.S. National Phase of PCT International Application No. PCT/NZ2018/050052, filed Apr. 13, 2018 and published as WO 2018/190732, which claims priority from U.S. Provisional Application No. 62/485,614, filed Apr. 14, 2017 and U.S. Provisional Application No. 62/516,579, filed Jun. 7, 2017, the entire contents of which are hereby incorporated by reference.

FIELD OF THE DISCLOSURE

The present disclosure relates to methods and systems for flow path sensing in a flow therapy apparatus for delivering gas to patients. In particular, the present disclosure relates to flow path sensing using acoustic sensors including acoustic transmitters and/or receivers.

BACKGROUND

Breathing assistance apparatuses are used in various environments such as hospital, medical facility, residential care, or home environments to deliver a flow of gas to users or patients. A breathing assistance apparatus, or a flow therapy apparatus, may be used to deliver supplementary oxygen with the flow of gas, and/or a humidification apparatus to deliver heated and humidified gases. A flow therapy apparatus may allow adjustment and control over characteristics of the gases flow, including flow rate, temperature, gases concentration, humidity, pressure, etc. Sensors, such as heated temperature sensing elements and/or pressure sensors, are used to measure these characteristics of the gases flow.

SUMMARY

Ultrasonic sensors including ultrasonic transmitters and/or receivers can be used to measure a time of flight of acoustic signals to determine gas velocity and/or composition, which can be used in flow therapy apparatuses, such as described in International Application No. PCT/NZ2016/050193, filed Dec. 2, 2016 and entitled "FLOW PATH SENSING FOR FLOW THERAPY APPARATUS," the disclosure of which is incorporated herein in its entirety. In one ultrasonic sensor (including ultrasonic transmitters and/or receivers) topology, a driver causes a first sensor, such as an ultrasonic transducer, to produce an ultrasonic pulse in a first direction. A second sensor, such as a second ultrasonic transducer, receives this pulse and provides a measurement of the time of flight of the pulse between the first and second ultrasonic transducers. Using this time of flight measurement, the speed of sound of the gases flow between the ultrasonic transducers can be calculated by a hardware processor or controller of the flow therapy apparatus. Characteristics of the gases flow, such as gases concentration, can then also be determined by the hardware processor using the time of flight measurement. The second sensor can transmit and the first sensor can receive a pulse in a second direction opposite the first direction to provide a second measurement of the time of flight, allowing additional characteristics of the gases flow, such as a flow rate or velocity, to be determined.

Ultrasonic sensor (including ultrasonic transmitters and/or receivers) topologies that use the same sensor, such as a transducer, to both transmit and receive the ultrasonic signal have a number of drawbacks addressed by the present disclosure. Examples of drawbacks can include, but are not limited to, transducer delays, temperature drift, and dead space. Specifically, the dual function, which allows the transducers to be used both as transmitters and receivers, may limit the type of transducers in these topologies to piezoelectric transducers, which are resistant to sources of acoustic noise because they resonate at a specific frequency and are thus a good candidate for flow path sensing. However, this resonance also causes the transducers to have large delays as the resonance introduces phase delays to the response, and it takes time for the piezoelectric transducers to "ring-up" when transmitting or receiving an acoustic pulse. The combined response of a transmitter and receiver also means the signal must pass through both the transmitting and receiving piezoelectric transducers. Because both transducers are resonant, the combined response can have a phase delay and transient response sensitive to the resonant frequencies. This can possibly produce non-sinusoidal waveforms and phenomena such as beat. As these effects may appear in the waveform used to measure the time of flight, any shift in the resonant frequencies (for example, due to temperature change) can affect the accuracy of the transducer. The size of piezoelectric transducers also makes it difficult to mount them directly in the gases flow path of a flow therapy apparatus in the present disclosure. If the transducers are located within the gases flow, their temperature generally equilibrates to approximately the temperature of the gases flow and measurement adjustments can be made accordingly. When the transducers are located outside the gases flow path, temperature drift of the transducers can potentially introduce errors into the system. Furthermore, there can also be a "dead space" at either end of the ultrasonic path, which is the path that an ultrasonic pulse travels. The dead spaces are the part of the ultrasonic path where there is no gases flow. These spaces need to be accounted for in the calculations. Dead space regions may not be clearly defined, but are small and can be approximated. One method of taking into the account dead space regions in the calculations can be to approximate the dead space to $\frac{1}{2}D_o$ on each end of a distance D where there is gases flow. The measured times of flight in both directions then become $$t_1 = \frac{D_O}{c} + \frac{D}{c+v} \text{ and } t_2 = \frac{D_O}{c} + \frac{D}{c-v},$$

which can be rearranged to provide a solution for the speed of sound c as $$c = \frac{(t_1+t_2)(2D_0+D) + \sqrt{(t_1+t_2)^2(2D_0+D)^2 - 16t_1t_2D_0(D_0+D)}}{4t_1t_2},$$

and a solution for the velocity of the gases flow v as $$v = c\frac{D}{2}\left(\frac{1}{ct_1 - D_0} - \frac{1}{ct_2 - D_0}\right).$$

Based on an assumption that the speed of sound c will be significantly higher than the velocity of the gases flow v, it can be approximated that $c^2 \gg v^2$. Therefore, the expressions above can be simplified to $$c \approx \frac{D + D_0}{2}\left(\frac{1}{t_1} + \frac{1}{t_2}\right) \text{ and } v \approx \frac{(D_0 + D)^2}{2D}\left(\frac{1}{t_1} - \frac{1}{t_2}\right).$$

A volumetric flow rate Q can be obtained by multiplying the velocity v by an effective cross sectional area A: Q=vA. If the flow forms an angle θ with the acoustic path, the volumetric flow rate can be expressed as $$q = \frac{v}{\cos\theta}A.$$

The expressions for c and v can also be reduced to different forms based on different assumptions.

The present disclosure provides for one or more relatively small acoustic receivers or microphones in or to the side of the gases flow path. Appropriate use of this configuration allows for transducer delays to be largely cancelled out. Decoupling the acoustic transmitter and receiver functions can allow the system to use smaller acoustic transmitters and receivers than the bulky piezoelectric transducers. Immersing the acoustic receivers within or to the side of the gases flow path can advantageously allow the acoustic receivers to be at approximately the same temperature as a measured temperature of the gases in the flow path, thereby increasing the accuracy of the calculations and/or measurement. Moreover, acoustic receivers such as microphones have much smaller delays than piezoelectric transducers as there is no resonance in the microphones.

However, using microphones as acoustic receivers has its own challenges, many of which are discussed below with provided solutions. As described above, the microphones are generally not resonant and therefore can pick up any sources of acoustic noise. Sources of acoustic noise out of the ultrasonic frequency band that can be picked up by the microphones include but are not limited to the rushing of air past the sensor port, noise from the blower, and the like. This alone can produce noise as large as the ultrasonic signal. As will be described in greater detail below, the acoustic noise can be reduced and/or removed at least by, for example, a high-pass filter to filter out acoustic noise that is below the ultrasonic frequency range (which can be the acoustic signal of interest), edge detection, cross-correlation, and/or any combinations thereof.

There are also challenges in positioning the acoustic sensors including acoustic transmitters and/or receivers in a compact system to obtain a distortion-free acoustic signal, such as a distortion-free ultrasonic signal. In a large system with a long flow path, plane waves can be used to allow acoustic sensors including acoustic transmitters and/or receivers positioned outside the flow path to be used to receive clear signals, because the characteristics of the wave do not change across the width of the flow path. However, when the acoustic sensors including acoustic transmitters and/or receivers must work in the near field because of the size of the measuring system, such as in a thin, short measurement section, and with limitations in the frequency range of the acoustic signal, the signal quality depends on where the measuring of the signal takes place or where the sensors are positioned. The systems described herein can be a compact system with a short flow path. The short distance of the flow path can make it difficult to have a plane wave, as the wavelength of the signal can be of the same order as the width of the flow path. As a result, although both in-path and out-of-path acoustic receivers can be used in the system, under some circumstances, in-path acoustic receivers may be more effective than out-of-path acoustic receivers for the purpose of determining characteristics of the gases flow in the systems described herein. When out-of-path acoustic receivers are used, the acoustic receivers can be placed in locations where there is less signal distortion due to the acoustic receivers being out of the gases flow path. As described above, there may also be concern with out-of-path acoustic receivers not being at approximately the same temperature as the gases flow. However, the temperature difference, if any, between the acoustic receiver(s) and the gases flow, can be compensated for using mathematical equations and acoustic receiver temperature determinations by a temperature sensor. In addition, when two acoustic receivers are placed between two acoustic transmitters, as will be described below, effects of the temperature difference on the acoustic signal can be canceled. Furthermore, another reason for not using plane waves in the systems described herein is that the acoustic signals would fall outside the ultrasonic frequency range and fall into an audible range. As described above, it can be desirable to use acoustic signals that are in the ultrasonic frequency range, for example to allow use of a high-pass filter. It can also be desirable to avoid use of acoustic signals in the audible range, which can be uncomfortable for the user. These and other solutions that enable the present disclosure are provided below.

The present disclosure provides a flow therapy or respiratory system having acoustic sensor (including acoustic transmitters and/or receivers) topologies that overcome one or more of the problems described herein. The present disclosure provides acoustic sensor (including acoustic transmitters and/or receivers) topologies that do not require the use of plane waves. The acoustic sensor (including acoustic transmitters and/or receivers) topologies described herein can mitigate or cancel sensor delays, allow the acoustic receivers to be mounted directly in the gases flow path to get a clear signal and to have approximately the same temperature as a measured temperature of the gases in the flow path, and/or are minimally affected by acoustic noises. The acoustic sensor (including acoustic transmitters and/or receivers) topologies described herein can also allow acoustic receivers to be mounted in locations outside the gases flow path to get less distorted signals.

It is an object of one or more of the disclosed embodiments to provide a respiratory assistance system that addresses one or more of the issues provided above, or that will at least provide the public or a medical professional with a useful choice.

A respiratory assistance system for providing a flow of gases to a patient can comprise a first acoustic transmitter positioned at a first position in or near a gases flow path, the first acoustic transmitter configured to transmit a first acoustic signal; a second acoustic transmitter positioned at a second position in or near the gases flow path, the second acoustic transmitter configured to transmit a second acoustic signal; and one or more acoustic receivers positioned between the first position and the second position, the one or more acoustic receivers configured to receive the first and the second transmitted acoustic signals, wherein the acoustic transmitters and the one or more acoustic receivers are in electrical communication with a hardware processor configured to determine one or more characteristics of the gases flow based on the received first and second acoustic signals. The one or more acoustic receivers can comprise two acoustic receivers. One acoustic receiver can be downstream of another acoustic receiver. The first and second acoustic transmitters can face each other along the gases flow path so that acoustic signals produced by each acoustic transmitter are directed at the other acoustic transmitter. The first and second acoustic transmitters can be a matched pair of acoustic transmitters. The one or more acoustic receivers can be microphones. The one or more acoustic receivers can be located between and spaced from the first and second acoustic transmitters at a sufficient distance so as to mitigate near-field effects. A distance between one of the first and second acoustic transmitters and a nearest one of the one or more acoustic receivers can be between about 10 mm and about 40 mm, or can be about 20 mm. The first and second acoustic transmitters can be two acoustic transducers configured to act as both acoustic transmitters and receivers. The first acoustic transmitter can be configured to transmit acoustic signals toward the second position and the second acoustic transmitter can be configured to transmit acoustic signals toward the first position. The one or more characteristics of the gases flow can comprise a gases concentration. The gases concentration can comprise an oxygen concentration, a carbon dioxide concentration, a heliox concentration, or a concentration of any other desired gases in the flow path. The one or more characteristics of the gases flow can comprise a gases flow rate. The one or more acoustic receivers can be located within the gases flow path. The hardware processor can be configured to estimate a temperature of the one or more acoustic receivers to be at the same temperature as a measured temperature of gases in the flow path. The system can further comprise one or more of a temperature sensor, a pressure sensor, a humidity sensor, and/or a flow rate sensor. The flow rate sensor can be a heated temperature sensing element. The hardware processor can be configured to be in communication with the one or more of the temperature sensor, the pressure sensor, the humidity sensor, and/or the flow rate sensor and to use outputs of the one or more of the temperature sensor, the pressure sensor, the humidity sensor, and/or the flow rate sensor to determine the one or more characteristics of the gases flow. The processor can be configured to compensate for temperature difference between the one or more acoustic receivers and the gases flow based at least in part on measurements by the temperature sensor when determining the one or more characteristics of the gases flow. The processor can be configured to compute or adjust a calibration parameter of the acoustic transmitters and/or the one or more acoustic receivers based on a flow rate measured by the flow rate sensor. The gases flow path between the first position and the second position can comprise a curved flow path. The gases flow path between the first position and the second position can comprise a portion of the flow path having a straight flow path. The first and second acoustic transmitters can be ultrasonic transmitters. The system can further comprise a blower. The blower can be configured to provide a high flow therapy to a patient. The first and second acoustic transmitters and the one or more acoustic receivers can be comprised within a removable sensor module. The blower, the first and second acoustic transmitters, and the one or more acoustic receivers can be comprised within a removable blower and sensor module. The removable sensor module or blower and sensor module can be configured for insertion into a housing of the respiratory system. The blower, the first and second acoustic transmitters, and the one or more acoustic receivers can be comprised within a non-removable sensor module or blower and sensor module. The sensor module or the blower and sensor module can comprise a sensing circuit board. The first and second acoustic transmitters and the one or more acoustic receivers can be located on the sensing circuit board. The system can further comprise a patient breathing conduit configured to be coupled to a gases flow outlet of the respiratory system on one end of the conduit and to a patient interface on another end of the conduit. The patient interface can be a nasal cannula a full face mask, a nasal mask, a tracheostomy interface, a nasal pillows mask, or an endotracheal tube. The patient breathing conduit can comprise a heater wire configured to heat gases passing through the conduit. The system can further comprise a humidification chamber configured to humidify the gases flow to a patient. The system can further comprise a display configured to display the one or more characteristics of the gases flow. The acoustic signal(s) can comprise an ultrasonic signal. The acoustic signal(s) can comprise acoustic noises from the blower. The hardware processor can be configured to determine from the acoustic signal received at the acoustic receivers a fault condition in a blower motor. The fault condition can be related or correlatable to motor speed. The hardware processor can be configured to analyze spectrally the acoustic signals received at the acoustic receivers to determine a frequency or range of frequencies above a predetermined threshold. The hardware processor can be configured to determine a fault condition based on an amplitude, or a relationship of amplitudes between different fault conditions, or a threshold amplitude of the acoustic signals at a predetermined frequency or range of frequencies. The motor speed can be varied during a fault condition detection operation and the hardware processor can be configured to determine a fault condition based on a corresponding varying of a portion of the acoustic signals caused by or relating to the fault condition.

A respiratory assistance system for providing a flow of gases to a patient can comprise an acoustic source configured to generate at least a first acoustic signal; and at least two acoustic receivers configured to each receive the first acoustic signal, the at least two acoustic receivers in electrical communication with a hardware processor configured to determine a time of flight of the acoustic signal by determining a difference of time between a receipt of the at least first acoustic signal by a first one of the at least two acoustic receivers and a receipt of the at least first acoustic signal by a second one of the at least two acoustic receivers. The system can be configured to generate measurements of at least one characteristic of a gases flow of the system based on the difference of time between the receipt of the at least first acoustic signal by the first one of the at least two acoustic receivers and the second one of the at least two acoustic receivers. The system can be configured to generate measurements of at least one characteristic of a gases flow of the system based on a time taken to receive the at least first acoustic signal by one of the at least two acoustic receivers. The at least one characteristic of the gases flow can comprise a flow rate or a gases concentration. The gases concentration can comprise an oxygen concentration, a carbon dioxide concentration, a heliox concentration, or a concentration of any other desired gases in the flow path. The at least two acoustic receivers can be microphones. The acoustic source can be an acoustic transmitter. The acoustic source can comprise first and second acoustic transducers. The first and second acoustic transducers can be a matched pair of ultrasonic transducers. The acoustic source can comprise first and second ultrasonic transducers. Each of the first and second acoustic transducers can be configured to both transmit and receive acoustic signals such that the acoustic signals are transmitted in both upstream and downstream directions along an acoustic path between the first and second acoustic transducers. The at least two acoustic receivers can be positioned between the first and second acoustic transducers. The hardware processor can be configured to cancel out errors in the time of flight determinations due to delay of the first and second acoustic transducers. The first and second acoustic transducers can be located substantially at or near each end of a measurement portion of a gases flow path. The at least two acoustic receivers can be located within the measurement portion of the gases flow path. The system can comprise one or more of a pressure sensor, a humidity sensor, and/or a flow rate sensor. The flow rate sensor can be a heated temperature sensing element. The hardware processor can be configured to use outputs of the one or more of the pressure sensor, the humidity sensor, or the flow rate sensor for the calculation of a characteristic of the gases flow. The processor can be configured to compensate for temperature difference between the at least two acoustic receivers and the gases flow based at least in part on measurements by the temperature sensor when determining the one or more characteristics of the gases flow. The processor can be configured to compute or adjust a calibration parameter of the acoustic source and/or the at least two acoustic receivers based on a flow rate measured by the flow rate sensor. The at least two acoustic receivers can be located on a central axis of a gases flow path. The hardware processor can be configured to estimate a temperature of the at least two acoustic receivers to be at the same temperature as a measured temperature of gases in the flow path. The measurement portion of the gases flow path can comprise a curved flow path. The measurement portion of the gases flow path can comprise a portion of the flow path having a straight flow path. The at least two acoustic receivers can be located in the measurement portion of the gases flow path in a configuration which avoids dead space in a measurement region. The system can comprise a first distance defined between the first one of the at least two acoustic receivers and the acoustic source, and a second distance defined between the second one of the at least two acoustic receivers and the acoustic source. The hardware processor can be configured to use a time of flight measurement taken along the first distance to provide an estimate of a time of flight. The hardware processor can be configured to use a time of flight measurement taken along the second distance to provide a more accurate assessment of the time of flight. The first distance can be shorter than the second distance. The time of flight measurements can be generated from between the first one of the at least two acoustic receivers and the acoustic source, between the second one of the at least two acoustic receivers and the acoustic source, between the first and second ones of the at least two acoustic receivers, between the first and second acoustic transducers, or a combination thereof in both directions along an acoustic path. The hardware processor can be configured to compare two or more of the time of flight measurements to determine accuracy of the two or more of the time of flight measurements. The hardware processor can be configured to use acoustic signals received by the at least two acoustic receivers to perform cross-correlation of the received acoustic signals. The hardware processor can be configured to use acoustic signals received at the at least two acoustic receivers to determine waveform deformation. The hardware processor can be configured to use acoustic signals received at the at least two acoustic receivers to detect a flow rate by determining time delay for the time of flight measurements. The first acoustic signal can comprise an ultrasonic signal. The system can further comprise a blower. The blower can be configured to provide a high flow therapy to a patient. The acoustic transmitter and the acoustic receiver can be comprised within a removable sensor module. The blower, the acoustic source, and the at least two acoustic receivers can be comprised within a removable blower and sensor module. The removable sensor module or blower and sensor module can be configured for insertion into a housing of the respiratory system. The blower, the acoustic source, and the at least two acoustic receivers can be comprised within a non-removable sensor module or blower and sensor module. The sensor module or the blower and sensor module can comprise a sensing circuit board. The acoustic source, and the at least two acoustic receivers can be located on the sensing circuit board. The system can further comprise a patient breathing conduit configured to be coupled to a gases flow outlet of the respiratory system on one end of the conduit and to a patient interface on another end of the conduit. The patient interface can be a nasal cannula, a full face mask, a nasal mask, a tracheostomy interface, a nasal pillows mask, or an endotracheal tube. The patient breathing conduit can comprise a heater wire configured to heat gases passing through the conduit. The system can further comprise a humidification chamber configured to humidify the gases flow to a patient. The system can further comprise a display configured to display the one or more characteristics of the gases flow. The acoustic signal(s) can comprise acoustic noises from the blower. The hardware processor can be configured to determine from the acoustic signal received at the acoustic receivers a fault condition in a blower motor. The fault condition can be related or correlatable to motor speed. The hardware processor can be configured to analyze spectrally the acoustic signal received at the acoustic receivers to determine a frequency or range of frequencies above a predetermined threshold. The hardware processor can be configured to determine a fault condition based on an amplitude, or a relationship of amplitudes between different fault conditions, or a threshold amplitude of the acoustic signal at a predetermined frequency or range of frequencies. The motor speed can be varied during a fault condition detection operation and the hardware processor can be configured to determine a fault condition based on a corresponding varying of a portion of the acoustic signal caused by or relating to the fault condition.

A respiratory assistance system for providing a flow of gases to a patient can comprise an acoustic transmitter configured to transmit an acoustic signal; a surface configured for echoing the acoustic signal; and an acoustic receiver configured to receive the echoed acoustic signal, the acoustic receiver being located within a gases flow path between the acoustic transmitter and the surface, the acoustic transmitter and receiver in electrical communication with a hardware processor configured to determine at least one characteristic of the gases flow based on the received acoustic signal. The acoustic receiver can be configured to receive the transmitted acoustic signal. The processor can be configured to determine at least one characteristic of the gases flow based on a difference between a time of flight measurement of the transmitted acoustic signal and a time of flight measurement of the echoed acoustic signal. The system can further comprise a second acoustic receiver located within a gases flow path between the acoustic transmitter and the surface. The second acoustic receiver can be configured to receive the transmitted acoustic signal. The at least two acoustic receivers can be located within a measurement portion of a gases flow path. The system can comprise one or more of a pressure sensor, a humidity sensor, and/or a flow rate sensor. The flow rate sensor can be a heated temperature sensing element. The hardware processor can be configured to use outputs of the one or more of the pressure sensor, the humidity sensor, or the flow rate sensor to determine at least one characteristic of the gases flow. The processor can be configured to compensate for temperature difference between the acoustic receiver and the gases flow based at least in part on measurements by the temperature sensor when determining the one or more characteristics of the gases flow. The processor can be configured to compute or adjust a calibration parameter of the acoustic transmitter and/or the acoustic receiver based on a flow rate measured by the flow rate sensor. The at least one characteristic of the gases flow can comprise one or more of a gases concentration or a flow rate. The gases concentration comprises an oxygen concentration, a carbon dioxide concentration, a heliox concentration, or a concentration of any other desired gases in the flow path. The acoustic receiver and/or the second acoustic receiver can be microphone(s). The acoustic transmitter can be an ultrasonic transmitter. The acoustic signal can comprise an ultrasonic signal. The measurement portion of the gases flow path can comprise a curved flow path. The measurement portion of the gases flow path can comprise a portion of the flow path having a straight flow path. The system can further comprise a blower. The blower can be configured to provide a high flow therapy to a patient. The acoustic transmitter and the acoustic receiver can be comprised within a removable sensor module. The blower, the acoustic transmitter and the acoustic receiver can be comprised within a removable blower and sensor module. The removable sensor module or blower and sensor module can be configured for insertion into a housing of the respiratory system. The blower, the acoustic transmitter, and the acoustic receiver are comprised within a non-removable sensor module or blower and sensor module. The sensor module or the blower and sensor module can comprise a sensing circuit board. The acoustic transmitter and the acoustic receiver can be located on the sensing circuit board. The system can further comprise a patient breathing conduit configured to be coupled to a gases flow outlet of the respiratory system on one end of the conduit and to a patient interface on another end of the conduit. The patient interface can be a nasal cannula, a full face mask, a nasal mask, a tracheostomy interface, a nasal pillows mask, or an endotracheal tube. The patient breathing conduit can comprise a heater wire configured to heat gases passing through the conduit. The system can further comprise a humidification chamber configured to humidify the gases flow to a patient. The system can further comprise a display configured to display the one or more characteristics of the gases flow. The acoustic signal(s) can comprise acoustic noises from the blower. The hardware processor can be configured to determine from the acoustic signal received at the acoustic receiver a fault condition in a blower motor. The fault condition can be related or correlatable to motor speed. The hardware processor can be configured to analyze spectrally the acoustic signal received at the acoustic receiver to determine a frequency or range of frequencies above a predetermined threshold. The hardware processor can be configured to determine a fault condition based on an amplitude, or a relationship of amplitudes between different fault conditions, or a threshold amplitude of the acoustic signal at a predetermined frequency or range of frequencies. The motor speed can be varied during a fault condition detection operation and the hardware processor can be configured to determine a fault condition based on a corresponding varying of a portion of the acoustic signal caused by or relating to the fault condition.

A respiratory assistance system for providing a flow of gases to a patient can comprise an acoustic transmitter configured to transmit an acoustic signal; a surface configured for echoing the acoustic signal; and at least two acoustic receivers configured to receive the echoed acoustic signal; the acoustic transmitter and at least two acoustic receivers in electrical communication with a hardware processor configured to determine at least one characteristic of the gases flow based on a calculated time of flight of the received acoustic signal. The at least two acoustic receivers can be located within a measurement portion of a gases flow path. The measurement portion of the gases flow path can comprise a curved flow path. The measurement portion of the gases flow path can comprise a portion of the flow path having a straight flow path. The acoustic transmitter can be an ultrasonic transmitter. The at least two acoustic receiver can be microphones. The acoustic signal can comprise an ultrasonic signal. The system can comprise one or more of a pressure sensor, a humidity sensor, and/or a flow rate sensor. The flow rate sensor can be a heated temperature sensing element. The hardware processor can be configured to use outputs of the one or more of the pressure sensor, the humidity sensor, or the flow rate sensor to determine at least one characteristic of the gases flow. The processor can be configured to compensate for temperature difference between the at least two acoustic receivers and the gases flow based at least in part on measurements by the temperature sensor when determining the one or more characteristics of the gases flow. The processor can be configured to compute or adjust a calibration parameter of the acoustic transmitter and/or the at least two acoustic receivers based on a flow rate measured by the flow rate sensor. The system can be configured to determine a plurality of characteristics of the gases flow. The at least one characteristic of the gases flow can comprise one or more of a gases concentration or a gases flow rate. The gases concentration can comprise an oxygen concentration, a carbon dioxide concentration, a heliox concentration, or a concentration of any other desired gases in the flow path. The system can further comprise a blower. The blower can be configured to provide a high flow therapy to a patient. The acoustic transmitter and the at least two acoustic receivers can be comprised within a removable sensor module. The blower, the acoustic transmitter and the at least two acoustic receivers can be comprised within a removable blower and sensor module. The removable sensor module or blower and sensor module can be configured for insertion into a housing of the respiratory system. The blower, the acoustic transmitter, and the at least two acoustic receivers can be comprised within a non-removable sensor module or blower and sensor module. The sensor module or the blower and sensor module can comprise a sensing circuit board. The acoustic transmitter and the at least two acoustic receivers can be located on the sensing circuit board. The system can further comprise a patient breathing conduit configured to be coupled to a gases flow outlet of the respiratory system on one end of the conduit and to a patient interface on another end of the conduit. The patient interface can be a nasal cannula, a full face mask, a nasal mask, a tracheostomy interface, a nasal pillows mask, or an endotracheal tube. The patient breathing conduit can comprise a heater wire configured to heat gases passing through the conduit. The system can further comprise a humidification chamber configured to humidify the gases flow to a patient. The system can further comprise a display configured to display the one or more characteristics of the gases flow. The acoustic signal(s) can comprise acoustic noises from the blower. The hardware processor can be configured to determine from the acoustic signal received at the acoustic receivers a fault condition in a blower motor. The fault condition can be related or correlatable to motor speed. The hardware processor can be configured to analyze spectrally the acoustic signal received at the acoustic receivers to determine a frequency or range of frequencies above a predetermined threshold. The hardware processor can be configured to determine a fault condition based on an amplitude, or a relationship of amplitudes between different fault conditions, or a threshold amplitude of the acoustic signal at a predetermined frequency or range of frequencies. The motor speed can be varied during a fault condition detection operation and the hardware processor can be configured to determine a fault condition based on a corresponding varying of a portion of the acoustic signal caused by or relating to the fault condition.

A respiratory assistance system for providing a flow of gases to a patient can comprise an acoustic source configured to generate an acoustic signal; and two acoustic receivers configured to receive the acoustic signal, the two acoustic receivers in electrical communication with a hardware processor configured to determine at least one characteristic of the gases flow based on the received acoustic signal. The at least one characteristic of the gases flow can comprise one or more of a gases concentration or a flow rate. The gases concentration can comprise an oxygen concentration, a carbon dioxide concentration, a heliox concentration, or a concentration of any other desired gases in the flow path. The system can comprise one or more of a pressure sensor, a humidity sensor, and/or a flow rate sensor. The flow rate sensor can be a heated temperature sensing element. The hardware processor can be configured to use outputs of the one or more of the pressure sensor, the humidity sensor, or the flow rate sensor to determine at least one characteristic of the gases flow. The processor can be configured to compensate for temperature difference between the two acoustic receivers and the gases flow based at least in part on measurements by the temperature sensor when determining the one or more characteristics of the gases flow. The processor can be configured to compute or adjust a calibration parameter of the acoustic source and/or the two acoustic receivers based on a flow rate measured by the flow rate sensor. The processor can be configured to determine a time of flight of the acoustic signal by determining a difference of time between a receipt of the at least first acoustic signal by a first one of the at least two acoustic receivers and a receipt of the at least first acoustic signal by a second one of the at least two acoustic receivers. The system can be configured to generate measurements of at least one characteristic of a gases flow of the system based on the difference of time between the receipt of the at least first acoustic signal by the first one of the at least two acoustic receivers and the second one of the at least two acoustic receivers. The at least two acoustic receivers can be microphones. The acoustic source can be an acoustic transmitter. The acoustic source can comprise first and second acoustic transducers. The first and second acoustic transducers can comprise first and second ultrasonic transducers. The first and second ultrasonic transducers can be a matched pair of acoustic transducers. Each of the first and second acoustic transducers can be configured to both transmit and receive acoustic signals such that the acoustic signals are transmitted in both upstream and downstream directions along an acoustic path between the first and second acoustic transducers. The at least two acoustic receivers can be positioned between the first and second acoustic transducers. The first and second acoustic transducers can be located substantially at or near each end of a measurement portion of a gases flow path. The at least two acoustic receivers can be located on a central axis of a gases flow path. The hardware processor can be configured to estimate a temperature of the at least two acoustic receivers to be at the same temperature as a measured temperature of gases in the flow path. The at least two acoustic receivers can be located in the measurement portion of the gases flow path in a configuration which avoids dead space in a measurement region. The system can comprise a first distance defined between the first one of the at least two acoustic receivers and the acoustic source, and a second distance defined between the second one of the at least two acoustic receivers and the acoustic source, the acoustic source being a single acoustic transducer or one of the first or second acoustic transducers. The hardware processor can be configured to use a time of flight measurement taken along the first distance to provide an estimate of a time of flight. The hardware processor can be configured to use a time of flight measurement taken along the second distance to provide a more accurate assessment of the time of flight. The first distance can be shorter than the second distance. The acoustic source can be the first or second transducers. The time of flight measurements can be generated from between the first one of the at least two acoustic receivers and the acoustic source, between the second one of the at least two acoustic receivers and the acoustic source, between the first and second ones of the at least two acoustic receivers, between the first and second acoustic transducers, or a combination thereof in both directions along an acoustic path. The hardware processor can be configured to compare two or more of the time of flight measurements to determine accuracy of the two or more of the time of flight measurements. The hardware processor can be configured to use acoustic signals received by the at least two acoustic receivers to perform cross-correlation of the received acoustic signals. The hardware processor can be configured to use acoustic signals received at the at least two acoustic receivers to determine waveform deformation. The hardware processor can be configured to use acoustic signals received by the at least two acoustic receivers to detect a flow rate by determining time delay for the time of flight measurements. The first acoustic signal can comprise an ultrasonic signal. The acoustic source can comprise one or more of a baffle and/or a blower. The blower can be configured to provide a high flow therapy to a patient. The hardware processor can be configured to cancel delays by taking a difference in time of flight measurements between the acoustic signals received by the two acoustic receivers. The two receivers can be located in a measurement portion of a gases flow path. The measurement portion of the gases flow path can comprise a curved flow path. The measurement portion of the gases flow path can comprise a portion of the flow path having a straight flow path. The at least two acoustic receivers can be comprised within a removable sensor module. The blower and the at least two acoustic receivers can be comprised within a removable blower and sensor module. The acoustic source can also be within the removable blower and sensor module. The removable sensor module or blower and sensor module can be configured for insertion into a housing of the respiratory system. The blower and the two acoustic receivers can be comprised within a non-removable blower and sensor module. The acoustic source can also be within the non-removable sensor module or blower and sensor module. The sensor module or the blower and sensor module can comprise a sensing circuit board. The at least two acoustic receivers can be located on the sensing circuit board. The acoustic source can also be located on the sensing circuit board. The system can further comprise a patient breathing conduit configured to be coupled to a gases flow outlet of the respiratory system on one end of the conduit and to a patient interface on another end of the conduit. The patient interface can be a nasal cannula, a full face mask, a nasal mask, a tracheostomy interface, a nasal pillows mask, or an endotracheal tube. The patient breathing conduit can comprise a heater wire configured to heat gases passing through the conduit. The system can further comprise a humidification chamber configured to humidify the gases flow to a patient. The system can further comprise a display configured to display the one or more characteristics of the gases flow. The acoustic signal(s) can comprise acoustic noises from the blower. The hardware processor can be configured to determine from the acoustic signal received at the acoustic receivers a fault condition in a blower motor. The fault condition can be related or correlatable to motor speed. The hardware processor can be configured to analyze spectrally the acoustic signal received at the acoustic receivers to determine a frequency or range of frequencies above a predetermined threshold. The hardware processor can be configured to determine a fault condition based on an amplitude, or a relationship of amplitudes between different fault conditions, or a threshold amplitude of the acoustic signal at a predetermined frequency or range of frequencies. The motor speed can be varied during a fault condition detection operation and the hardware processor can be configured to determine a fault condition based on a corresponding varying of a portion of the acoustic signal caused by or relating to the fault condition.

A respiratory therapy apparatus for providing respiratory gases to a patient can comprise a gases flow path configured to deliver a flow of gases to a patient; and one or more microphones placed in or near the gases flow path, the one or more microphones configured to receive at least one acoustic signal and transmit an indication of the received at least one acoustic signal to a hardware processor configured to determine at least one characteristic of a gases flow based on the received at least one acoustic signal. The one or more microphones can comprise one or more of condenser microphones, electret microphones, or MEMS microphones. The one or more microphones can comprise MEMS microphones. The one or more characteristics of the gases flow can comprise one or more of a gases concentration or a gases flow rate. The gases concentration can comprise an oxygen concentration, a carbon dioxide concentration, a heliox concentration, or a concentration of any other desired gases in the flow path. The gases flow path can comprise a curved flow path. The system can further comprise an acoustic transmitter. The acoustic transmitter can comprise an ultrasonic transmitter and the acoustic signal(s) can comprise an ultrasonic signal. The apparatus can comprise a first distance defined between the first one of the at least one microphones and an acoustic source, and a second distance defined between the second one of the at least one microphones and the acoustic source, the acoustic source being a single acoustic transducer or one of two acoustic transducers, the first distance being shorter than the second distance. The apparatus can be configured to generate measurements of at least one characteristic of the gases flow of the apparatus based on a difference of time between receipt of the at least one acoustic signal by a first one of the at least one microphones and a second one of the at least one microphones. The hardware processor can be configured to use a time of flight measurement taken along the first distance to provide an estimate of a time of flight. The hardware processor can be configured to use a time of flight measurement taken along the second distance to provide a more accurate assessment of the time of flight. The apparatus can be configured to generate measurements of at least one characteristic of the gases flow of the system based on a time taken to receive the at least one acoustic signal by one of the one or more microphones. The hardware processor can be configured to determine the at least one characteristic of the gases using only the time taken to receive the at least one acoustic signal by the one or more microphones. The apparatus can further comprise a patient breathing conduit configured to be coupled to a gases flow outlet of the respiratory system on one end of the conduit and to a patient interface on another end of the conduit. The patient interface can be a nasal cannula, a full face mask, a nasal mask, a tracheostomy interface, a nasal pillows mask, or an endotracheal tube. The patient breathing conduit can comprise a heater wire configured to heat gases passing through the conduit. The apparatus can further comprise a humidification chamber configured to humidify the gases flow to a patient. The apparatus can further comprise a display configured to display the one or more characteristics of the gases flow. The apparatus can further comprise one or more of a temperature sensor, a pressure sensor, a humidity sensor, and/or a flow rate sensor. The flow rate sensor can be a heated temperature sensing element. The hardware processor can be configured to be in communication with the one or more of the temperature sensor, the pressure sensor, the humidity sensor, and/or the flow rate sensor and to use outputs of the one or more of the temperature sensor, the pressure sensor, the humidity sensor, and/or the flow rate sensor to determine the one or more characteristics of the gases flow. The processor can be configured to compensate for a temperature difference between the one or more microphones and the gases flow based at least in part on measurements by the temperature sensor when determining the one or more characteristics of the gases flow. The processor can be configured to compute or adjust a calibration parameter of the one or more microphones based on a flow rate measured by the flow rate sensor. The apparatus can be any one of the systems described above, wherein the acoustic receiver(s) can be the one or more microphones. The apparatus can further comprise a blower. The blower can be configured to provide a high flow therapy to a patient. The one or more microphones can be comprised within a removable sensor module. The blower and the one or more microphones can be comprised within a removable blower and sensor module. The removable sensor module or blower and sensor module can be configured for insertion into a housing of the respiratory therapy apparatus. The sensor module or the blower and sensor module can comprise a sensing circuit board. The one or more microphones can be located on the sensing circuit board. The acoustic signal(s) can comprise acoustic noises from the blower. The hardware processor can be configured to determine from the acoustic noise(s) received at the acoustic receiver a fault condition in a blower motor. The fault condition can be related or correlatable to motor speed.

The hardware processor can be configured to analyze spectrally the acoustic noise(s) received at the acoustic receiver to determine a frequency or range of frequencies above a predetermined threshold. The hardware processor can be configured to determine a fault condition based on an amplitude, or a relationship of amplitudes between different fault conditions, or a threshold amplitude of the acoustic noise(s) at a predetermined frequency or range of frequencies. The motor speed can be varied during a fault condition detection operation and the hardware processor can be configured to determine a fault condition based on a corresponding varying of a portion of the acoustic noises caused by or relating to the fault condition.

A respiratory assistance system or apparatus can comprise a gases flow path configured to deliver a flow of gases to a patient, a source of respiratory gases; and one or more microphones, the one or more microphones configured to detect acoustic noise generated by the respiratory assistance apparatus and generate a signal representative of the detected acoustic noise, and a hardware processor configured to receive the signal representative of the detected acoustic noise and use the signal to determine a fault condition in the respiratory assistance apparatus. The detected acoustic noise can comprise at least in part a sound from a motor. The fault condition can be related or correlatable to a motor speed. The hardware processor can be configured to analyze spectrally the signal to determine a frequency or range of frequencies above a predetermined threshold. The hardware processor can be configured to determine a fault condition based on an amplitude, or a relationship of amplitudes between different fault conditions, or a threshold amplitude of the signal at a predetermined frequency or range of frequencies. The motor speed can be varied during a fault condition detection operation and the hardware processor is configured to determine a fault condition based on a corresponding varying of a portion of the signal caused by or relating to the fault condition.

A respiratory assistance system can comprise a gases flow path configured to deliver a flow of gases to a patient; an acoustic transmitter configured to generate an acoustic signal; and an acoustic receiver configured to receive the acoustic signal, the acoustic receiver being in electrical communication with a hardware processor configured to determine at least one characteristic of the gases flow of the system based on a time taken to receive the acoustic signal by the acoustic receiver. The hardware processor can be configured to determine the at least one characteristic of the gases using only the time taken to receive the acoustic signal by the acoustic receiver. The system can comprise a second acoustic receiver. The system can comprise a first distance defined between the acoustic receiver and the acoustic transmitter, and a second distance defined between the second acoustic receiver and the acoustic transmitter, the first distance being shorter than the second distance. The hardware processor can be configured to use a time of flight measurement taken along the first distance to provide an estimate of a time of flight. The hardware processor can be configured to use a time of flight measurement taken along the second distance to provide a more accurate assessment of the time of flight. The system can comprise a second acoustic transmitter configured to generate a second acoustic signal, the hardware processor configured to determine at least one characteristic of the gases flow of the system based on a time taken to receive the second acoustic signal by the acoustic receiver and/or the second acoustic receiver. The acoustic receiver and the second acoustic receiver can be located between and spaced from the acoustic transmitter and a second acoustic transmitter. The hardware processor can be configured to compare two or more of the time of flight measurements to determine accuracy of the two or more of the time of flight measurements. The acoustic transmitter can be an ultrasonic transmitter. The acoustic receiver can be a microphone. The at least one characteristic of the gases flow can comprise one or more of a gases concentration or a gases flow rate. The gases concentration can comprise an oxygen concentration, a carbon dioxide concentration, or a heliox concentration. The acoustic receiver can be located within the gases flow path. The system can comprise one or more of a temperature sensor, a pressure sensor, a humidity sensor, and/or a flow rate sensor. The flow rate sensor can be a heated temperature sensing element. The hardware processor can be configured to be in communication with the one or more of the temperature sensor, the pressure sensor, the humidity sensor, and/or the flow rate sensor and to use outputs of the one or more of the temperature sensor, the pressure sensor, the humidity sensor, and/or the flow rate sensor to determine the at least one characteristic of the gases flow. The processor can be configured to compensate for temperature difference between the acoustic receiver and the gases flow based at least in part on measurements by the temperature sensor when determining the one or more characteristics of the gases flow. The processor can be configured to compute or adjust a calibration parameter of the acoustic transmitter and/or the acoustic receiver based on a flow rate measured by the flow rate sensor. The gases flow path can comprise a curved flow path. The system can further comprise a blower. The blower can be configured to provide a high flow therapy to a patient. The acoustic transmitter and the acoustic receiver can be comprised within a removable sensor module. The acoustic transmitter and the acoustic receiver can be comprised within a removable blower and sensor module. The removable sensor module or blower and sensor module can be configured for insertion into a housing of the respiratory assistance system. The sensor module or the blower and sensor module can comprise a sensing circuit board. The acoustic transmitter and the acoustic receiver can be located on the sensing circuit board.

The above examples are intended to be within the scope of the disclosure herein. These and other examples will become readily apparent to those skilled in the art from the following detailed description having reference to the attached figures, the disclosure not being limited to any particular disclosed example(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 18A-E illustrate various views of an example flow therapy apparatus.

FIG. 22A illustrates a sensing circuit board of an example sensing chamber.

DETAILED DESCRIPTION

Although certain examples are described below, those of skill in the art will appreciate that the disclosure extends beyond the specifically disclosed examples and/or uses and obvious modifications and equivalents thereof. Thus, it is intended that the scope of the disclosure herein should not be limited by any particular examples described below.

Figure 1:
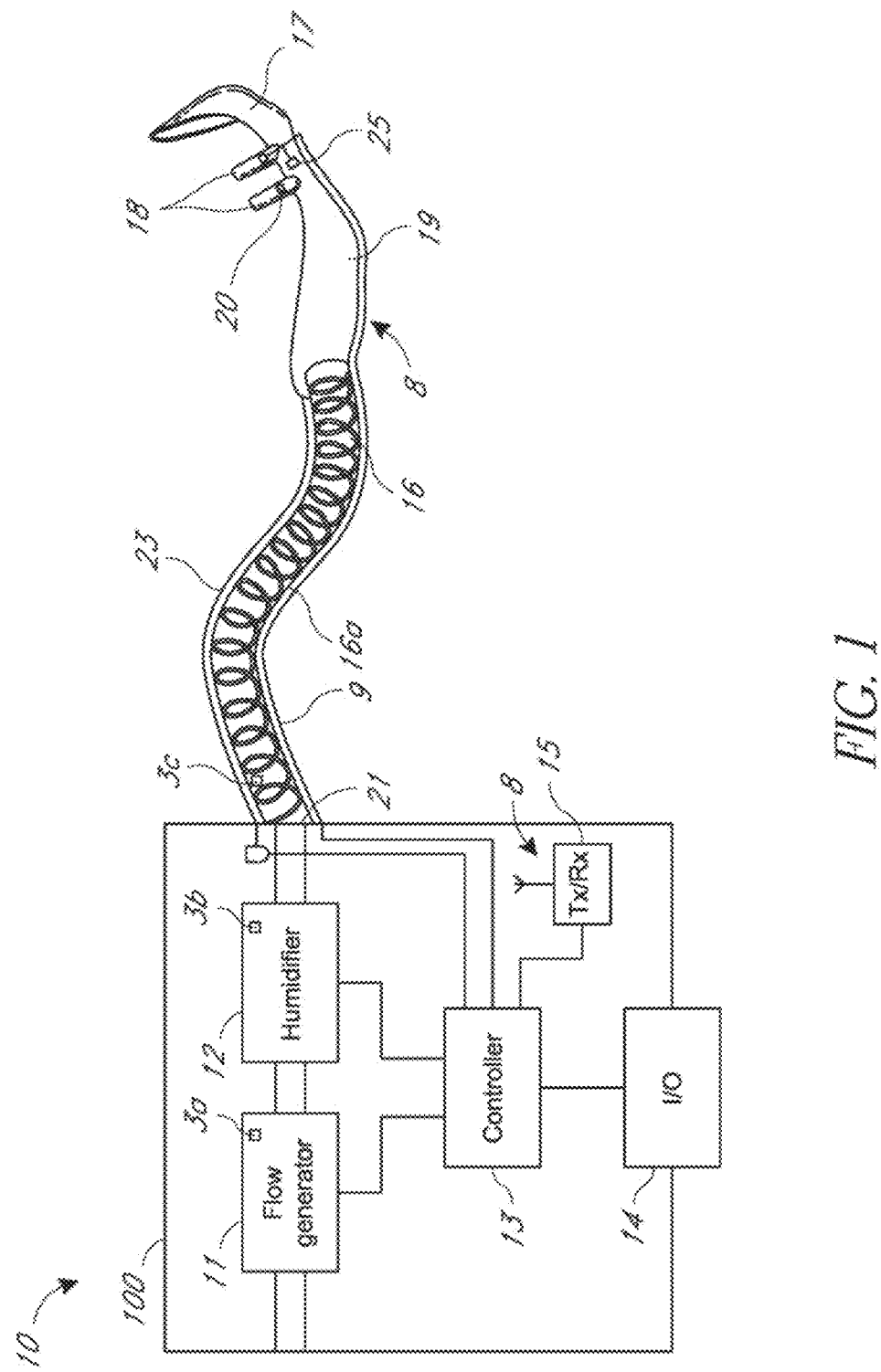
FIG. 1 shows in diagrammatic form a breathing assistance apparatus in the form of a flow therapy apparatus.
Figure 2:
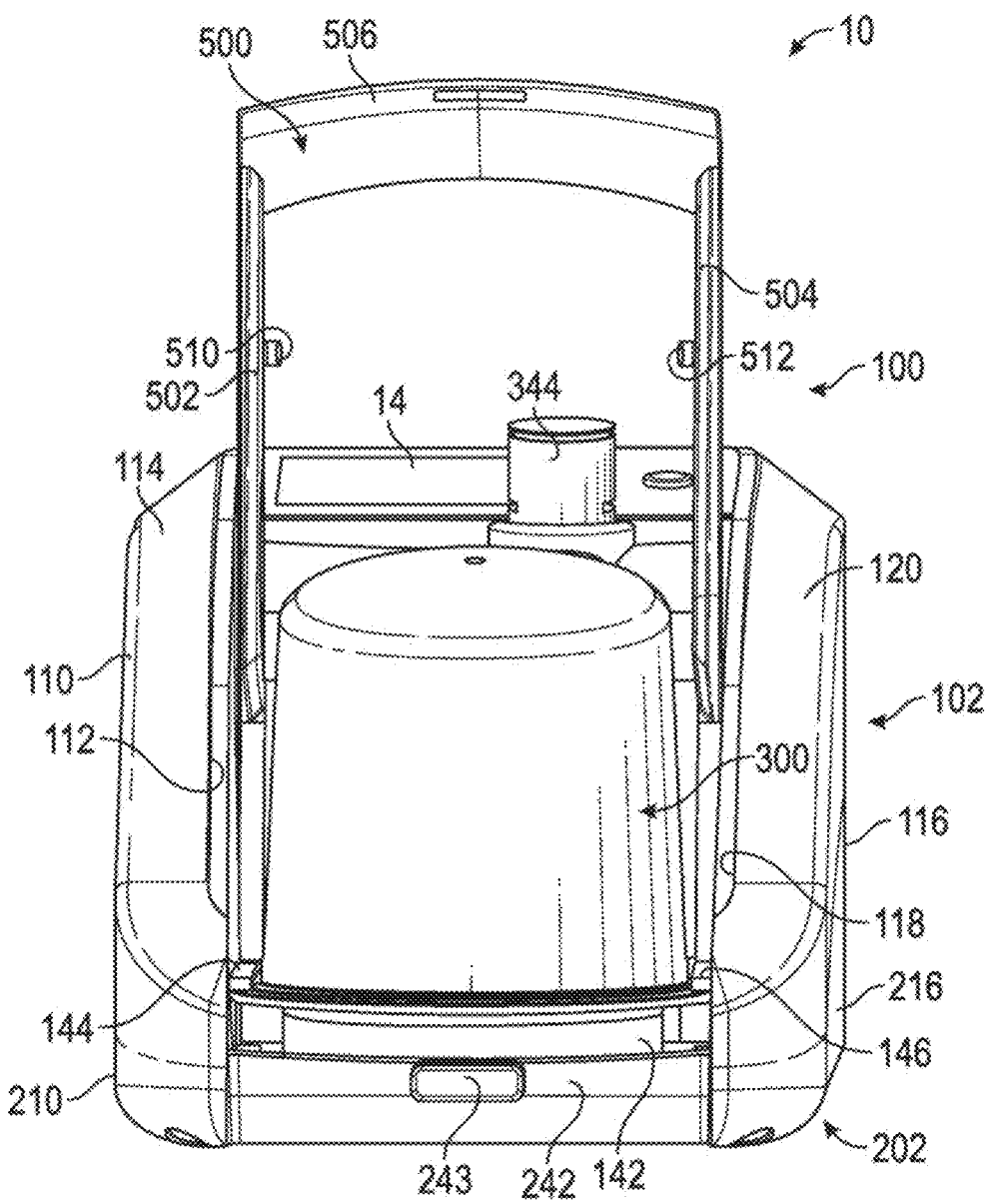
FIG. 2 is a front view of the flow therapy apparatus with a humidifier chamber in position and a raised handle/lever.
Figure 3:
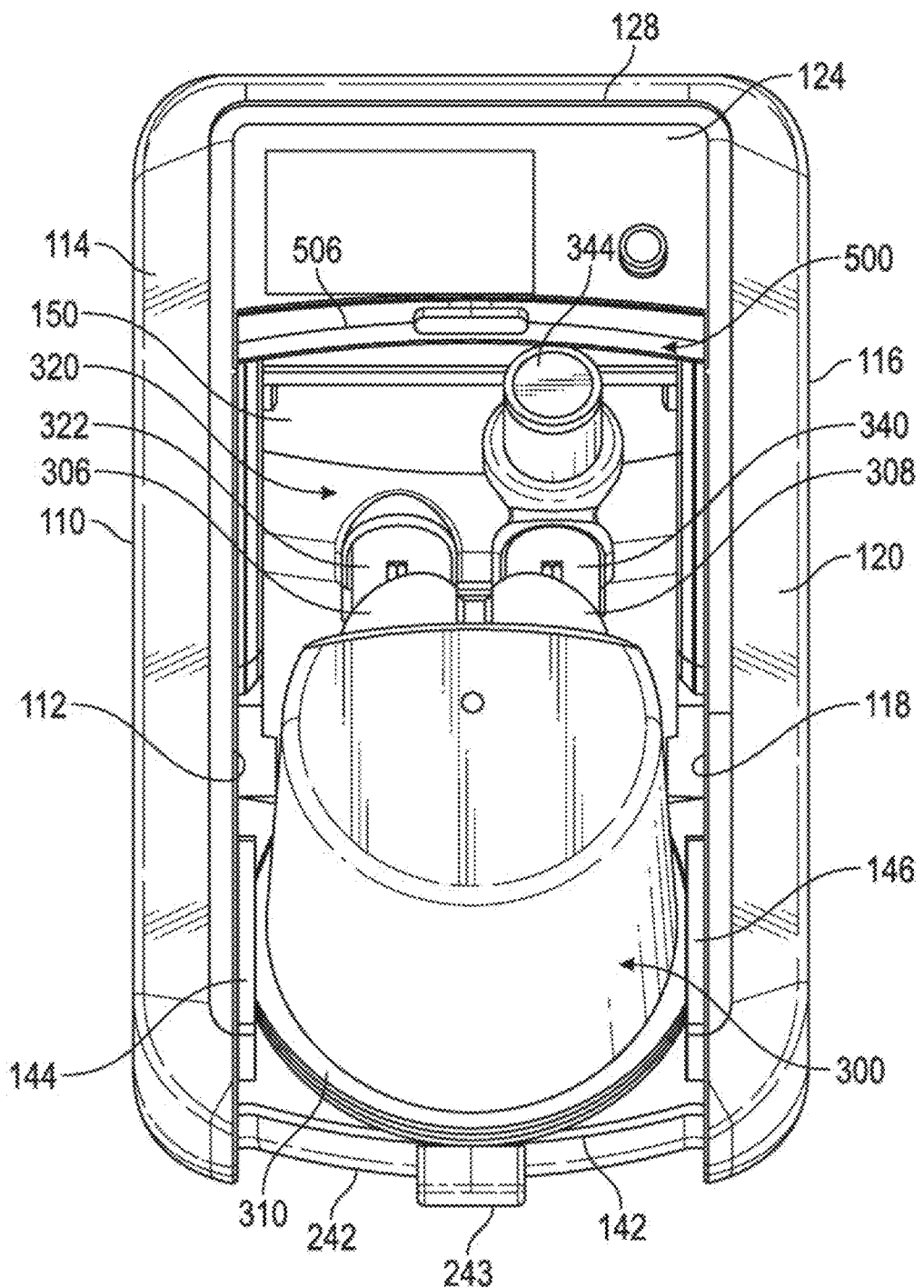
FIG. 3 is a top view corresponding to FIG. 2.
Figure 4:
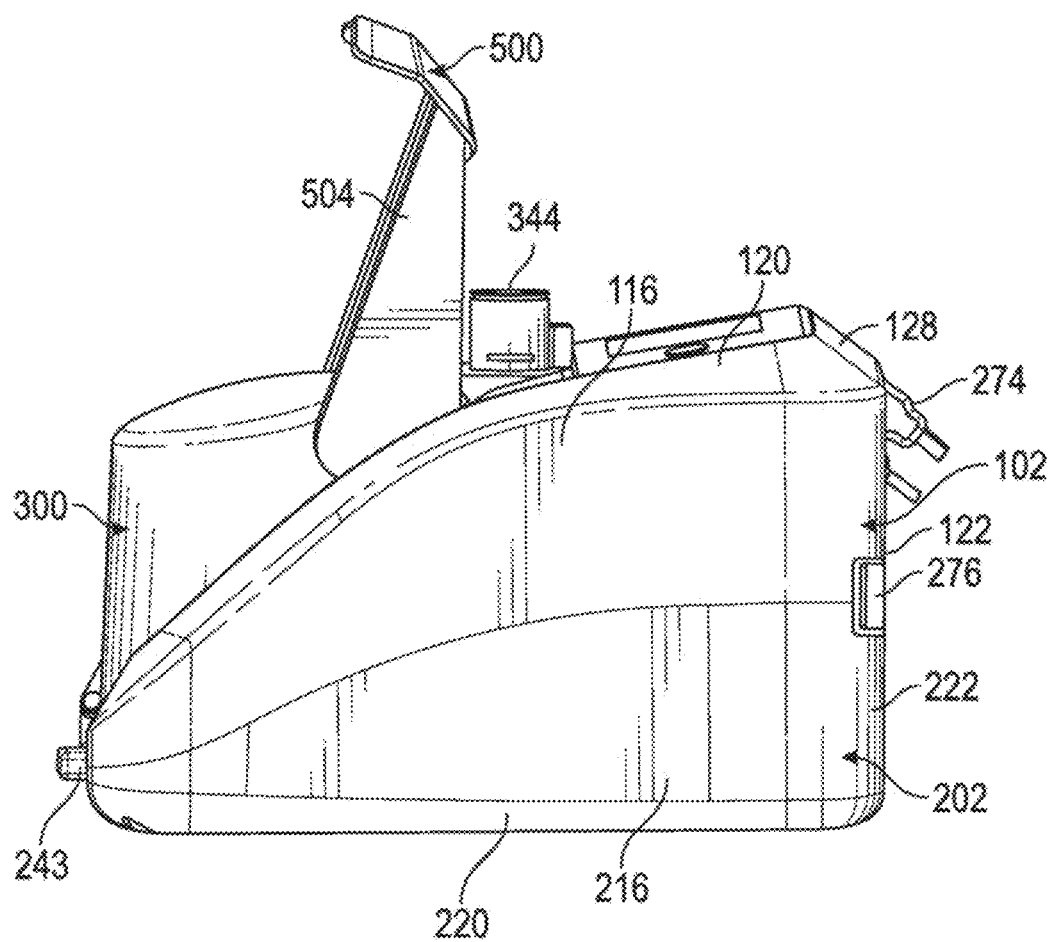
FIG. 4 is a right side view corresponding to FIG. 2.
Figure 5:
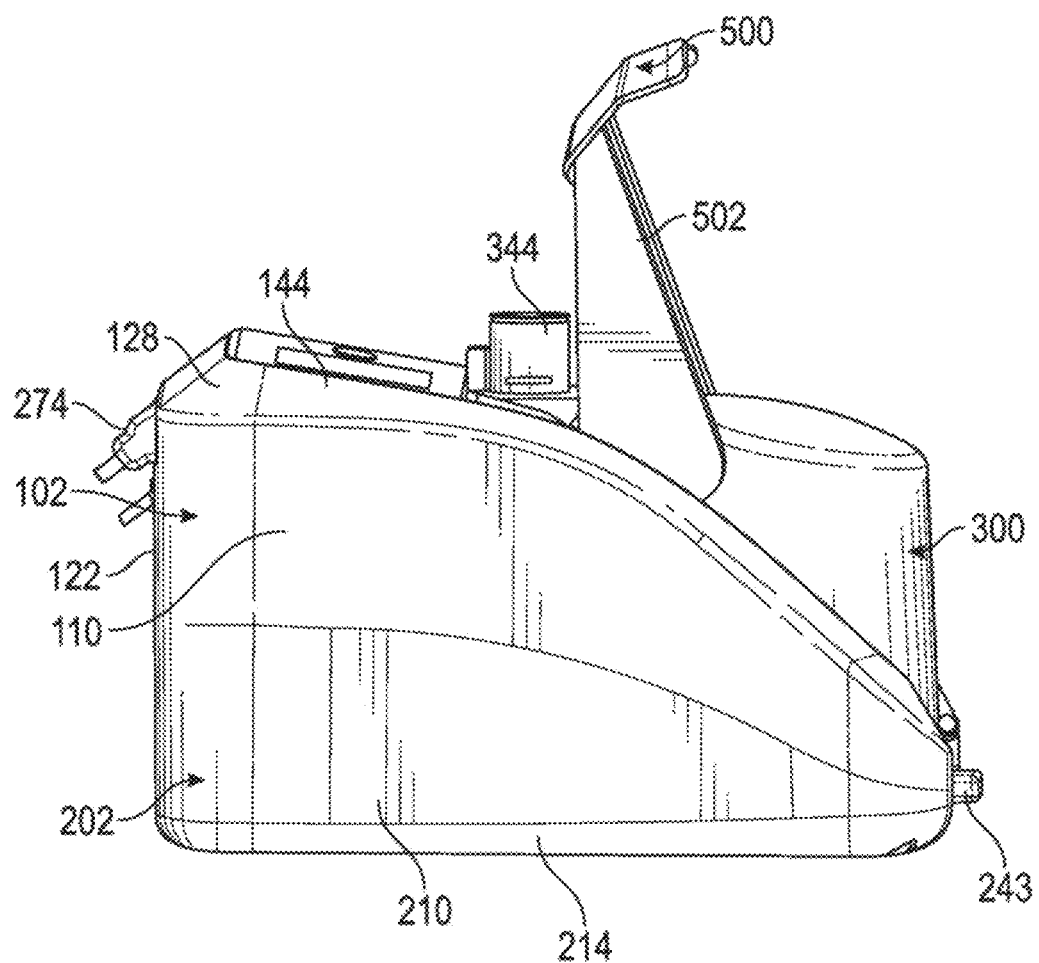
FIG. 5 is a left side view corresponding to FIG. 2.
Figure 6:
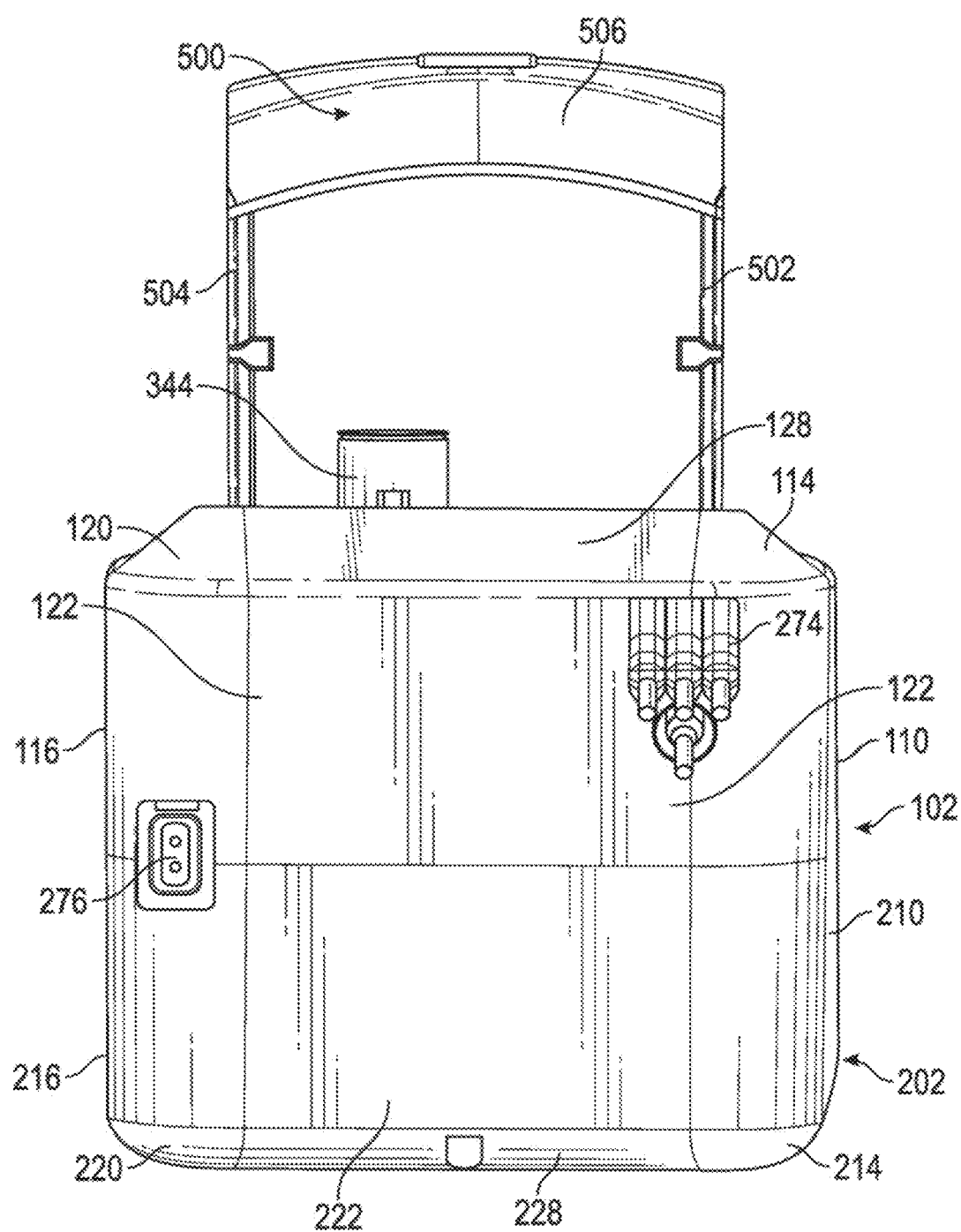
FIG. 6 is a rear view corresponding to FIG. 2.
Figure 7:
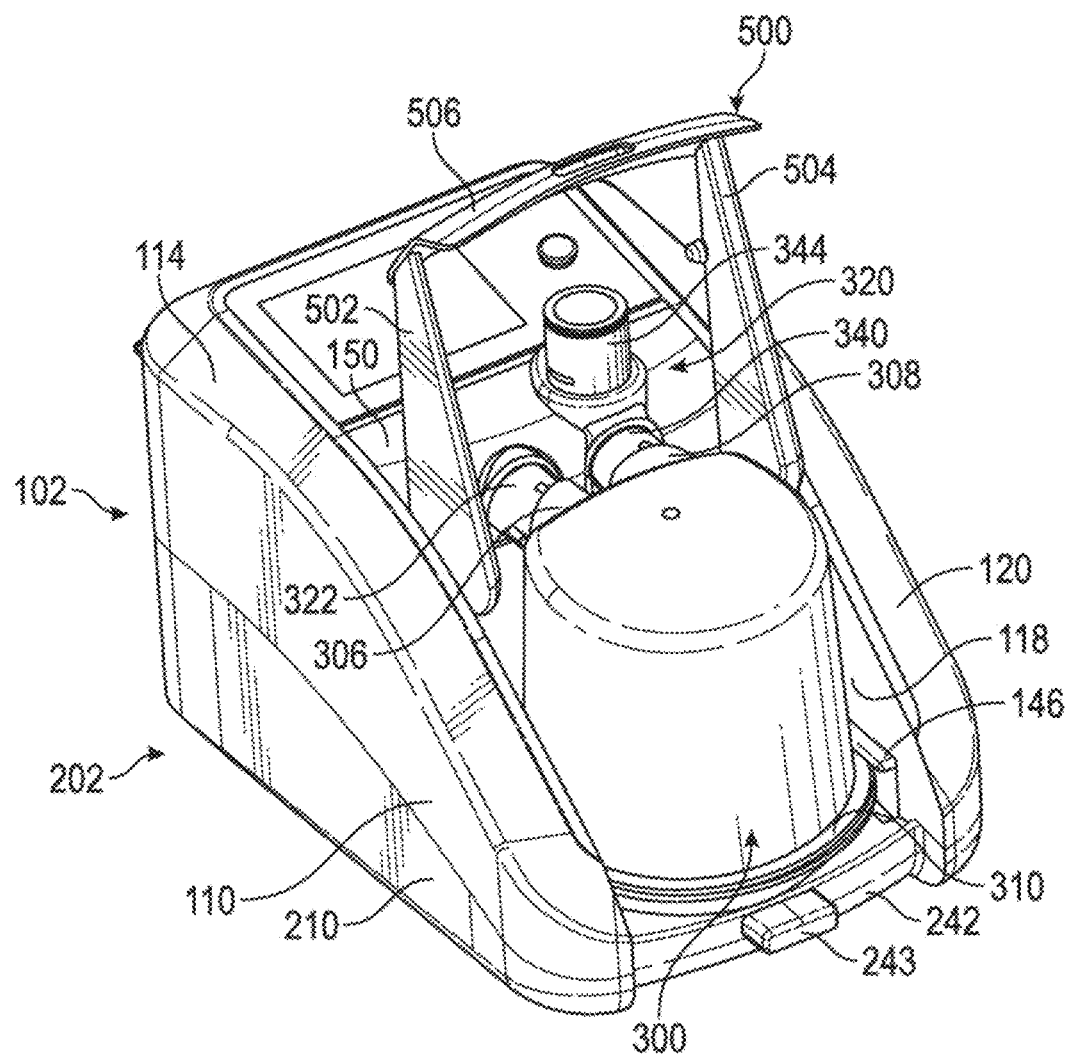
FIG. 7 is a front left perspective view corresponding to FIG. 2.

A schematic representation of a respiratory system or flow therapy apparatus 10 is provided in FIG. 1. The apparatus 10 can include a main housing 100. The main housing 100 can contain a flow generator 11 that can be in the form of a motor/impeller arrangement, an optional humidifier or humidification chamber 12, a controller 13, and a user interface 14. The user interface 14 can include a display and input device(s) such as button(s), a touch screen, a combination of a touch screen and button(s), or the like. The controller 13 can include a hardware processor and can be configured or programmed to control the components of the apparatus, including but not limited to operating the flow generator 11 to create a flow of gases for delivery to a patient, operating the humidifier 12 (if present) to humidify and/or heat the gases flow, receiving user input from the user interface 14 for reconfiguration and/or user-defined operation of the apparatus 10, and outputting information (for example on the display) to the user. The user can be a patient, healthcare professional, or anyone else interested in using the apparatus.

With continued reference to FIG. 1, a patient breathing conduit 16 can be coupled to a gases flow outlet 21 in the housing 100 of the flow therapy apparatus 10, and be coupled to a patient interface 17, such as a non-sealing interface like a nasal cannula with a manifold 19 and nasal prongs 18. Additionally, or alternatively, the patient breathing conduit 16 can be coupled to a face mask, or a tracheostomy interface. The gases flow that is generated by the flow therapy apparatus 10, and which may be humidified, is delivered to the patient via the patient conduit 16 through the cannula 17. The patient conduit 16 can have a heater wire 16a to heat gases flow passing through to the patient. The heater wire 16a can be under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together can form a flow therapy system.

General operation of a flow therapy breathing apparatus 10 will now be described. The controller 13 can control the flow generator 11 to generate a gases flow of a desired flow rate, one or more valves to control mixing of air and oxygen or other breathable gas, and/or the humidifier 12, if present, to humidify the gases flow to an appropriate temperature and/or humidity. As will be described in greater detail below, the apparatus 10 can use ultrasonic sensing to monitor characteristics of the gases in the flow. For example, the characteristics of the gases flow can include gases concentration, flow rate, or the like. The apparatus 10 can include additional sensors that can be in communication with the hardware processor. These sensors can include a flow rate sensor, a temperature sensor, a humidity sensor, a pressure sensor, or the like. Output of the additional sensors can be used for determining the characteristics of the gases flow, such as temperature, pressure, humidity, and the like. Output of the additional sensors can be used for correcting measurement of the characteristics of the gases flow by ultrasonic sensing. The gases flow can be directed out through the patient conduit 16 and cannula 17 to the patient. The cannula 17 may instead be any other patient interface, such as a full face mask, nasal mask, nasal pillows mask, tracheostomy interface, or endotracheal tube. The controller 13 can also control a heating element in the humidifier 12 and/or the heating element 16a in the patient conduit 16 to heat the gas to a desired temperature that achieves a desired level of therapy and/or level of comfort for the patient. The controller 13 can be programmed with or can determine a suitable target temperature of the gases flow using one or more temperature sensors.

Additional sensors 3a, 3b, 3c, 20, 25, such as flow, temperature, humidity, and/or pressure sensors, can be placed in various locations in the flow therapy apparatus 10 and/or the patient conduit 16 and/or cannula 17. The controller 13 can receive output from the sensors to assist it in operating the flow therapy apparatus 10 in a manner that provides suitable therapy. Providing suitable therapy can include meeting a patient's inspiratory demand. The apparatus 10 can include a wireless data transmitter and/or receiver, or a transceiver 15 to enable the controller 13 to receive data signals 8 in a wireless manner from the operation sensors and/or to control the various components of the flow therapy apparatus 10. Additionally, or alternatively, the data transmitter and/or receiver 15 may deliver data to a remote server or enable remote control of the apparatus 10. The apparatus 10 can include a wired connection, for example, using cables or wires, to enable the controller 13 to receive data signals 8 from the operation sensors and/or to control the various components of the flow therapy apparatus 10.

Overview of Example Flow Therapy Apparatus

The flow therapy apparatus 10 can include a high flow therapy apparatus. As used herein, "high flow" therapy refers to administration of gas to the airways of a patient at a relatively high flow rate that meets or exceeds the peak inspiratory demand of the patient. The flow rates to achieve "high flow" may be any of the flow rates listed below. The flow therapy apparatus may be any suitable type of apparatus, but in some configurations may deliver a high gases flow or high flow therapy (of for example, air, oxygen, nitrogen, other gas mixture, or some combination thereof) to a patient to assist with breathing and/or treat breathing disorders. The gas can be or comprise oxygen. The gas can comprise ambient air. The gas can comprise a blend of oxygen and ambient air. The gas can also optionally comprise one or more hypoxic gases, such as nitrogen or other gases to ambient air or oxygen, resulting in a gas with a reduced oxygen concentration. The gas can include a blend of nitrogen and ambient air to create hypoxic gas compositions. The gas can be a less than 100% pure enriched hypoxic gas, such as a hypoxic mix of nitrogen and oxygen that is mixed with ambient air, which can be advantageous from a safety perspective. Generating a hypoxic environment can, among other uses, be shown to simulate an artificial high-altitude environment, which can be useful for altitude training without a user having to be at a geological high altitude.

"High flow therapy" as used in this disclosure may refer to delivery of gases to a patient at a flow rate of greater than or equal to about 10 liters per minute (10 LPM), or to a neonatal, infant, or child patient at a flow rate of greater than or equal to about 1 liters per minute (1 LPM). "High flow therapy" for an adult patient may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For a neonatal, infant, or child patient, 'high flow therapy' may refer to the delivery of gases to a patient at a flow rate of between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and about 25 LPM. Therefore, a high flow therapy apparatus for use with either an adult patient or a neonatal, infant, or child patient, may deliver gases to the patient at a flow rate of between about 1 LPM and about 100 LPM, or at a flow rate in any of the sub-ranges outlined above. Gases delivered may comprise a percentage of oxygen. The percentage of oxygen in the gases delivered may be between about 0% and about 20%, between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy can be effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gases flow. This can create a reservoir of fresh gas available of each and every breath, while minimizing re-breathing of carbon dioxide, nitrogen, etc.

The percentage of oxygen in the gases delivered, where hypoxia is desired, can be such that the percentage of oxygen in the gas composition delivered to the subject is less than that of typical room air (such as less than about 21%). The percentage of oxygen in the gas composition is between about 10% and about 20.9%, or between about 11.9% and about 17.4%, or between about 13.8% and about 17.4%, or between about 15.7% and about 16.7%, or between about 15% and about 20%, or between about 13% and about 18%, or about or no more than about 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, or 20.5%, or any ranges incorporating two of the aforementioned values. In some embodiments, the percentage of nitrogen in the hypoxic gas composition is about or at least about 78.2%, 78.5%, 79%, 79.5%, 80%, 80.5%, 81%, 81.5%, 82%, 82.5%, 83%, 83.5%, 84%, 84.5%, 85%, 85.5%, 86%, 86.5%, 87%, 87.5%, 88%, 88.5%, 89%, 89.5%, 90%, or more, or any ranges incorporating two of the aforementioned values.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

It is to be understood throughout the present disclosure that the hardware and software components described are not limited solely to application as in high flow therapy. Rather, all aspects of the present disclosure can be applied in any number of known respiratory therapies including, but not limited to, for use in hospital and/or at home, adult and/or infant noninvasive ventilation therapy, invasive ventilation therapy, nasal high flow therapy, oxygen therapy, continuous positive pressure (CPAP) therapy, and laparoscopic surgery, or infant resuscitation, or any other therapies as would be understood by a person of skill in the art from the present disclosure. For example, the flow therapy apparatus 10 can also be used as a continuous positive airway pressure (CPAP) device. The CPAP device can be used for treatment of obstructive sleep apnea and/or other respiratory problems in adults and/or infants. A sealed patient interface can be used to deliver the humidified pressurized gases to a patient. The sealed patient interface can include a face mask, nasal mask, or nasal pillows mask. As the patient interface is sealed, the CPAP device can deliver the gases to the patient at a constant and/or predetermined pressure.

FIGS. 2 to 17B show an example flow therapy apparatus 10 having a main housing 100. The main housing 100 has a main housing upper chassis 102 and a main housing lower chassis 202.

Figure 15:
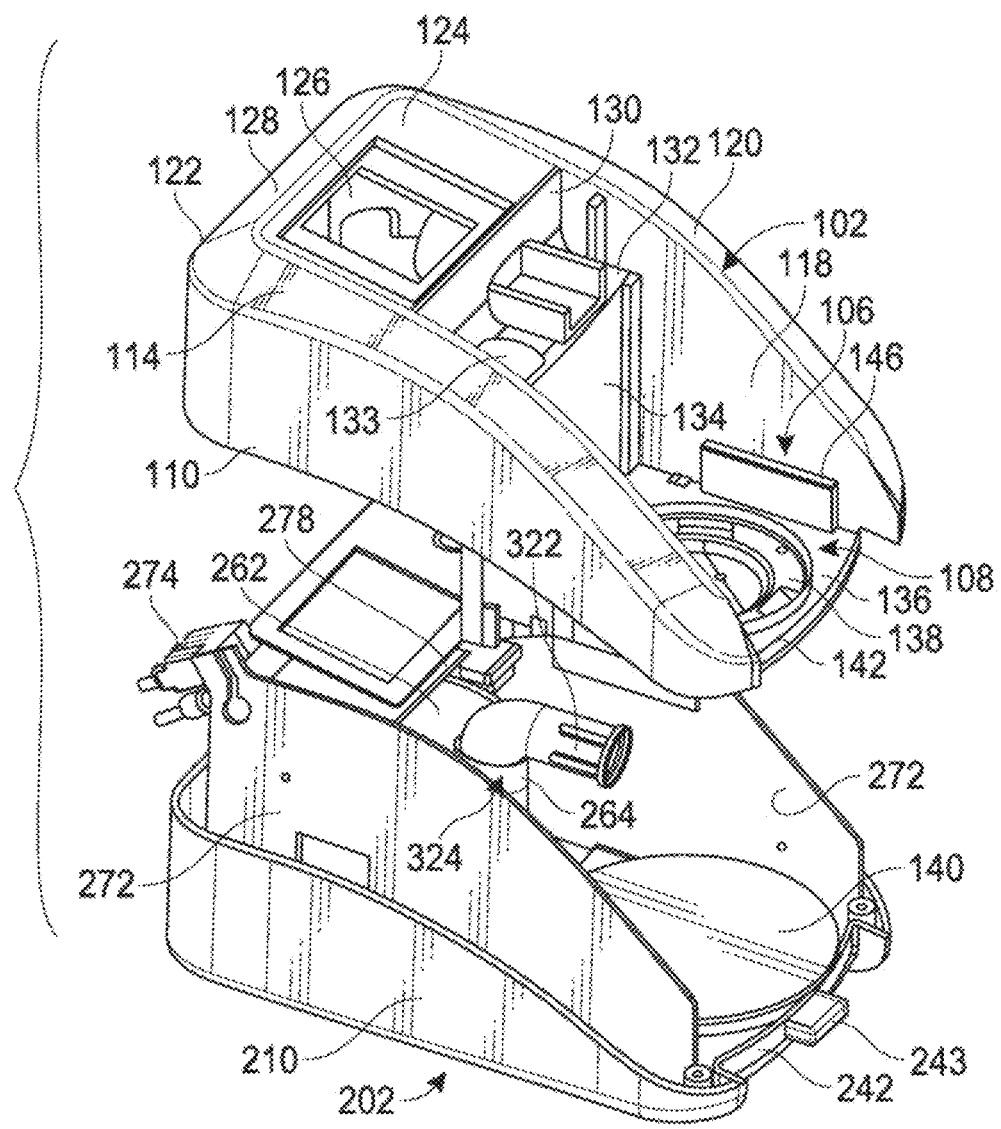
FIG. 15 is an exploded view of upper and lower chassis components of a main housing of the flow therapy apparatus.
Figure 16:
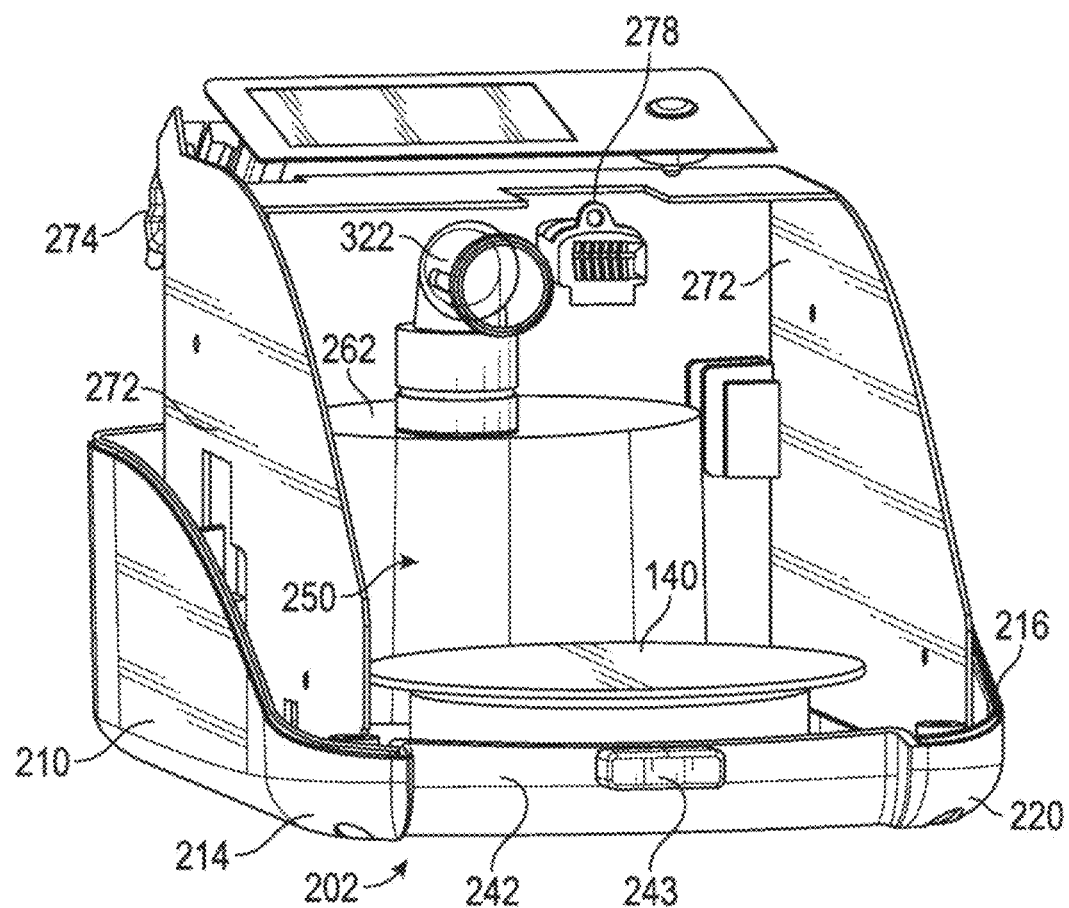
FIG. 16 is a front left side perspective view of the lower chassis of the main housing showing a housing for receipt of a motor and sensor module sub-assembly.

The main housing upper chassis 102 has a peripheral wall arrangement 106 (see FIG. 15). The peripheral wall arrangement defines a humidifier or humidification chamber bay 108 for receipt of a removable humidification chamber 300. The removable humidification chamber 300 contains a suitable liquid such as water for humidifying gases that can be delivered to a patient.

In the form shown, the peripheral wall arrangement 106 of the main housing upper chassis 102 can include a substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 can further include a substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but can alternatively be substantially horizontal or inwardly angled.

The main housing upper chassis 102 can further include a substantially vertical rear outer wall 122. An upper part of the main housing upper chassis 102 can include a forwardly angled surface 124. The surface 124 can have a recess 126 for receipt of a display and user interface module 14. The display can be configured to display characteristics of sensed gas(es) in real time. An interconnecting wall 128 can extend between and interconnect the upper end of the rear outer wall 122 and the rear edge of the surface 124.

A substantially vertical wall portion 130 can extend downwardly from a front end of the surface 124. A substantially horizontal wall portion 132 can extend forwardly from a lower end of the wall portion 130 to form a ledge. A substantially vertical wall portion 134 can extend downwardly from a front end of the wall portion 132 and terminate at a substantially horizontal floor portion 136 of the humidification chamber bay 108. The left side inner wall 112, right side inner wall 118, wall portion 134, and floor portion 136 together can define the humidification chamber bay 108. The floor portion 136 of the humidification chamber bay 108 can have a recess 138 to receive a heater arrangement such as a heater plate 140 or other suitable heating element(s) for heating liquid in the humidification chamber 300 for use during a humidification process.

The main housing lower chassis 202 can be attachable to the upper chassis 102, either by suitable fasteners or integrated attachment features such as clips for example. The main housing lower chassis 202 can include a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 can further include a substantially vertical rear outer wall 222 that is contiguous with the rear outer wall 122 of the upper chassis 102.

The lower housing chassis 202 can have a lip 242 that is contiguous with the lip 142 of the upper housing chassis 102, and also forms part of the recess for receiving the handle portion 506 of the lever 500. The lower lip 242 can include a forwardly directed protrusion 243 that acts as a retainer for the handle portion 506 of the lever 500.

An underside of the lower housing chassis 202 can include a bottom wall 230. Respective interconnecting walls 214, 220, 228 can extend between and interconnect the substantially vertical walls 210, 216, 222 and the bottom wall 230. The bottom wall 230 can include a grill 232 comprising a plurality of apertures to enable drainage of liquid in case of leakage from the humidification chamber 300 (e.g. from spills). The bottom wall 230 additionally can include elongated forward-rearward oriented slots 234. The slots 234 can additionally enable drainage of liquid in case of leakage from the humidification chamber 300, without the liquid entering the electronics housing. In the illustrated configuration, the slots 234 can be wide and elongate relative to the apertures of the grill 232 to maximize the drainage of liquid.

Figure 17A:
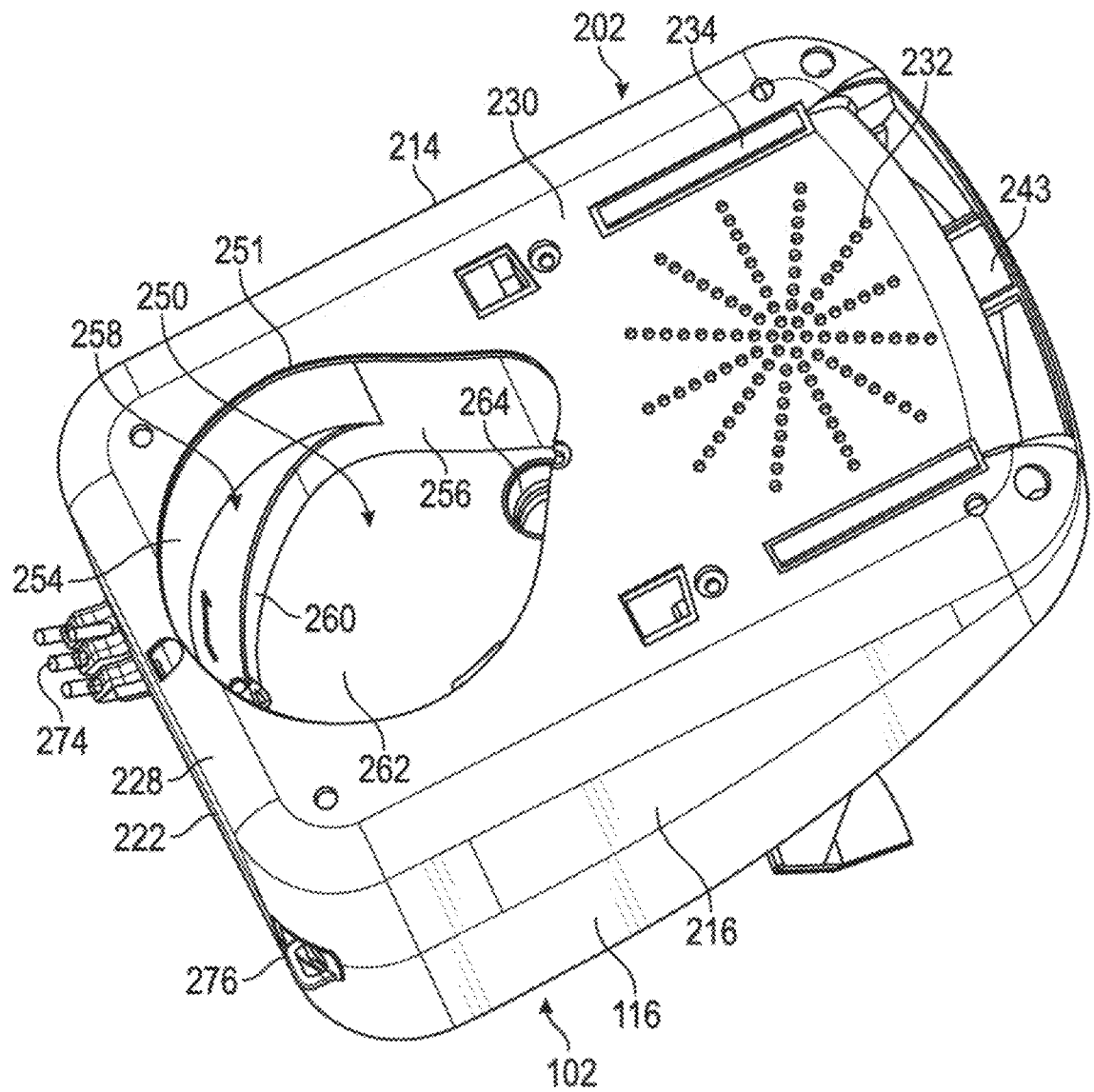
FIG. 17A is a first underside perspective view of the main housing of the flow therapy apparatus showing a recess inside the housing for the motor and sensor module sub-assembly.
Figure 17B:
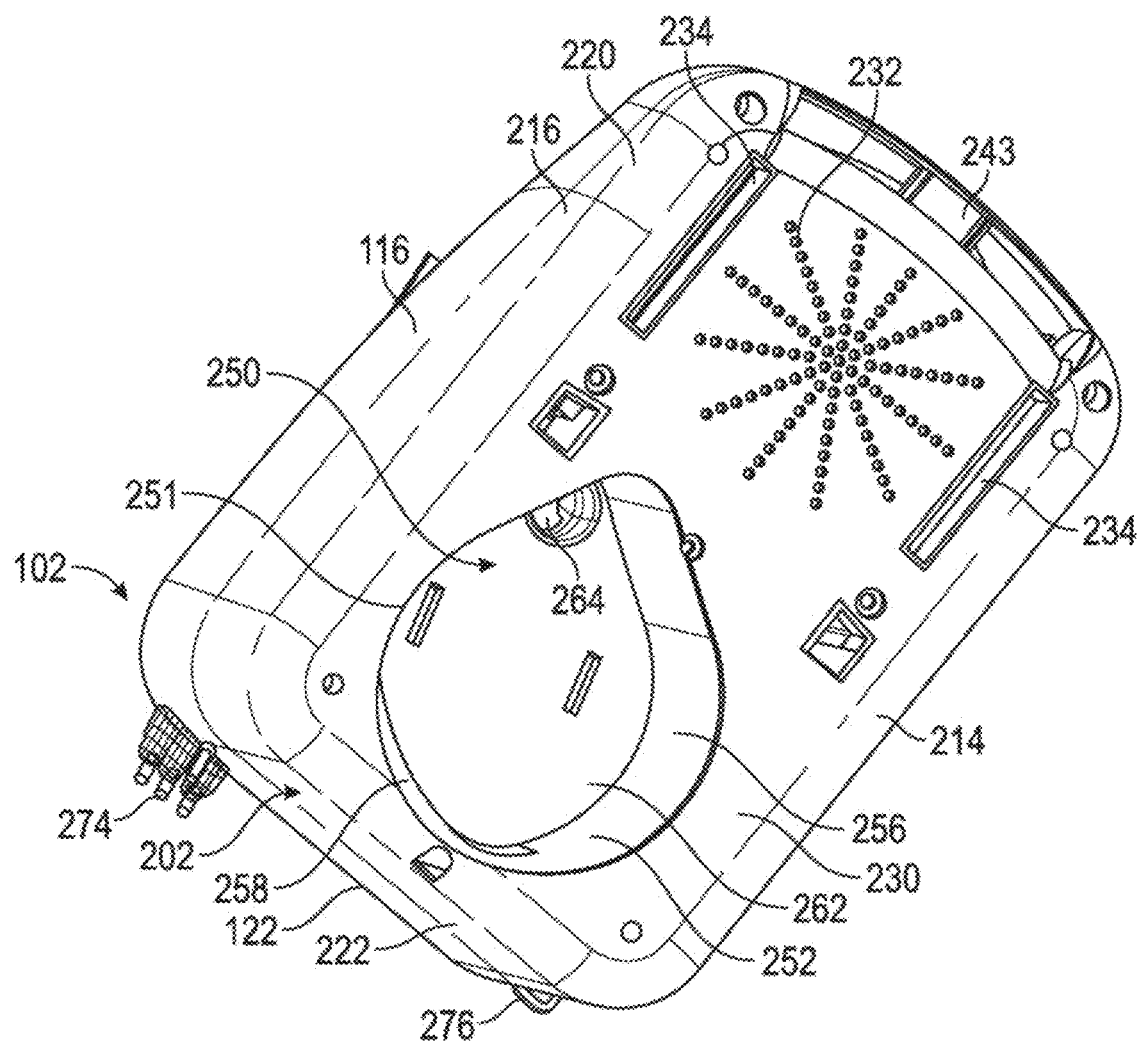
FIG. 17B is a second underside perspective view of the main housing of the flow therapy apparatus showing the recess for the motor and sensor module sub-assembly.

As shown in FIG. 17A to 17B, the lower chassis 202 can have a motor recess 250 for receipt of a motor and sensor module. Although not shown, the flow therapy apparatus 10 can also have a sensor module without the motor in the module. The motor and sensor module may be non-removable from the main housing 100. The motor and sensor module may be removable from the main housing 100, as illustrated in FIGS. 17A-17B. The module can be a motor and sensor module including the motor and a plurality of sensors. The module can be a sensor module including a plurality of sensors without the motor. A recess opening 251 can be provided in the bottom wall 230 adjacent a rear edge thereof, for receipt of a removable motor and sensor module. A continuous, gas impermeable, unbroken peripheral wall 252 can be integrally formed with the bottom wall 230 of the lower chassis 202 and extend upwardly from the periphery of the opening 251. A rearward portion 254 of the peripheral wall 252 has a first height, and a forward portion 256 of the peripheral wall 252 has a second height that is greater than the first height. The rearward portion 254 of the peripheral wall 252 terminates at a substantially horizontal step 258, which in turn terminates at an upper auxiliary rearward portion 260 of the peripheral wall 252. The forward portion 256 and upper auxiliary rearward portion 260 of the peripheral wall 252 terminate at a ceiling 262. All of the walls and the ceiling 262 can be continuous, gas impermeable, and unbroken other than the gases flow passage. Therefore, the entire motor recess 250 can be gas impermeable and unbroken, other than the gases flow passage.

The motor and sensor module may be insertable into the recess 250 and attachable to the lower chassis 202. Upon insertion of the motor and sensor module into the lower chassis 202, the gases flow passage tube 264 can extend through the downward extension tube 133 and be sealed by the soft seal.

The humidification chamber 300 can be fluidly coupled to the apparatus 10 in a linear slide-on motion in a rearward direction of the humidification chamber 300 into the chamber bay 108, from a position at the front of the housing 100 in a direction toward the rear of the housing 100. A gases outlet port 322 can be in fluid communication with the motor.

Figure 8:
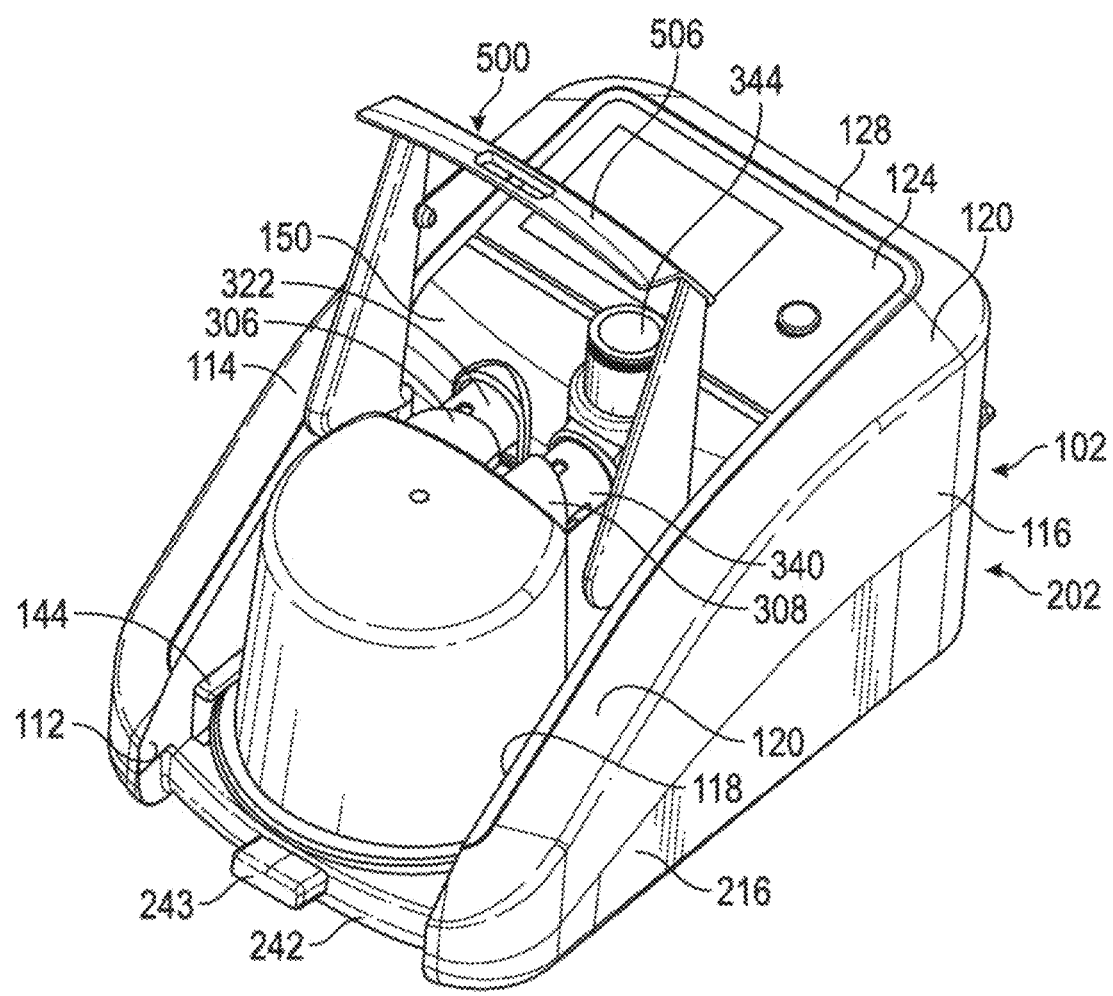
FIG. 8 is a front right perspective view corresponding to FIG. 2.
Figure 9:
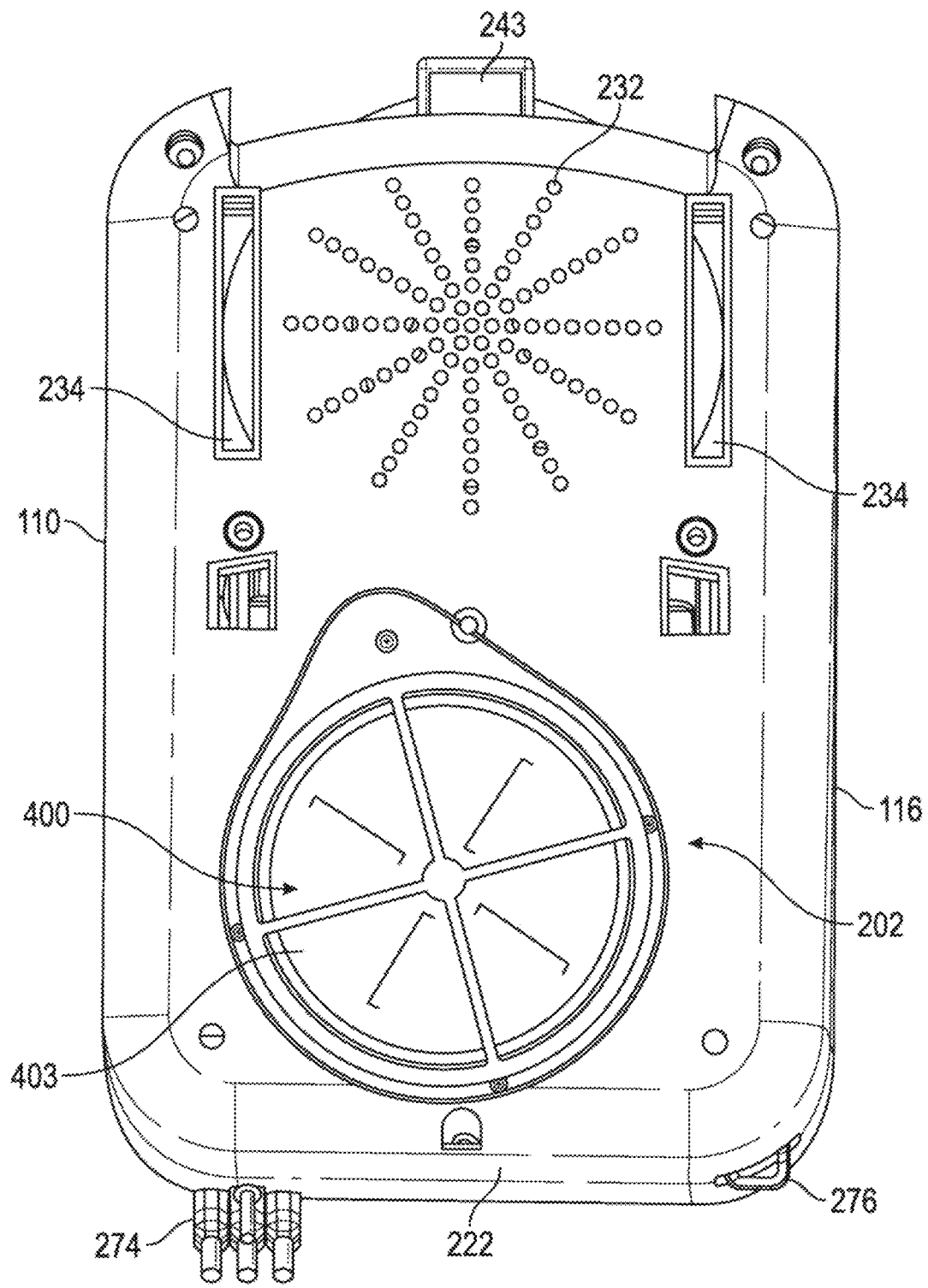
FIG. 9 is a bottom view corresponding to FIG. 2.

A gases inlet port 340 (humidified gases return) as shown in FIG. 8 can include a removable L-shaped elbow. The removable elbow can further include a patient outlet port 344 for coupling to the patient conduit 16 to deliver gases to the patient interface 17. The gases outlet port 322, gases inlet port 340, and patient outlet port 344 each can have soft seals such as O-ring seals or T-seals to provide a sealed gases passageway between the apparatus 10, the humidification chamber 300, and the patient conduit 16.

The humidification chamber gases inlet port 306 can be complementary with the gases outlet port 322, and the humidification chamber gases outlet port 308 can be complementary with the gases inlet port 340. The axes of those ports can be parallel to each other to enable the humidification chamber 300 to be inserted into the chamber bay 108 in a linear movement.

Figure 10:
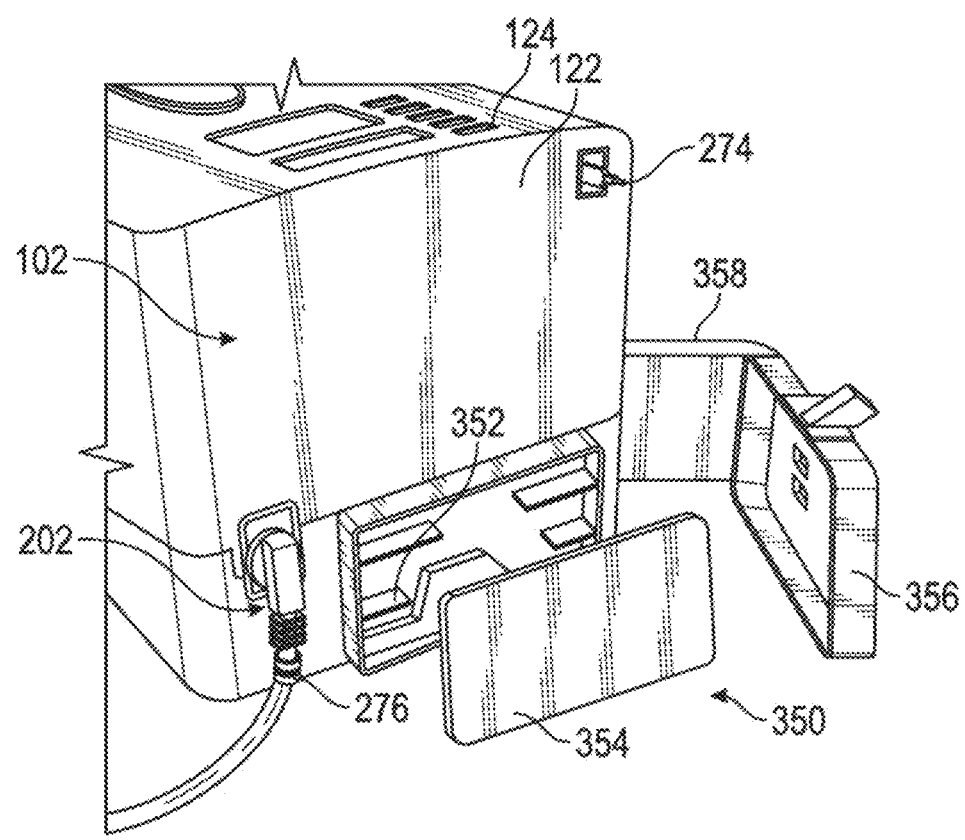
FIG. 10 shows a first configuration of an air and auxiliary gases inlet arrangement of the flow therapy apparatus.
Figure 11:
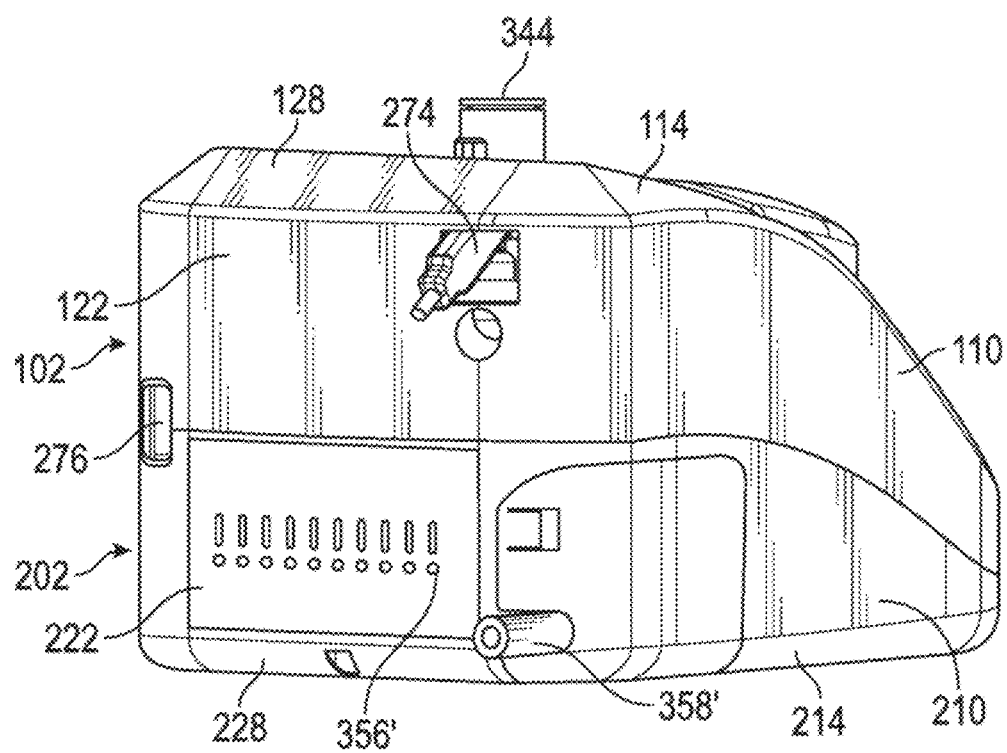
FIG. 11 shows a second configuration of an air and auxiliary gases inlet arrangement of the flow therapy apparatus.
Figure 12:
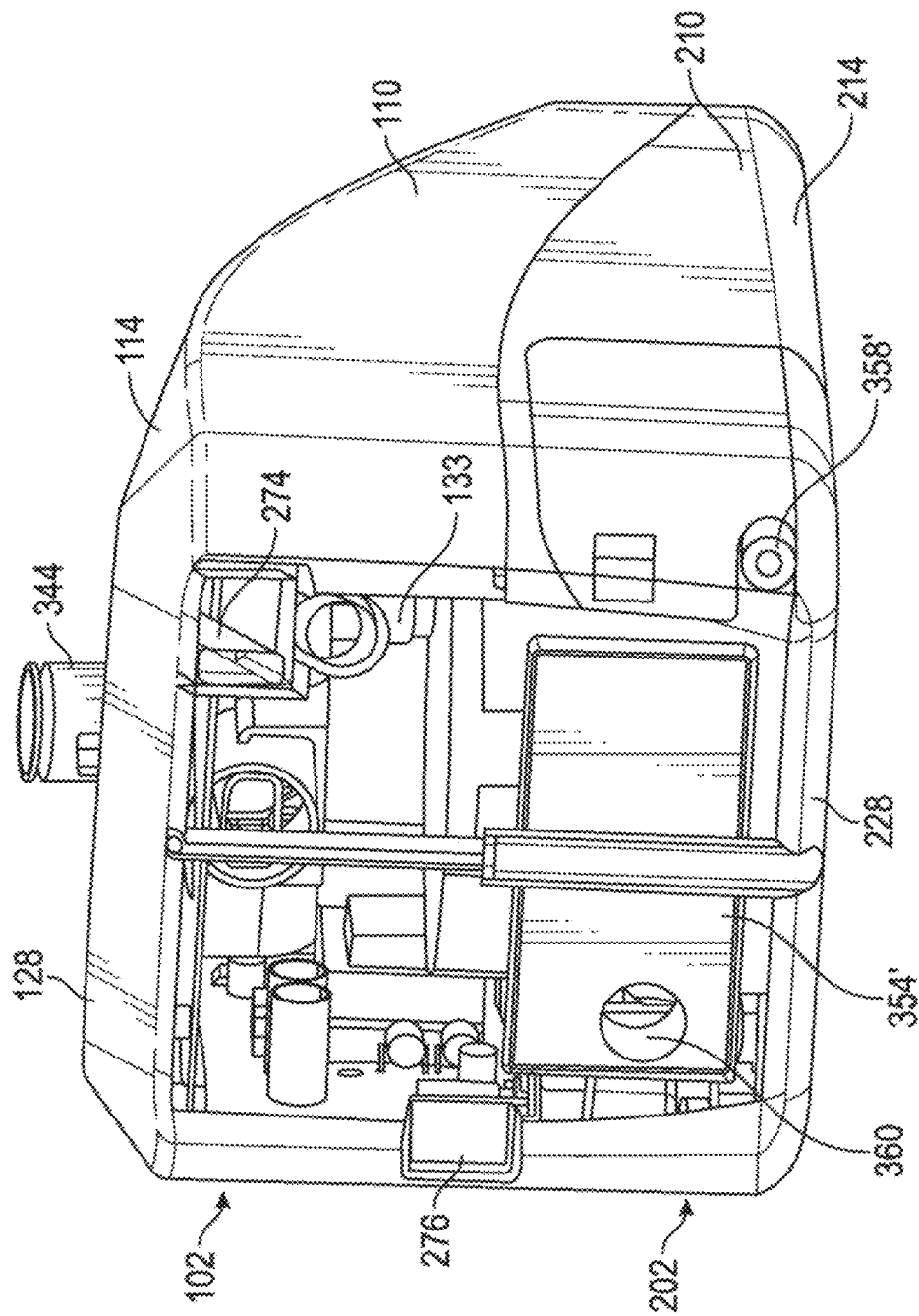
FIG. 12 is a transverse sectional view showing further detail of the air and auxiliary gases inlet arrangement of FIG. 11.
Figure 13:
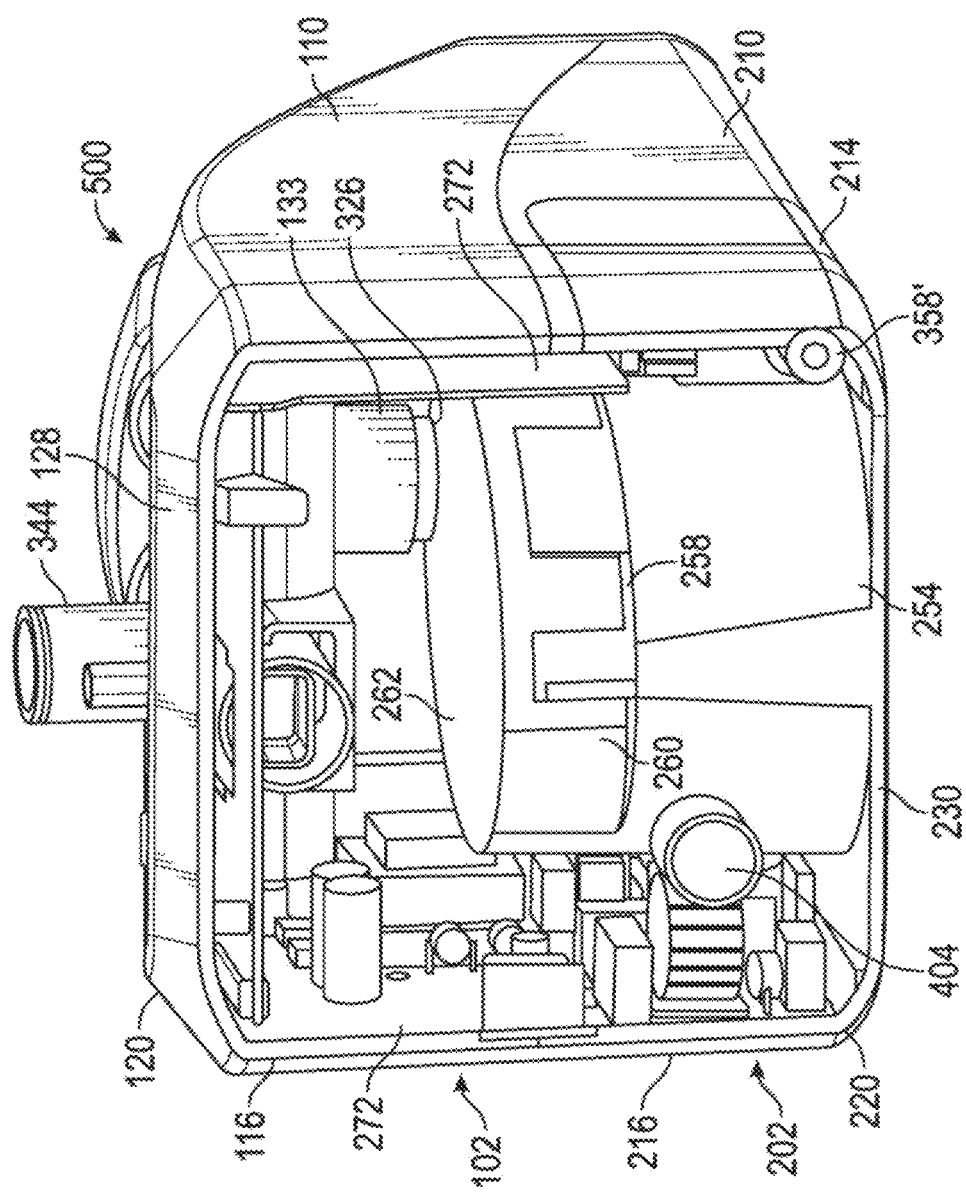
FIG. 13 is another transverse sectional view showing further detail of the air and auxiliary gases inlet arrangement of FIG. 11.
Figure 14:
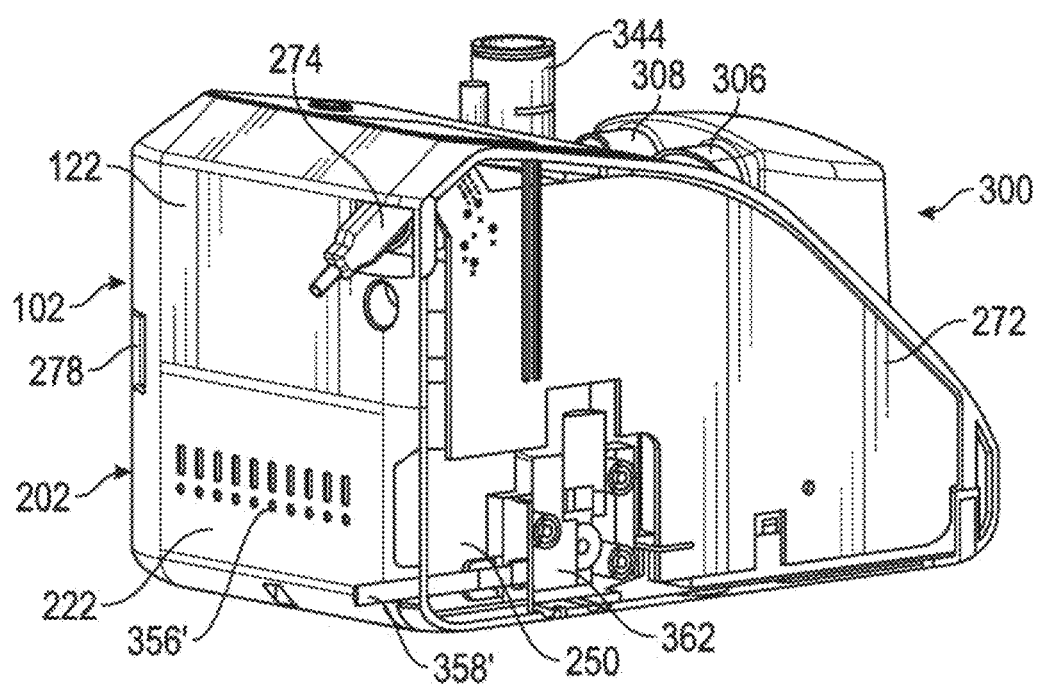
FIG. 14 is a longitudinal sectional view showing further detail of the air and auxiliary gases inlet arrangement of FIG. 11.

The apparatus 10 can have air and oxygen (or alternative auxiliary gas, such as nitrogen) inlets in fluid communication with the motor to enable the motor to deliver air, oxygen, or a suitable mixture thereof to the humidification chamber 300 and thereby to the patient. The apparatus 10 can have one or more inlets for any auxiliary or supplementary gases, including but not limited to oxygen and nitrogen. As shown in FIG. 10, the apparatus 10 may have a combined air/auxiliary gases inlet arrangement 350. This arrangement can include a combined air/auxiliary gases port 352 into the housing 100, a filter 354, and a cover 356 with a hinge 358. A gases tube can also extend laterally or in another appropriate direction and be in fluid communication with one or more auxiliary gases sources. The port 352 can be fluidly coupled with the motor 402. For example, the port 352 may be coupled with the motor and sensor module 400 via a gases flow passage between the port 352 and an inlet aperture or port in the motor and sensor module 400, which in turn would lead to the motor.

The apparatus 10 may have the arrangement shown in FIGS. 11 to 14 to enable the motor to deliver air, auxiliary gases, or a suitable mixture thereof to the humidification chamber 300 and thereby to the patient. This arrangement can include an air inlet 356' in the rear wall 222 of the lower chassis 202 of the housing 100. The air inlet 356' comprises a rigid plate with a suitable grill arrangement of apertures and/or slots. Sound dampening foam may be provided adjacent the plate on the interior side of the plate. An air filter box 354' can be positioned adjacent the air inlet 356' internally in the main housing 100, and include an air outlet port 360 to deliver filtered air to the motor via an air inlet port 404 in the motor and sensor module 400. The air filter box 354' may include a filter configured to remove particulates (for example, dust) and/or pathogens (for example, viruses or bacteria) from the gases flow. A soft seal such as an O-ring seal can be provided between the air outlet port 360 and air inlet port 404 to seal between the components. The apparatus 10 can include a separate auxiliary gases inlet port 358' positioned adjacent one side of the housing 100 at a rear end thereof, the auxiliary gases port 358' for receipt of auxiliary gases from an auxiliary gases source such as a tank or source of piped auxiliary gases. The auxiliary gases inlet port 358' is optionally in fluid communication with a valve 362. The valve 362 can suitably be a solenoid valve that enables the control of the amount of oxygen that is added to the gases flow that is delivered to the humidification chamber 300. The auxiliary gases port 358' and valve 362 may be used with other auxiliary gases to control the addition of other auxiliary gases to the gases flow. The other auxiliary gases may include any one or more of a number of gases useful for gas therapy, including but not limited to heliox and nitric oxide.

As shown in FIGS. 13 to 16, the lower housing chassis 202 can include suitable electronics boards 272, such as sensing circuit boards. The electronics boards can be positioned adjacent respective outer side walls 210, 216 of the lower housing chassis 202. The electronics boards 272 can contain, or can be in electrical communication with, suitable electrical or electronics components, such as but not limited to microprocessors, capacitors, resistors, diodes, operational amplifiers, comparators, and switches. Sensors may be used with the electronic boards 272. Components of the electronics boards 272 (such as but not limited to one or more microprocessors) can act as the controller 13 of the apparatus.

One or both of the electronics boards 272 can be in electrical communication with the electrical components of the apparatus 10, including the display unit and user interface 14, motor, valve 362, and the heater plate 140 to operate the motor to provide the desired flow rate of gases, operate the humidifier 12 to humidify and heat the gases flow to an appropriate level, and supply appropriate quantities of auxiliary gases to the gases flow.

The electronics boards 272 can be in electrical communication with a connector arrangement 274 projecting from the rear wall 122 of the upper housing chassis 102. The connector arrangement 274 may be coupled to a nurse alarm, pulse oximetry port, and/or other suitable accessories. The electronics boards 272 can also be in electrical communication with an electrical connector 276 that can also be provided in the rear wall 122 of the upper housing chassis 102 to provide mains or battery power to the components of the apparatus 10.

As mentioned above, operation sensors, such as flow, temperature, humidity, and/or pressure sensors can be placed in various locations in the flow therapy apparatus 10 and/or the patient conduit 16 and/or cannula 17. The electronics boards 272 can be in electrical communication with those sensors. Output from the sensors can be received by the controller 13, to assist the controller 13 to operate the flow therapy apparatus 10 in a manner that provides optimal therapy, including meeting inspiratory demand.

As outlined above, the electronics boards 272 and other electrical and electronic components can be pneumatically isolated from the gases flow path to improve safety. The sealing also prevents water ingress.

FIGS. 18A-E illustrate another flow therapy apparatus 3010 including a main housing having a main housing upper chassis 3102 and a main housing lower chassis 3202. The flow therapy apparatus 3010 can further include a humidification chamber bay 3108 for receipt of a removable humidification chamber. The flow therapy apparatus 3010 may have any of the features and/or functionality described herein in relation to the flow therapy apparatus 10, but those features are not repeated here for simplicity. Similarly, the features and/or functionality of the flow therapy apparatus 3010 may be used in the other apparatus described herein.

Figure 18A:
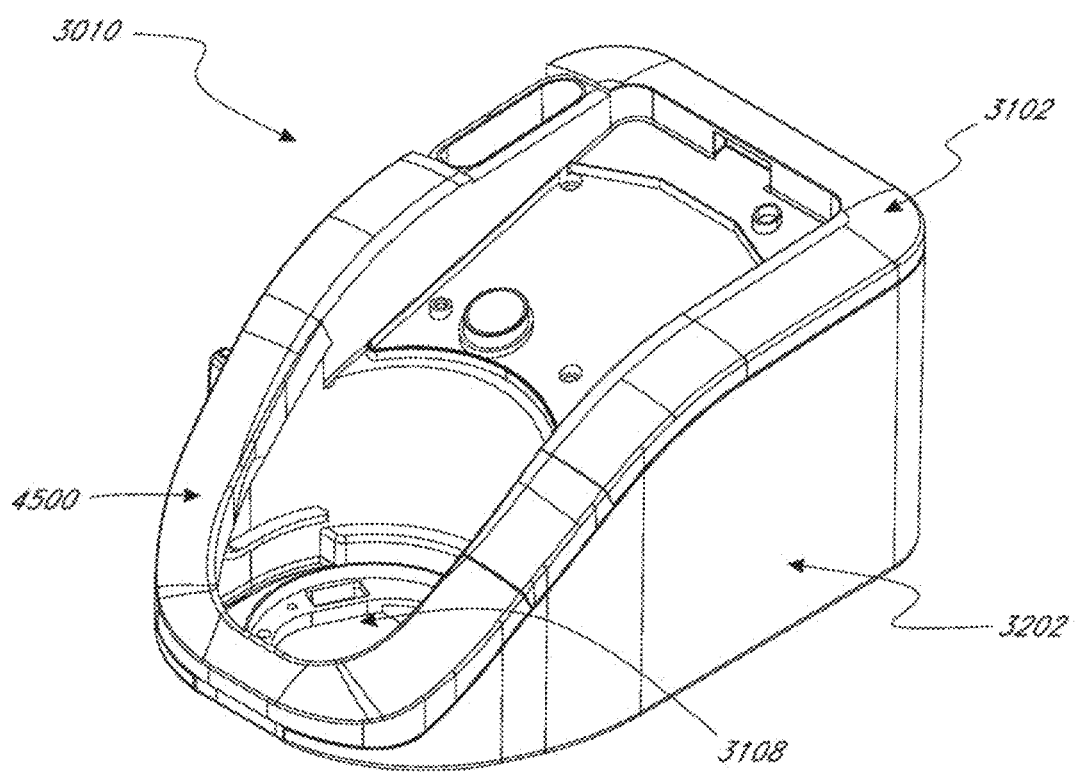
Figure 18C:
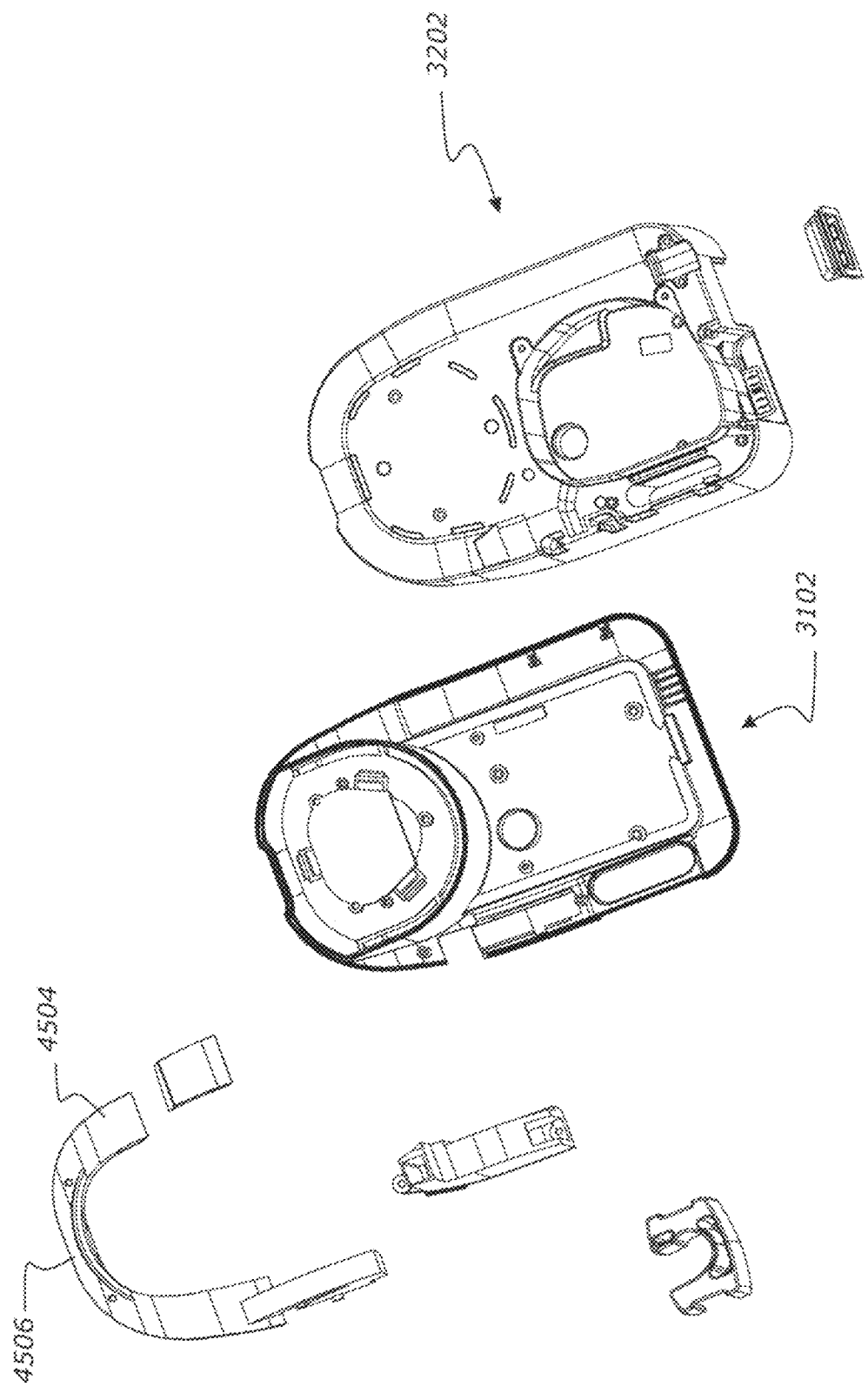
Figure 18D:
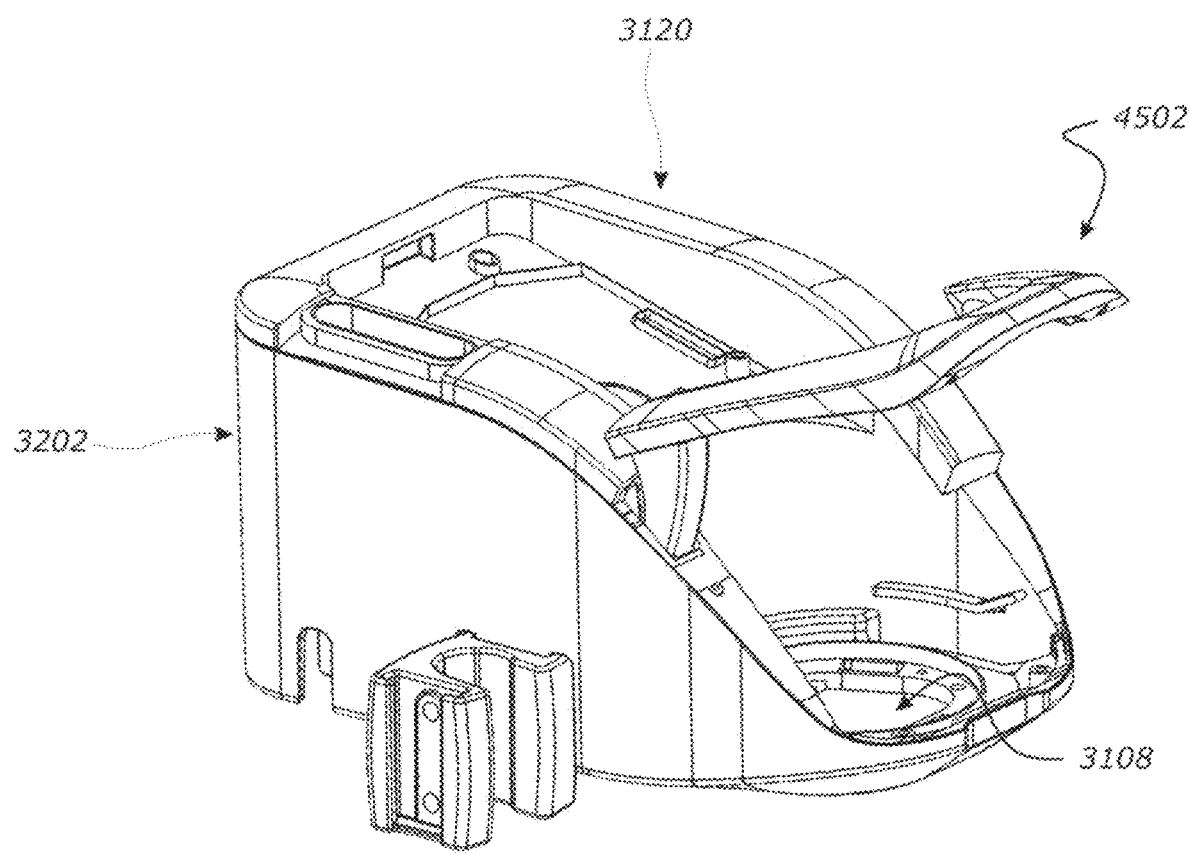

The flow therapy apparatus 3010 can have a single-sided handle/lever 4500. That is, only one side of the handle/lever 4500 is movably connected relative to the main housing of the flow therapy apparatus 3010, whereas there is no pivot connection of the other side of the handle/lever 4500 to the main housing. As shown in FIG. 18D, a left side of the handle/lever 4500 is pivotally connected relative to the main housing. However, it is possible to have only the right side pivotally connected to the main housing. The handle/lever 4500 is pivotally and translationally connected to the main housing, so that the handle/lever 4500 moves on a path having a varying radius relative to the main housing.

A terminal part of the handle/lever 4500 can have a cross-member handle portion 4506 that interconnects forward ends of a left side arm 4502 and a right side member 4504 and forms an engagement region for grasping by a user's fingers. When the handle 4500 is in the raised position as shown in FIG. 18D for example, the cross-member 4506 can act as a carrying handle for the flow therapy apparatus 3010. When the handle is in the fully raised position, the cross member 4506 can be positioned generally above and generally in line with the centre of gravity of the flow therapy apparatus 3010 (including the liquid chamber). The liquid chamber can be inserted into or removed from the humidification chamber bay 3108 when the handle/lever 4500 is raised. When the handle/lever 4500 is in the lowered position, it can inhibit or prevent removal of the liquid chamber from the humidification chamber bay 108.

Figure 18E:
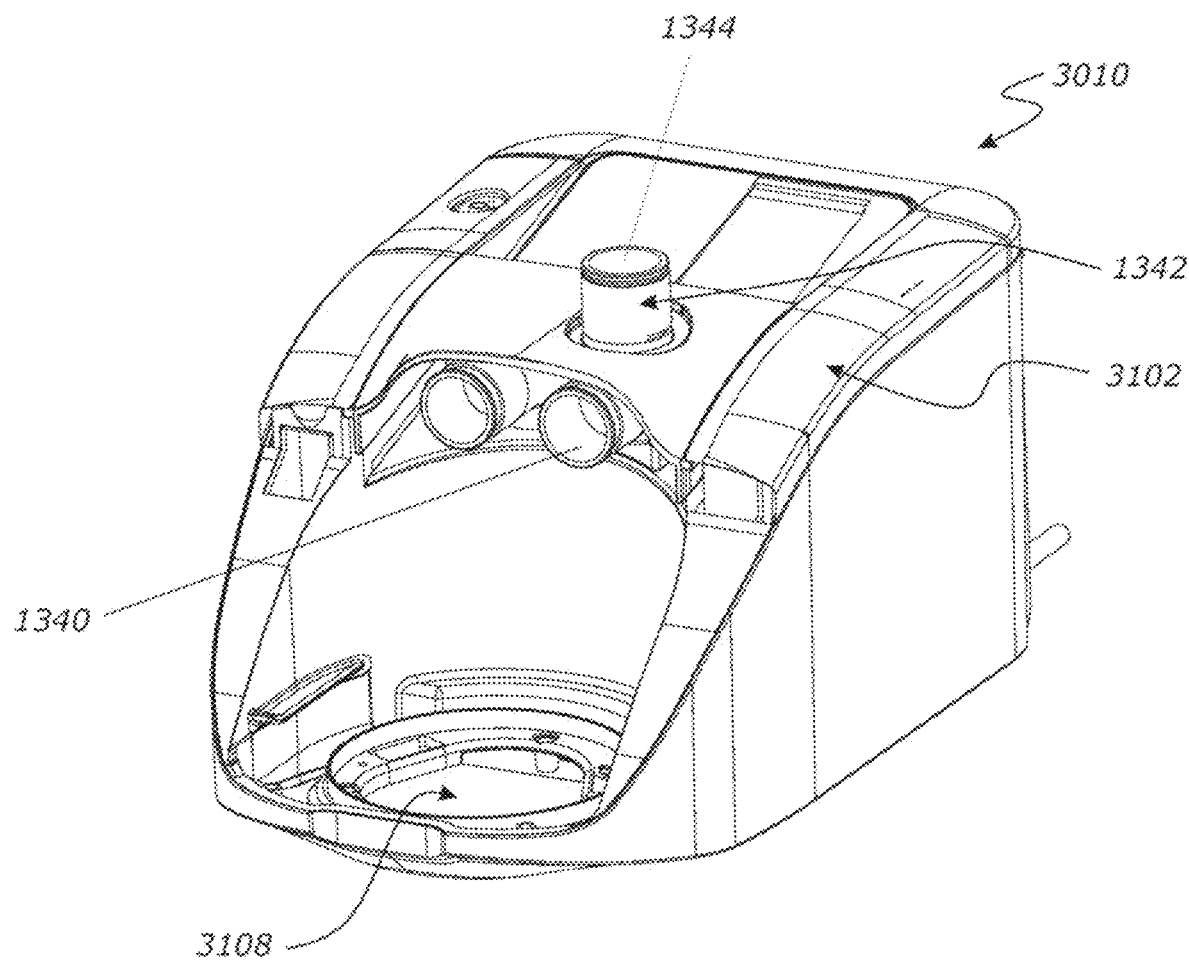

FIG. 18E illustrates the flow therapy apparatus 3010 without the handle/lever. As shown in FIG. 18E, a removable gases flow tube in the form of a removable elbow 1342 can be used in the flow therapy apparatus 3010. The elbow 1342 can receive humidified gases from the liquid chamber at an inlet port 1340 and direct the humidified gases to an outlet port 1344 toward the patient interface through the patient breathing conduit.

Similar to the flow therapy apparatus 10, the lower chassis 3202 of the flow therapy apparatus 3010 can have a motor recess for receiving a motor and sensor module. The motor and sensor module can include a blower, which entrains room air to deliver to a patient. As described above, the blower can be configured to provide a high flow respiratory therapy, a continuous positive airway pressure therapy, or any other respiratory therapies disclosed herein. The gases can be mixed prior to entering the sensor module. The blower can be a mixer for mixing the gases before the gases enter a sensing chamber of the sensor module. The blower can include a separate gas mixer. The separate gas mixer can be positioned before or after the blower. Auxiliary gases can be entrained after the blower and the separate mixer can be used to mix the auxiliary gases and air following entrainment. The controller can increase or decrease a flow rate of the gases flowing through the flow therapy apparatus by controlling a motor speed of the blower.

Control System

Figure 19A:
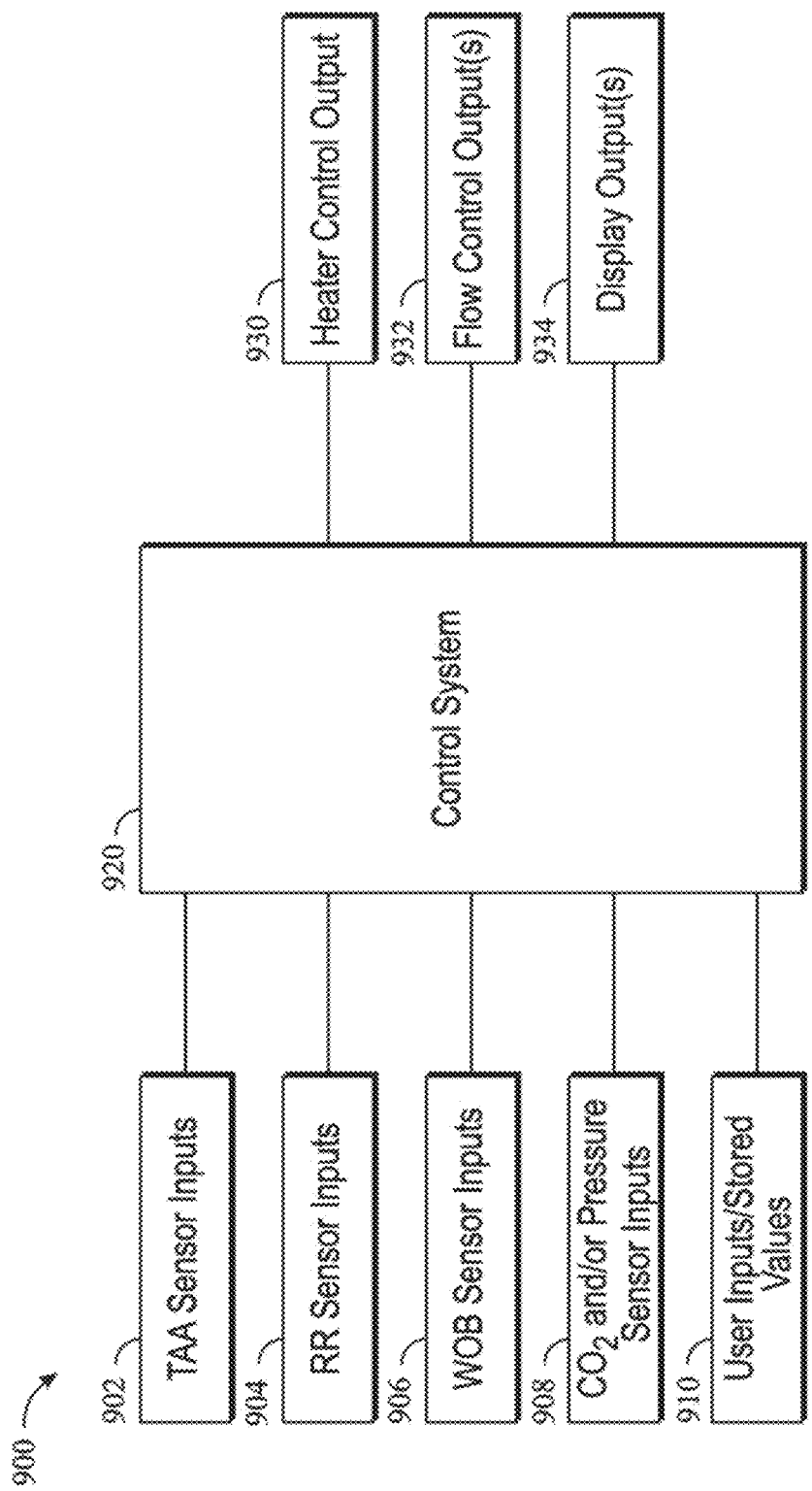
FIG. 19A illustrates a block diagram of a control system interacting with and/or providing control and direction to components of a respiratory assistance system.

FIG. 19A illustrates a block diagram 900 of an example control system 920 that can detect patient conditions and control operation of the flow therapy apparatus including the gas source. The control system 920 can manage a flow rate of the gas flowing through the flow therapy apparatus as it is delivered to a patient. For example, the control system 920 can increase or decrease the flow rate by controlling an output of a motor speed of the blower (hereinafter also referred to as a "blower motor") 930 or an output of a valve 932 in a blender. The control system 920 can automatically determine a set value or a personalized value of the flow rate for a particular patient as discussed below. The flow rate can be optimized by the control system 920 to improve patient comfort and therapy.

The control system 920 can also generate audio and/or display/visual outputs 938, 939. For example, the flow therapy apparatus can include a display and/or a speaker. The display can indicate to the physicians any warnings or alarms generated by the control system 920. The display can also indicate control parameters that can be adjusted by the physicians. For example, the control system 920 can automatically recommend a flow rate for a particular patient. The control system 920 can also determine a respiratory state of the patient, including but not limited to generating a respiratory rate of the patient, and send it to the display.

The control system 920 can change heater control outputs to control one or more of the heating elements (for example, to maintain a temperature set point of the gas delivered to the patient). The control system 920 can also change the operation or duty cycle of the heating elements. The heater control outputs can include heater plate control output(s) 934 and heated breathing tube control output(s) 936.

The control system 920 can determine the outputs 930-939 based on one or more received inputs 901-916. The inputs 901-916 can correspond to sensor measurements received automatically by the controller 600 (shown in FIG. 19B). The control system 920 can receive sensor inputs including but not limited to temperature sensor(s) inputs 901, flow rate sensor(s) inputs 902, motor speed inputs 903, pressure sensor(s) inputs 904, gas(s) fraction sensor(s) inputs 905, humidity sensor(s) inputs 906, pulse oximeter (for example, $SpO_2$) sensor(s) inputs 907, stored or user parameter(s) 908, duty cycle or pulse width modulation (PWM) inputs 909, voltage(s) inputs 910, current(s) inputs 911, acoustic sensor(s) inputs 912, power(s) inputs 913, resistance(s) inputs 914, $CO_2$ sensor(s) inputs 915, and/or spirometer inputs 916. The control system 920 can receive inputs from the user or stored parameter values in a memory 624 (shown in FIG. 19B). The control system 920 can dynamically adjust flow rate for a patient over the time of their therapy. The control system 920 can continuously detect system parameters and patient parameters. A person of ordinary skill in the art will appreciate based on the disclosure herein that any other suitable inputs and/or outputs can be used with the control system 920.

Controller

Figure 19B:
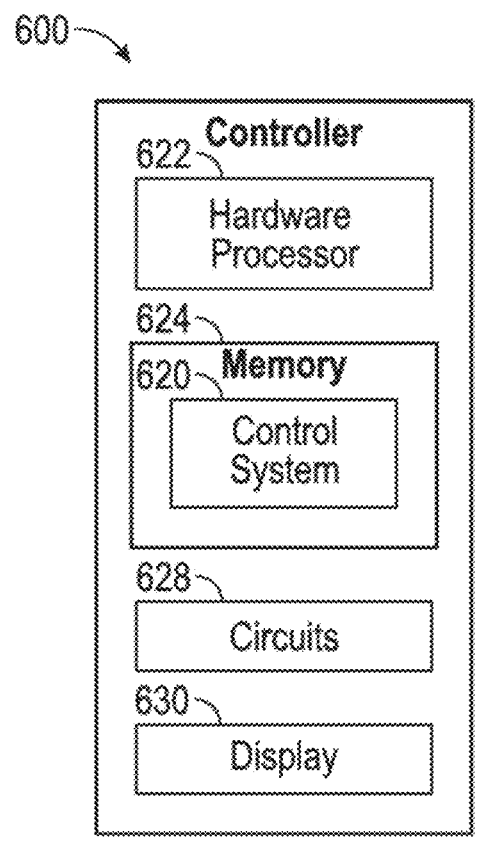
FIG. 19B illustrates a block diagram of an example controller.

FIG. 19B illustrates a block diagram of an embodiment of a controller 600. The controller 600 can include programming instructions for detection of input conditions and control of output conditions. The programming instructions can be stored in a memory 624 of the controller 600. The programming instructions can correspond to the methods, processes and functions described herein. The programming instructions can be executed by one or more hardware processors 622 of the controller 600. The programming instructions can be implemented in C, C++, JAVA, or any other suitable programming languages. Some or all of the portions of the programming instructions can be implemented in application specific circuitry 628 such as ASICs and FPGAs.

The controller 600 can also include circuits 628 for receiving sensor signals. The controller 600 can further include a display 630 for transmitting status of the patient and the respiratory assistance system. The display 630 can also show warnings. The display 630 can be configured to display characteristics of sensed gas(es) in real time. The controller 600 can also receive user inputs via the user interface such as display 630. The user interface may alternatively or additionally comprise buttons or a dial. The user interface may alternatively or additionally comprise a touch screen.

Motor and Sensor Module

Any of the features of the flow therapy apparatus described herein, including but not limited to the humidifier, the flow generator, the user interface, the controller, and the patient breathing conduit configured to couple the gases flow outlet of the respiratory system to the patient interface, can be combined with any of the sensor modules described herein.

Figure 20:
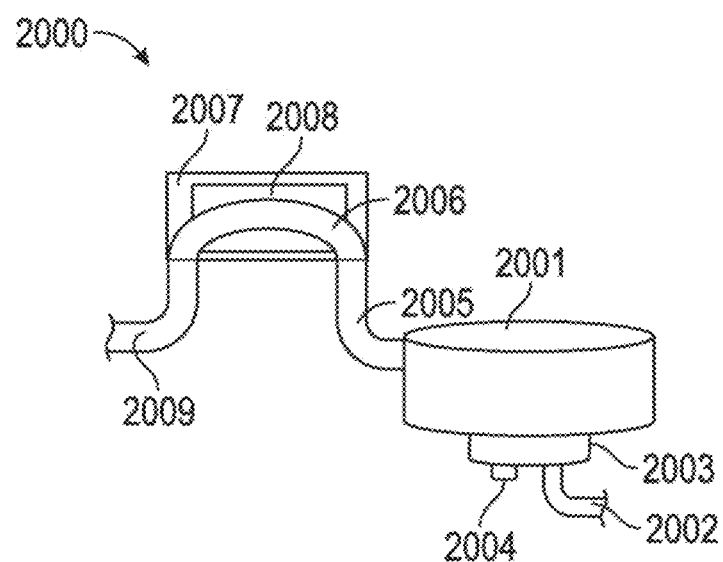
FIG. 20 illustrates a block diagram of a motor and sensor module.

FIG. 20 illustrates a block diagram of the motor and sensor module 2000, which is received by the recess 250 in the flow therapy apparatus (shown in FIGS. 17A and 17B). As described above, the module can also comprise a sensor module without the motor inside the module. The motor and sensor module can include a blower 2001, which entrains room air to deliver to a patient. The blower 2001 can be a centrifugal blower.

Room air can enter a room air inlet 2002, which enters the blower 2001 through an inlet port 2003. The inlet port 2003 can include a valve 2004 through which a pressurized gas may enter the blower 2001. The valve 2004 can control a flow of auxiliary gases into the blower 2001. The valve 2004 can be any type of valve, including a proportional valve or a binary valve. In some embodiments, the inlet port does not include a valve.

The blower 2001 can operate at a motor speed of greater than 1,000 RPM and less than 30,000 RPM, greater than 2,000 RPM and less than 21,000 RPM, or between any of the foregoing values. Operation of the blower 2001 mixes the gases entering the blower 2001 through the inlet port 2003. Using the blower 2001 as the mixer can decrease the pressure drop that would otherwise occur in a system with a separate mixer, such as a static mixer comprising baffles, because mixing requires energy.

The mixed air can exit the blower 2001 through a conduit 2005 and enters the flow path 2006 in the sensor chamber 2007. A sensing circuit board with sensors 2008 can positioned in the sensor chamber 2007 such that the sensing circuit board is at least partially immersed in the gases flow. At least some of the sensors 2008 on the sensing circuit board can be positioned within the gases flow to measure gas properties within the flow. After passing through the flow path 2006 in the sensor chamber 2007, the gases can exit 2009 to the humidification chamber.

Positioning sensors 2008 downstream of the combined blower and mixer 2001 can increase accuracy of measurements, such as the measurement of gases fraction concentration, including but not limited to oxygen concentration, over systems that position the sensors upstream of the blower and/or the mixer. Such a positioning can give a more repeatable flow profile. Further, positioning the sensors downstream of the combined blower and mixer avoids the pressure drop that would otherwise occur, as where sensing occurs prior to the blower, a separate mixer, such as a static mixer with baffles, is required between the inlet and the sensing system. The mixer can introduce a pressure drop across the mixer. Positioning the sensing after the blower can allow the blower to be a mixer, and while a static mixer would lower pressure, in contrast, a blower increases pressure. Also, immersing at least part of the sensing circuit board and sensors 2008 in the flow path can increase the accuracy of measurements because the sensors being immersed in the flow means they are more likely to be subject to the same conditions, such as temperature and pressure, as the gases flow and therefore provide a better representation of the gas characteristics.

Figure 21:
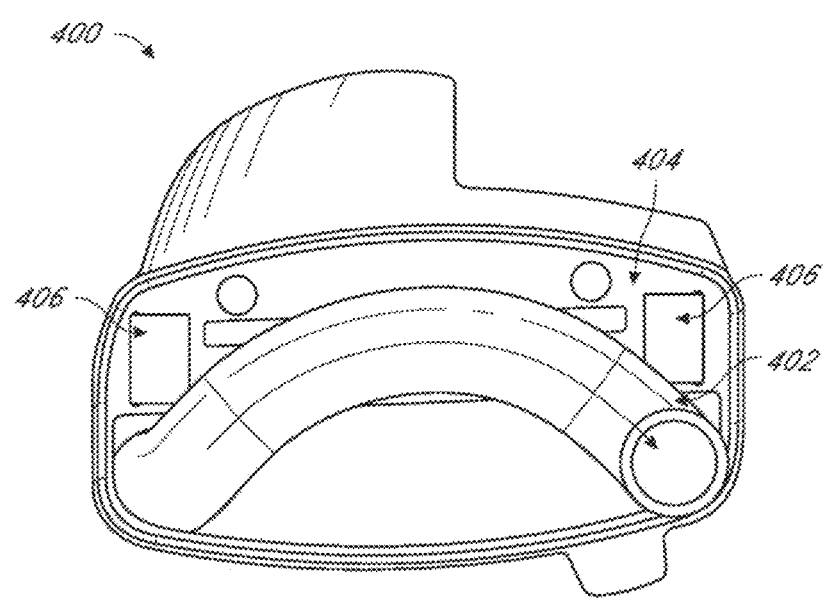
FIG. 21 illustrates a sensing chamber of an example removable motor and sensor module.

Turning to FIG. 21, the gases exiting the blower can enter a flow path 402 in the sensor chamber 400, which can be positioned within the motor and sensor module. The flow path 402 can have a curved shape. The flow path 402 can be configured to have a curved shape with no sharp turns. The flow path 402 can have curved ends with a straighter section between the curved ends. A curved flow path shape can reduce pressure drop in a gases flow without reducing the sensitivity of flow measurements by partially coinciding a measurement region with the flow path to form a measurement portion of the flow path, which will be described below with reference to FIGS. 23A-23B.

A sensing circuit board 404 with sensors, such as ultrasonic transmitters, receivers, humidity sensor, temperature sensor, flow rate sensor, and the like, can be positioned in the sensor chamber 400 such that the sensing circuit board 404 is at least partially immersed in the flow path 402. Immersing at least part of the sensing circuit board and sensors in the flow path can increase the accuracy of measurements because the sensors immersed in the flow are more likely to be subject to the same conditions, such as temperature and pressure, as the gases flow, and therefore provide a better representation of the characteristics of the gases flow. After passing through the flow path 402 in the sensor chamber 400, the gases can exit to the humidification chamber.

With continued reference to FIG. 21, openings 406 of the sensor chamber 400 can hold acoustic transmitters (shown as 1502 in FIG. 22A), such as ultrasonic transducers which form an acoustic axis (shown as 1520 in FIG. 22B and 1620 in FIGS. 23A-23B) along at least a portion of the flow path 402 to measure properties or characteristics of the gases within the flow. The ultrasonic transducers can act as both transmitters and receivers.

Ultrasonic Sensing with Separate Acoustic Receivers

Turning to FIG. 22A, an example sensing circuit board 1500 with acoustic transmitters and separate acoustic receivers is shown. The sensing circuit board 1500 can be a printed circuit board (PCB). At least a portion of the sensing circuit board, including but not limited to the circuit 1510, can be mounted outside of the flow path 402 bound by dotted lines 1512.

The sensing circuit board 1500 can include one or more acoustic transmitters 1502, one or more acoustic receivers 1504, and one or more of additional sensors, such as sensor 1508. The one or more acoustic transmitters 1502 can be ultrasonic transmitters. Examples of the additional sensors can include a flow rate sensor, a humidity sensor, including a humidity sensor to be used with a separate temperature sensor and a combined humidity and temperature sensor, a sensor for measuring barometric pressure, a sensor for measuring differential pressure, and/or a sensor for measuring gauge pressure. The acoustic transmitters 1502 in FIG. 22A can be first and second ultrasonic transducers. The first and second acoustic transducers can be a matched pair of ultrasonic transducers, for example, a matched pair of piezoelectric transducers. The acoustic transmitters 1502 can include one or more "closed frame" piezoelectric transducers. Closed-frame transducers generate a lower amplitude acoustic signal resulting in a lower signal to noise ratio, but are more reliable and less prone to failure. They are also less susceptible to water ingress. The acoustic transmitters 1502 can be tuned to resonate in the range of about 20 kHz to about 80 kHz, or about 20 kHz to 30 kHz, or about 30 kHz to about 70 kHz, or about 30 kHz to about 50 kHz. The acoustic transmitters 1502 can be tuned to resonate at about 25 kHz or alternatively about 40 kHz, which can make it easier to filter out acoustic noise at lower frequencies, such as noise from flow of gases.

The acoustic receivers 1504 can include microphones, such as condenser microphones, electret microphones, and MEMS microphones. The microphones can have small time/phase delays and relatively linear and flat frequency responses. The MEMS microphones can be small in size. The MEMS microphones can be less than about 5 mm on any dimension. The receivers can also be other types of receivers, such as piezoelectric transducers, carbon microphone, and fiber optic sensors. Where a piezoelectric transducer is used only as a receiver, its receiving function may be decoupled from the transducer's transmitting function such that it is not a transmitter, and where a piezoelectric transducer is used only as a transmitter, its transmitting function may be decoupled from the transducer's receiving function such that it is not a receiver. Thus, the same transducer is not used as a transmitter and receiver.

Piezoelectric transducers can be used as the transmitters and microphones can be used as the receivers. The piezoelectric transducers can have closed-frame. The combination of closed-frame piezoelectric transducers and microphones can have an improved signal-to-noise ratio compared with the combination of two closed-frame piezoelectric transducers each acting as both a transmitter and receiver, because the microphones are more sensitive to the acoustic signal than the closed-frame piezoelectric transducers acting as receivers. Although the types of receivers disclosed above can all be used to reduce or eliminate delays, the microphones have an additional advantage over piezoelectric transducers, which is reduction of the size of the receiver.

As shown in FIG. 22A, the acoustic transmitters 1502 can be positioned on opposite ends of the sensing circuit board 1500 and near opposite ends of the flow path 402 bound by the dotted lines 1512. The acoustic transmitters 1502 can be positioned external to the flow path 402, and transmit the signal through a wall of the sensing chamber. The ultrasonic transmitters can be covered with a plastic cover or an acoustically matched covering plate. This arrangement can provide the advantage that the ultrasonic transmitters are not exposed to oxygen. However, this arrangement can also add acoustic impedance which must be accounted for, or distortion of the waves. The acoustic transmitters 1502 can be configured to transmit acoustic signals, such as ultrasonic signals or pulses. The acoustic transmitters 1502 can be configured to both transmit and receive acoustic signals, such as ultrasonic pulses. The acoustic signals can travel bi-directionally between the two acoustic transmitters 1502. That is, a first one of the acoustic transmitters 1502 can transit acoustic signals to be received by a second one of the acoustic transmitters 1502, and the second one of the acoustic transmitters 1502 can transit acoustic signals to be received by the first one of the acoustic transmitters 1502. The acoustic transmitters 1502 can face each other along an acoustic axis 1520 (1620 in FIG. 23A). Also as shown in FIG. 22A, the acoustic receivers 1504 can be positioned on extended arms 1506 of the sensing circuit board 1500 and be positioned in the flow path 402. This way, the hardware processor can be configured to estimate a temperature of the acoustic receivers 1504 to be at the same temperature or at a similar temperature as a measured temperature of gases in the flow path 402. Additional sensors, such as a temperature sensor, a humidity sensor or a flow rate sensor, can be placed along the extended arms 1506 or at other locations on the sensing circuit board 1500.

Figure 22B:
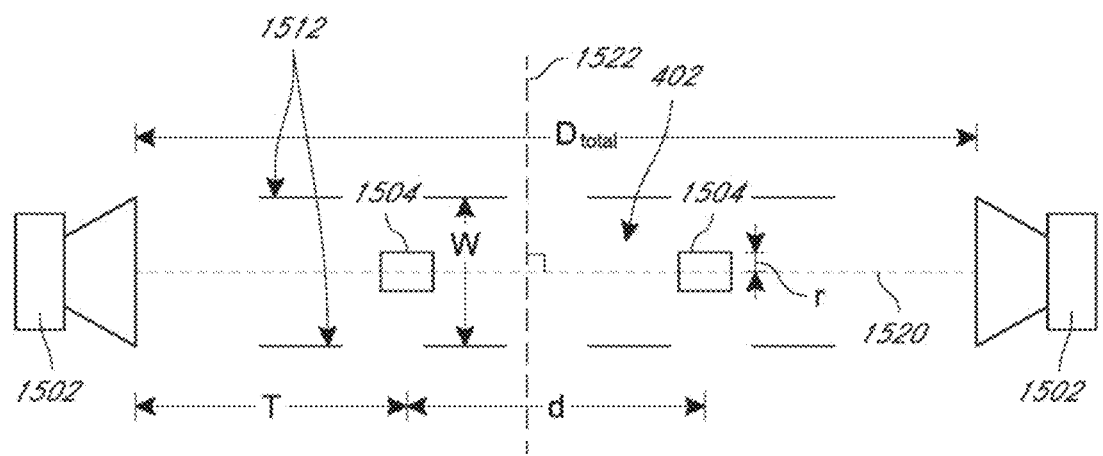
FIG. 22B is a schematic illustration of positioning and distances between the transmitters and/or receivers.

Turning to FIG. 22B, which is a simplified illustration of the sensing circuit board described above, the acoustic receivers 1504 can be centered on the acoustic axis 1520 (also shown as 1620 in FIG. 23A) of the narrow beam-angle acoustic transmitter 1502 and along a midline or central axis of the flow path (shown as 1610 in FIG. 23A) so as to avoid interference and reflections. The acoustic receivers 1504 can be spaced as far apart as allowed by the positioning of the acoustic transmitters 1502. One acoustic receiver 1504 can be downstream of the other acoustic receiver 1504. The acoustic receivers 1504 can also be placed as far apart as allowed by the geometry of the flow path 402 (bound by the dotted lines 1512) and also be positioned within a portion of the flow path 402 that overlaps with an acoustic path that signal(s) of the acoustic transmitters 1502 can travel (described in greater detail below with reference to FIGS. 23A-23B). A large distance between the acoustic receivers 1504 can provide a greater level of flow sensitivity by having a smaller percentage error in the time of flight measurement(s). However, the acoustic receivers 1504 can also be positioned at a sufficient distance from the ultrasonic transmitters 1502 to mitigate near-field effects. The acoustic receivers 1504 can be centered on the acoustic axis 1520, along the midline of the flow path, and sufficiently far apart from each other to increase accuracy of measurements of the characteristics of the gases flow, and be sufficiently spaced away from the nearest acoustic transmitter 1502 to mitigate near-field effects. The acoustic receivers 1504 may be centered on the acoustic axis 1520, but not along the midline of the flow path. The acoustic receivers 1504 may be positioned along the midline of the flow path but not be centered on the acoustic axis 1520.

Also as shown in FIG. 22B, the flow path 402 can have a total distance $D_{total}$ between pulse-emitting surfaces of the acoustic transmitters 1502. The total distance $D_{total}$ is also illustrated in FIG. 22A. The flow path 402 can have a total distance $D_{total}$ of between about 50 mm and about 200 mm, between about 70 mm and about 150 mm, between about 80 mm and 120 mm, or about 95 mm.

As illustrated in FIG. 22B, the section of the flow path 402 between the ultrasonic transmitters can substantially overlap with the acoustic path travelled by the ultrasonic pulse between the transmitters. The flow path 402 between the ultrasonic transmitters can also have a total flow distance of between about 40 mm to about 150 mm, about 60 mm and about 100 mm, or between about 70 mm and about 90 mm, or about 75 mm.

As shown in FIG. 22B, the flow path 402 can have a diameter W between the boundaries 1512. W can be between about 10 and about 40 mm, between about 12 mm and about 30 mm, or about 15 mm to 25 mm, or about 16 mm.

FIG. 22B also illustrates d, the distance between the acoustic receivers 1504. The distance d between the acoustic receivers 1504 can be between about 30 mm and about 150 mm, or about 55 mm. FIG. 22B also illustrates T, which is the distance between the acoustic transmitter 1502 and nearest acoustic receiver 1504. The distance between the acoustic transmitter 1502 and nearest acoustic receiver 1504 can be between about 10 mm and about 40 mm, or about 20 mm. The positioning of the ultrasonic transducers and receivers can be symmetrical about an axis 1522, which is perpendicular to the central axis 1520 of the acoustic path.

The acoustic receivers 1504 can be located slightly above or below the central axis 1520 by a distance r, but are still located within the flow path. The off-axis distance r can be between about 0 mm to about 5 mm. The acoustic receivers 1504 can be located on the central axis of the acoustic path, having an off-axis distance r of 0 mm.

The separate receivers can provide several advantages. Specifically, an ultrasonic sensing configuration with transducers acting as both the transmitter and receiver can only generate one measurement of the signal per direction, but having two receivers in the system can generate two measurements per direction, making it easier to detect an edge and/or wave deformations as the waveforms received at each receiver are expected to be the same. Also, having two waveforms that are expected to be the same, but delayed, can make other methods of edge detection substantially more effective. The two waveforms can be recorded with a fast Analog Digital Converter (ADC) and a cross correlation can be performed between these two waveforms. Although cross-correlation is more computationally expensive than edge detection, the resulting measurement can be more precise and robust against noise, and eliminates the "windowing" problem present with edge detection since the entire waveform is being compared. This places less constraint on the distances between the sensors, the frequencies used, and the range of speed of sounds that can be measured. Microphones may also age better than ultrasonic transducers by continuing to receive a reliable signal for a long period of time.

The small size of the acoustic receivers 1504 can allow them to be mounted directly within or just to a side of the gases and acoustic paths. Being mounted within the gases flow or just to the side of the gases flow means the hardware processor can estimate the temperature of the receivers to be the same as the gas temperature, allowing for any temperature corrections to be made more accurately. Receivers such as microphones can come in surface mount device (SMD) packages, allowing them to be mounted directly on a PCB with a well-defined distance between them. As only this distance is relevant to a differential sensor's operation (described in greater detail below), measurements of the characteristics of the gases flow are more stable than relying on the mounting of two piezoelectric transducers. Another advantage of being able to mount the receivers in the flow is the reduction or elimination of "dead space," which is a region in front of each transmitter where there is no gases flow. The dead space can introduce cross terms between velocity and speed of sound, and complicate the computations. The receivers can be mounted far enough ahead of the transmitters to eliminate dead spaces.

Figure 23A:
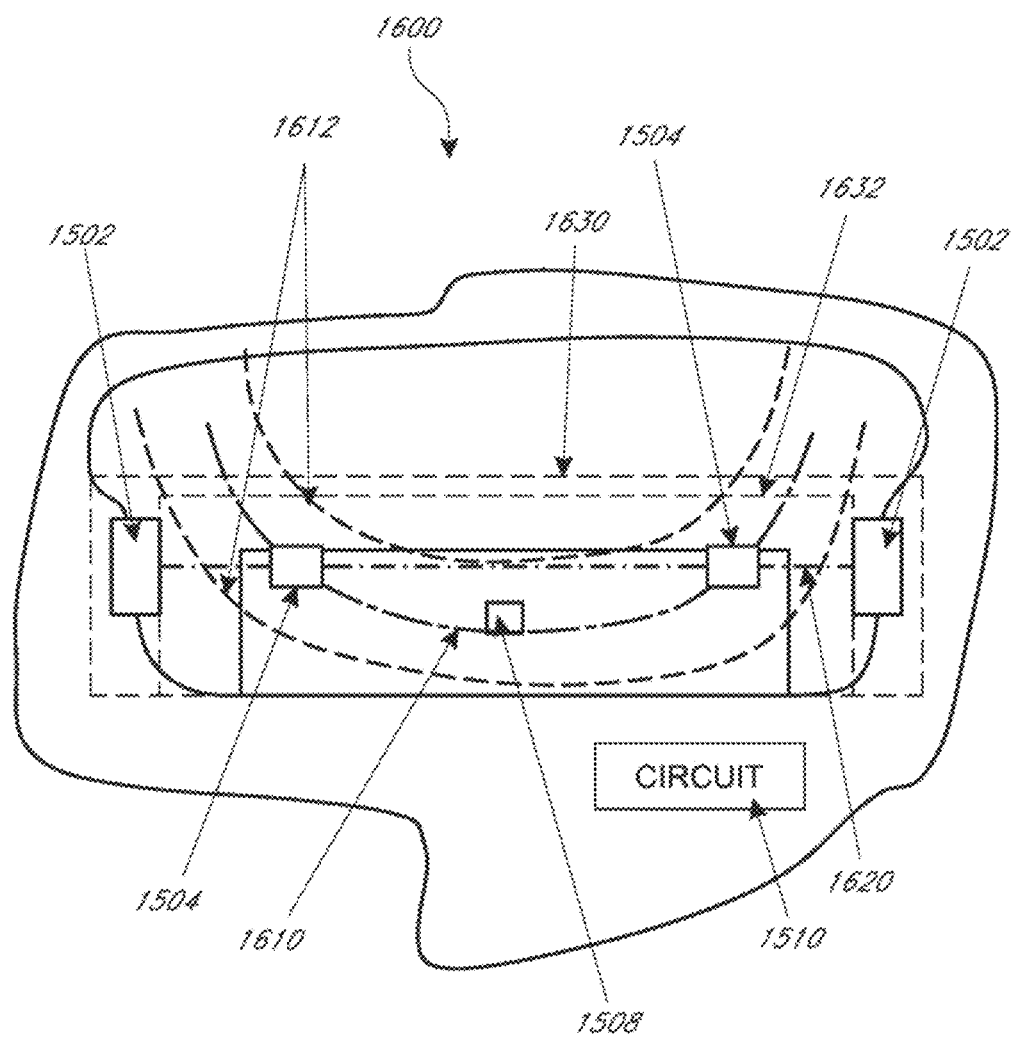
FIGS. 23A-B are schematic illustrations of ultrasonic sensing with two transmitters and two separate receivers on an example sensing circuit board.
Figure 23B:
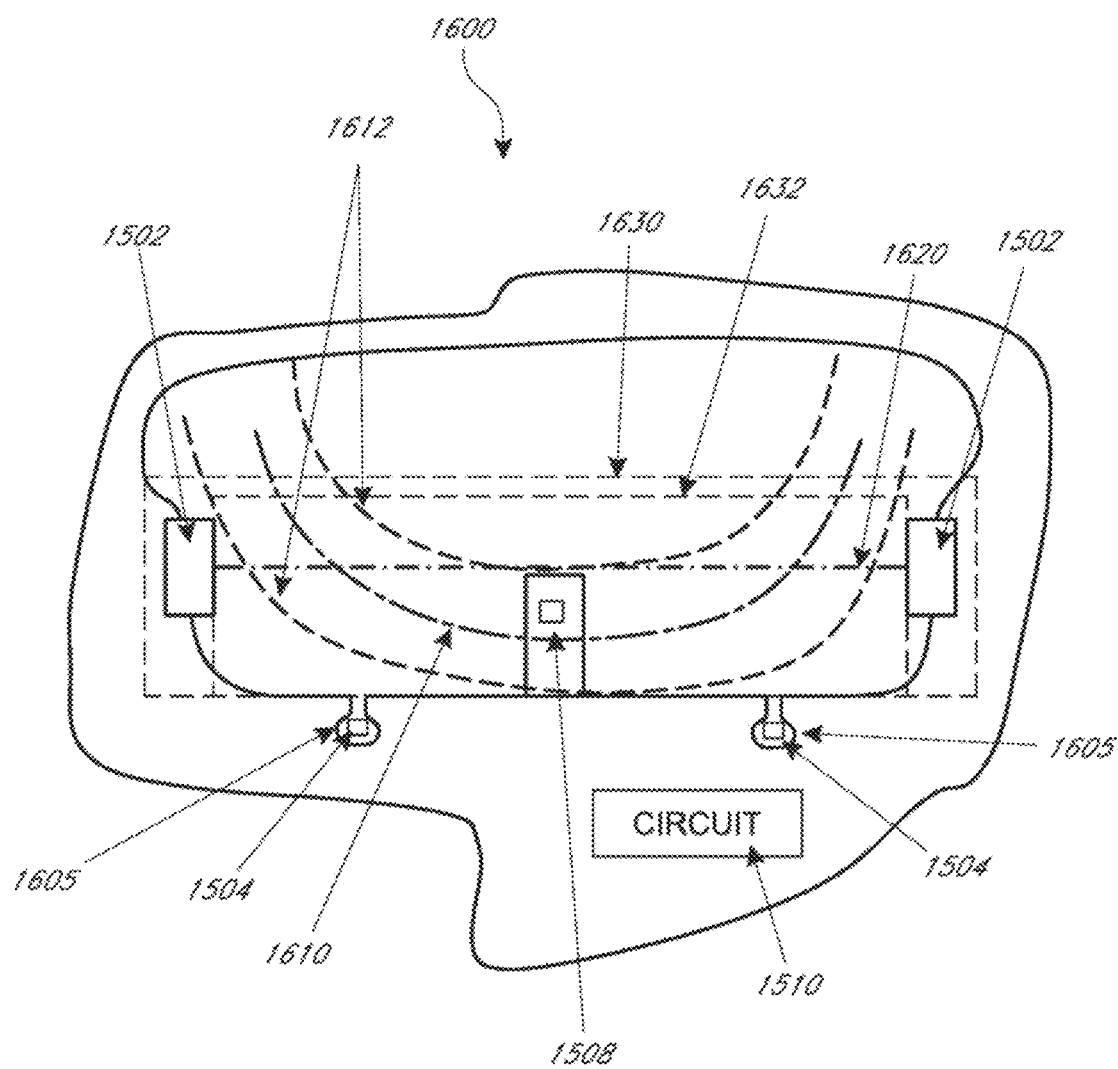

Additional details of the positioning of the ultrasonic transmitters and receivers with reference to different regions of the sensing circuit board will now be described with reference to FIGS. 23A-23B. Various regions of the sensing circuit board are illustrated in FIGS. 23A-23B, and can be incorporated into the sensing circuit boards disclosed elsewhere in the application. As shown in FIGS. 23A-23B, a sensing region 1630 can be a region in which the acoustic sensors, for example, the ultrasonic transmitters and/or receivers, are located. Within the sensing region 1630, a measurement region 1632 can be a region in which ultrasonic signals can propagate through gases and are received for purpose of measuring the characteristics of the gases flow. The measurement region 1632 can be between two ultrasonic transmitters, or between an ultrasonic transmitter and a reflecting surface. A portion of the flow path that is within the measurement region is defined as a measurement portion of the flow path. Although the flow of gases generally follows the flow path, some gases can flow to other parts of the sensing chamber and accumulate in dead spaces.

As shown in FIG. 23A, the sensing circuit board 1600 can have the acoustic receivers 1504 positioned within the flow path bound by the dotted lines 1612. Features of the sensing circuit board 1500 described above and illustrated in FIGS. 22A-22B can be incorporated into the sensing circuit board 1600 illustrated in FIGS. 23A-23B unless otherwise described. As shown in FIG. 23A, a first acoustic transmitter 1502 and a second acoustic transmitter 1502 can be mounted near either end of the flow path bound by the dotted lines 1612 on the sensing circuit board 1600. The first and second acoustic transmitters 1502 can be a matched pair of acoustic transmitters, such as ultrasonic transducers. The first and second acoustic transmitters 1502 can be positioned substantially at or near each end of the measurement portion of the gases flow path. The acoustic transmitters 1502 can be piezoelectric transducers. Two acoustic receivers 1504 can be mounted directly within the measurement portion of the gases flow path and between the two acoustic transmitters 1502. As further shown in FIG. 23A, the acoustic transmitters 1502 can face along a midline 1610 of the flow path. The acoustic receivers 1504 can be centered on the midline 1610 or slightly offset from the midline 1610 as shown in FIG. 23B and as described above with reference to the distance r in FIG. 22B. A temperature sensor 1508 can be located on the same sensing circuit board 1600 and also directly within the flow path. The temperature sensor 1508 may also be a humidity sensor, pressure sensor, or the like. There may be a humidity or pressure sensor located elsewhere in the apparatus. The gases flow can travel through the sensing region 1630.

FIG. 23B illustrates a variation of the sensing circuit board 1600 of FIG. 23A and incorporates features of the sensing circuit board 1600 of FIG. 23A except as noted below. In FIG. 23B, the acoustic receivers 1504 are positioned to the side of the flow path defined by the flow path boundaries 1612 and to the side of the sensing region 1630. The acoustic receivers 1504 can be placed with ports 1605 located to the side of the sensing region 1630 to allow the acoustic signal to be sensed. The ports 1605 can maintain a pneumatic connection between the acoustic receivers 1504 and the flow path. This arrangement can allow the acoustic noise due to flow to be greatly reduced, and thus can alleviate problems in filtering out the acoustic noise. The operation otherwise can remain the same as shown in FIG. 23A, since any delay caused by having the receivers to the side is absorbed into the transducer delays and cancelled by the differential sensing, which will be described in greater detail below.

The acoustic transmitters 1502 and acoustic receivers 1504 can measure characteristics of the gases flow, such as gases concentration including but not limited to oxygen concentration and flow rate. To calculate the flow rate of gases moving through the sensing chamber, the transmitters can each emit a signal so that there is a signal in both directions along the axis 1620 of the acoustic path. Further, to determine a particular gas concentration, for example but not limited to oxygen concentration, only signals in a single direction are necessary. To determine flow rate, signals in both directions may be necessary. The additional sensors can also be used for determining the characteristics of the gases flow, such as temperature, pressure, flow rate, humidity, and the like. In addition, the acoustic transmitters 1502 and acoustic receivers 1504 and the additional sensors can provide redundancy in measurements of the characteristics of the gases flow, such that the flow therapy apparatus can still monitor the characteristics of the gases flow despite failure of some of the sensors. For example, if one of the receivers and/or transducers fails, there is redundancy due to the plurality of transmitters and/or receivers, which can allow the hardware processor to still determine the characteristics of the gases flow (described in greater detail below). The hardware processor can also be configured to use outputs of the one or more of the additional sensors to provide corrections to calculation of a characteristic of the gases flow, such as flow rate. For example, flow readings taken from a different flow rate sensor other than the ultrasonic sensors can be used to compute or adjust a calibration parameter of the ultrasonic sensors including ultrasonic transmitters and/or receivers, thereby continuously correcting any error or drift in the ultrasonic transmitters' and/or receivers' reading. The different flow rate sensor can comprise a heated temperature sensing element configured to measure flow rate.

Two Acoustic Transmitters/Two Acoustic Receivers Configuration

Figure 24A:
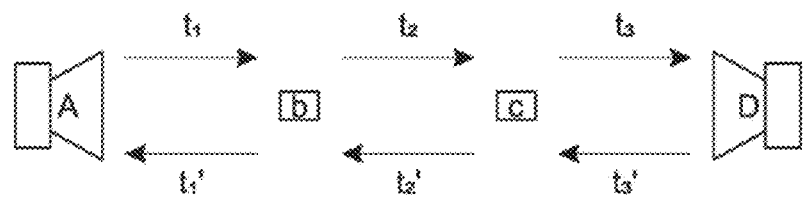
FIGS. 24A-D are schematic illustrations of various examples of ultrasonic sensing configuration with separate receivers.

Delay cancelation in the configuration shown in FIGS. 22A-B and 23A-B, that is, with two acoustic transmitters and two acoustic receivers, are described below with respect to FIG. 24A, which shows a simplified illustration of the system described above, and FIG. 25. FIG. 24A shows two acoustic transmitters, A, D, with two acoustic receivers, b, c, located between the two transmitters, A, D. An acoustic signal is propagated in each direction by the acoustic transmitters, A, D respectively. Additional sensors are omitted in FIGS. 24A-D for clarity.

Figure 25:
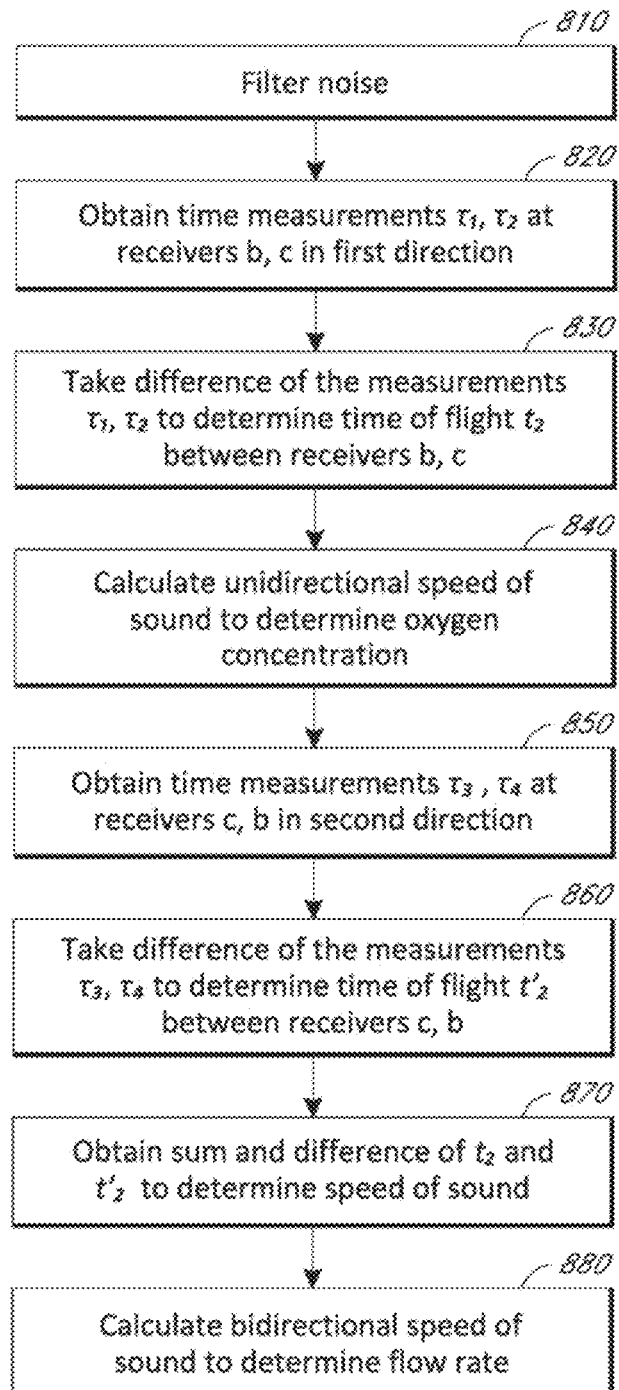
FIG. 25 is a flow chart illustrating determining characteristics of the gases flow.

FIG. 25 illustrates how an example controller or hardware processor can determine characteristics of the gases flow. As shown in the flowchart in FIG. 25, the hardware processor can obtain the following time measurements $\tau_1, \tau_2$ at the two acoustic receivers, b, c, in the first direction (where A is transmitting) at step 820:

$$\tau_1 = A + t_1 + b$$

$$\tau_2 = A + t_1 + t_2 + c$$

where t is the time of flight across a propagation path as labelled in FIGS. 24A-D, the delay of an acoustic transmitter is denoted in upper case, and the delay of an acoustic receiver is denoted in lower case. The system can optionally filter out noises using a band-pass or high-pass filter (described below) at step 810 before taking measurements from the acoustic receivers.

From these measurements, the hardware processor can calculate time of flight $t_2$ between the acoustic receivers b, c at step 830:

$$t_2 = \tau_2 - \tau_1 - (c-b)$$

This time of flight measurement $t_2$ is a unidirectional measure of the speed of sound that depends only on the matching of the acoustic receivers' delays. As described above, the hardware processor can optionally calculate gases concentration including but not limited to oxygen concentration from the unidirectional measure of the speed of sound at step 840. In the second direction the hardware processor can similarly obtain measurements at steps 850, 860:

$$\tau_3 = D + t_3' + c$$

$$\tau_4 = D + t_3' + t_2' + b$$

$$t_2' = \tau_4 - \tau_3 - (b-c)$$

where $\tau_3, \tau_4$ are measurements at the acoustic receivers c, b and $t'_2$ is the time of flight between the receivers b, c in the opposite direction.

From these two time of flight measurements, the hardware processor can obtain the sum and difference, which can be used to closely approximate the speed of sound and flow measurement, at step 870:

$$t_2 t_2' = (\tau_2 - \tau_2) + (\tau_4 - \tau_3)$$

$$t_2 - t_2' = (\tau_2 - \tau_1) - (\tau_4 - \tau_3) - 2(c-b)$$

Thus, the hardware processor can obtain a speed of sound measurement independent of the acoustic transmitter delays, and optionally a flow measurement dependent only on the matching of two delays at step 880. The speed of sound and flow rate measurements can be obtained from a time of flight measurement, starting with the following two expressions: $t_2$=(distance D between receivers b and c)/[(speed of sound, c)+(speed of gases flow, v)]; $t_2'$=(distance D between receivers b and c)/[(speed of sound, c)−(speed of gases flow, v)]. The speed of sound and speed of gases flow can then be solved using the equations below.

$$c = \frac{D}{2}\left(\frac{1}{t_2} + \frac{1}{t_2'}\right)$$

$$v = \frac{D}{2}\left(\frac{1}{t_2} - \frac{1}{t_2'}\right)$$

This cancellation can occur because in each direction along the acoustic path the hardware processor can make a differential measurement with the same two acoustic transmitters. The two acoustic transmitters can be a matched pair of acoustic transmitters, for example, a matched pair of piezoelectric transducers. As the transmitter delays are present in each received signal, the transmitter delays cancel when taking the differential measurements. As the same receiver delays appear in each direction but in opposite order, the receiver delays cancel for the speed of sound calculation. The only delays that need to be known are the matching of two receivers for the flow rate measurement, which the hardware processor can robustly correct for using a no-flow condition, where $t_2 - t_2' = 0$ and the term c−b can be directly computed from the system's measurements alone. This correction method can be computationally less complex than having to create a known gas condition in order to compute $t_2 + t_2'$, which depends on the speed of sound, temperature, humidity, gas composition, and the like. By applying a "null" or no-flow condition to the flow measurement at start-up, before operation, or any other convenient time, or using a known flow rate or an independent flow sensor, the flow rate measurement can depend only on drift in the matching of two acoustic receiver delays during operation.

In addition to the advantages due to the use of receivers and/or the configurations described above, the two transmitter/two receiver configurations have additional advantages, which will be described below.

The configurations described above can provide redundancy. Specifically, since each pair of acoustic transmitter/receiver A-D, A-c, A-b, D-A, D-c, and D-b in FIG. 24A can operate independently to sense time of flights, the hardware processor can use these measurements as checks on the principle operation of the sensors or as independent measurements. The redundancy can increase the robustness of the system. Similarly, the hardware processor can use the redundancy for better fault detection. The system can be checking constantly or at regular intervals to make sure there are no unexpected changes in signals. If a corrupted signal/no signal is detected, for example, if one of the acoustic transmitters/receivers (for example, transmitter A) ceases to function properly, the hardware processor can use measurements of the other pairs of acoustic sensors, (for example, acoustic transmitter/receiver b, c, and D) to sense which component is at fault. In contrast, in a system with only sensors A and D that both transmit and receive the signals, the system can know that either sensors A or D is at fault, but not exactly which sensor is at fault.

Further, the distance between A-b and D-c is much smaller than distances between the other pairings. Differences in the distances can also be used to mitigate the requirements around "windowing." Specifically, the distance between the acoustic transmitter and the acoustic receiver closer to the acoustic transmitter can be defined as a first or short distance. The distance between the acoustic transmitter and the acoustic receiver further from the acoustic transmitter can be defined as a second distance. The second distance can be longer than the first distance. The first receiver, which can be b or c depending on the direction of the signal, receives a signal from the acoustic transmitter and the hardware processor can obtain an estimate of speed of sound, such as by using a rough estimate of the waveform shape. The hardware processor can use the rough or coarse estimate of the speed of sound with measurement of the time of flight along the short distance to set the window for other measurements. The second acoustic receiver can then help with a more accurate speed of sound measurement. The hardware processor can use measurements taken along the long distance to obtain a more accurate assessment of the waveform characteristics. Further, time of flight measurements taken along the short distance can allow the system to operate under different operating conditions, such as with a wide range of gases, and can be particularly helpful for gases such as heliox or carbon dioxide, which have very different speeds of sound. Accordingly, the short distance allows the system to establish a window that is appropriate for a particular gas, and thus provides an expected time of flight for a particular gas, which allows for exclusion of signals occurring in the time periods that are not relevant, such as those due to noise or transients. The system can then control when and for how long the signals are transmitted and received, based on the determined window. Once an appropriate sampling of the relevant signals within the determined window is established, the system can determine gases concentration and/or flow rate for the particular gas using the methods described herein.

In addition, self-calibration can be achieved with the two acoustic receivers, as measurements of the acoustic receivers can be checked against each other. The hardware processor can be further configured to use signals received at the two acoustic receivers to determine waveform deformation. The hardware processor can be configured to use the cross-correlation to detect distortion or perturbations occurring between the two received acoustic signals. The distortion or perturbations can occur due to obstructions in the flow-path, reflections, non-linearity in the receivers, or a combination thereof. Indications of waveform deformation can be used to detect non-linear-phase delays, which alter the shape of the signal rather than just simply time-delaying the signal going between the acoustic receivers.

Mitigation of Effects of Noise

As described above, microphones can be sensitive to ambient acoustic noise. For example, the noise in the flow path can be up to about 15 kHz.

As any sources of acoustic noise are often experienced by both microphones, when differential measurement is used in the present disclosure, this noise can largely cancel out if it is from a common source. Moreover, because acoustic noise is generally not in the ultrasonic frequency band, the noise can be filtered out to an extent. The noise can be reduced in part by applying a digital or analogue band-pass or high-pass filter to the acoustic signal from the microphones for anything outside of a relatively narrow expected range. For example, single-stage low-pass Sallen-Key or multiple feedback filters can optionally be implemented with a single op-amp to reduce the effect of acoustic noise. A compact layout of the sensing circuit board can advantageously make the filtering mechanisms more effective by reducing unwanted feedback paths, which when combined with the existing high gain in the circuit can lead to oscillations in the signal. Specifically, by keeping the tracks on the sensing circuit board short, the tracks are less likely to radiate or receive unwanted feedback such as noise/EMC and affect other tracks.

Another robust way for mitigating acoustic noise is to change the edge detection method. Instead of using a comparator to detect zero-crossing, a fast ADC can be used to measure the acoustic signal. A cross-correlation between the two acoustic signals can then produce a noise-insensitive measurement of the delay between the acoustic receivers. The edge detection method can be combined with the band-pass filter and/or cross correlation method to further reduce effect caused by noise on the microphones.

Single Acoustic Transmitter/Single Acoustic Receiver Configuration

Figure 24B:
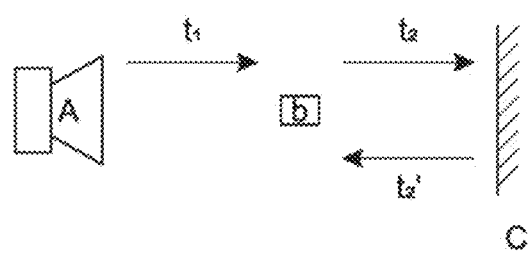
Figure 24C:
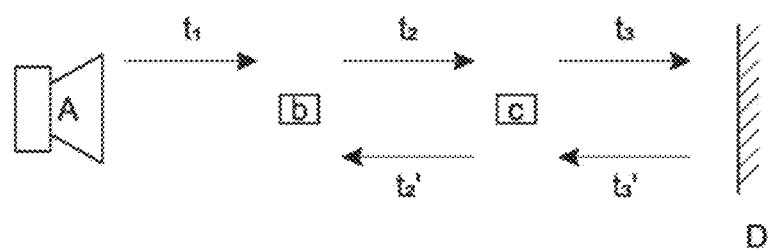
Figure 24D:
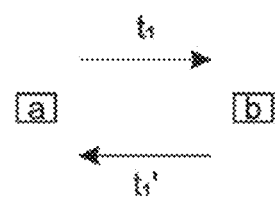

Example variations of the sensing circuit boards described above will now be described with reference to FIGS. 24B-D, which are simplified illustrations of the system described above. In FIGS. 24A-D, the gases flow travels in a direction such that at least a component of the flow is in line with the acoustic signal or overlaps with the acoustic path. Features described above for the two acoustic transmitters/two receivers configurations can be incorporated into the variations unless noted otherwise below. For example, the acoustic receiver(s) can be positioned within the gases flow path. The receiver(s) can be positioned within the measurement portion of the gases flow path. The variations can further include a temperature sensor, combined humidity and temperature sensor, and the like as described herein for determining the characteristics of the gases flow.

FIG. 24B illustrates a single acoustic transmitter/single receiver configuration. In this configuration, a reflection of the acoustic signal is used in the opposing direction instead of using a separate second acoustic transmitter. Specifically, as shown in FIG. 24B, an acoustic signal is generated by an acoustic transmitter A, propagated past an acoustic receiver b in a first direction, then reflected at a reflecting surface C and again propagated past the same acoustic receiver b in the opposite direction. Two measurements can be made, both at the acoustic receiver b, first on the initial signal and second on the reflected signal:

$$\tau_1 = A + t_1 + b$$

$$\tau_2 = A + t_1 + t_2 + t_2' + b$$

Taking the difference between these two measurements:

$$t_2 t_2' = \tau_2 - \tau_1$$

Thus, because the term $A + t_1 + b$ appears in both measurements, they cancel, leaving behind a measurement independent of the delays through the transmitter/receiver. The sum of $t_2$ and $t_2'$ represents a speed of sound measurement with no dependence on transmitter/receiver delays. In addition, a hardware processor can compute $t_1 = \tau_1 - (A+b)$ to obtain the speed of sound in one direction if the acoustic transmitter/receiver delays can be known. A disadvantage of this method is that the use of a reflection can introduce distortion to the waveform, which can appear as a spurious delay in the second measurement.

Single Acoustic Transmitter/Two Acoustic Receivers Configuration

Turning to FIG. 24C, a configuration comprising a single acoustic transmitter A, two acoustic receivers b, c, and a reflecting surface D can be used. As a reflection of the acoustic signal is used in the opposing direction instead of using a separate second acoustic transmitter, the same final expressions as derived for the two acoustic transmitters/two receivers configuration described above can be used. Although there may be constraints and errors due to the use of a reflected signal, such as distortion of the acoustic signal introduced during the reflection, the distortion will be sensed by both acoustic receivers b, c. Thus, any change in the signal is irrelevant since the reflection is merely acting as the second transmitter. Any introduced distortion will cancel out for both flow rate and speed of sound determinations. Further, as the reflecting surface D is acting as the second acoustic transmitter, the hardware processor can make redundant measurements as described above. For example, when one acoustic receiver is at fault, the second acoustic receiver can be used to determine where the fault occurred. The hardware processor can also perform cross-correlation for this echo arrangement as the same acoustic signal is received twice.

The reflected acoustic signals may not be required for determining certain characteristics of the gases flow, such as gases concentration, which only requires a unidirectional speed of sound measurement.

No Acoustic Transmitter/Two Acoustic Receivers Configuration

FIG. 24D illustrates a configuration without an acoustic transmitter. In this configuration, the acoustic receivers a, b can pick up any detectable sources of sound that are present in the system. The sources of sound can include a baffle or obstruction to the gases flow, which can create sounds when gases flow interacts with the baffle or obstruction. The sources of sound can include the blower. Using this configuration, the hardware processor can calculate both speed of sound, and therefore gases concentration, and flow rate. Each acoustic receiver can pick up the same, but delayed, sound waves. Again, by taking the difference in time of flight measurements between the two received acoustic signals, the acoustic receivers' delays can cancel out. Cross-correlation and other more advanced methods can be used for measuring these time delays.

Other Variations

Figure 26:
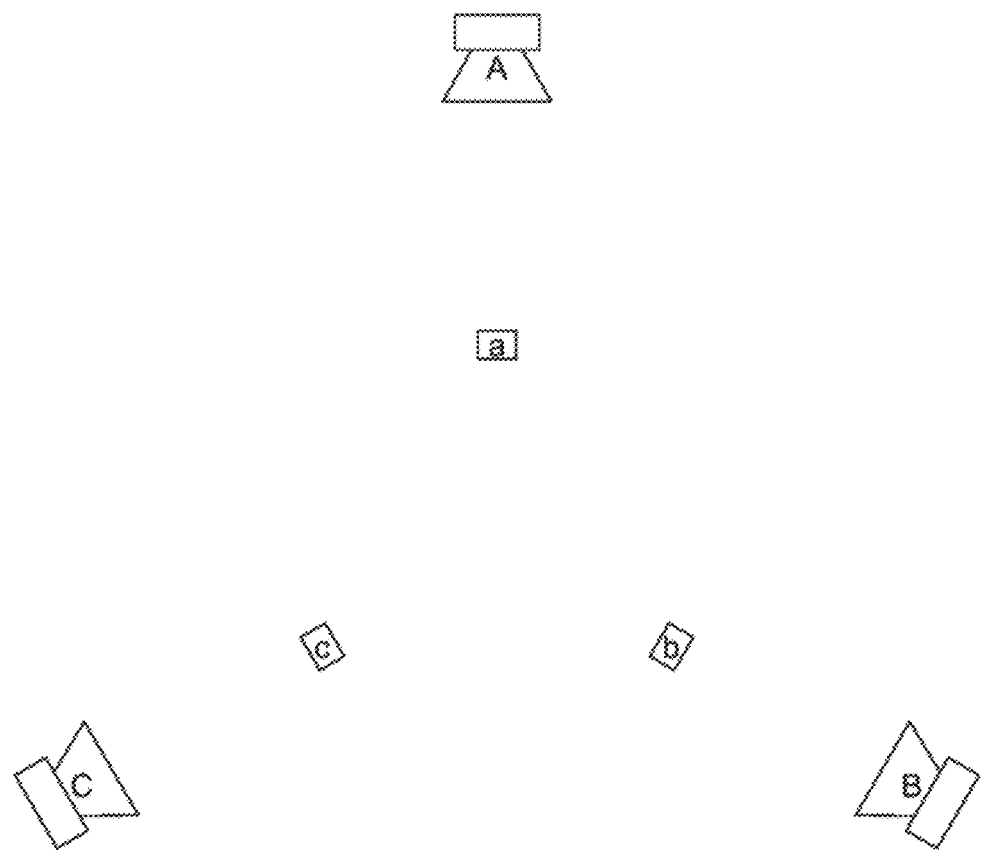
FIG. 26 illustrates other examples of ultrasonic sensing configuration with separate receivers.

The configurations described above can be extended to multi-dimensional flow measurements. As illustrated in FIG. 26, by configuring three acoustic transmitters, A, B, C, in a plane, with each acoustic transmitter transmitting in turn, the hardware processor can use the time of flights between any two pairs of acoustic transmitters to compute a flow vector in that plane, assuming the acoustic propagation path of the two pairs are not parallel to each other. Similarly, four acoustic transmitters located in three dimensions can allow for a complete flow vector to be obtained by the hardware processor.

Similarly, as illustrated in FIG. 26, for the cancelling configurations described herein, three acoustic receivers, a, b, c, can be configured in a plane and can provide measurements for the hardware processor to calculate the velocity and flow vector in that plane respectively. Four acoustic receivers can be configured in three dimensions to allow for a complete velocity and flow vector in three dimensions to be obtained by the hardware processor. Pairs of acoustic receivers can provide differential cancellation of delays as described above.

In addition, it would be possible to use more than two acoustic receivers to measure a flow vector or provide measurement redundancy.

Further, simultaneous measurements can be used. Specifically, as two acoustic transmitters can produce acoustic signals at the same time; there will be two peaks corresponding to each direction for a cross-correlation method. If the acoustic transmitters can resonate at different frequencies, the separation of the correlation peaks can be increased, thereby improving the robustness of the measurement. The system using different acoustic transmitters or the same acoustic transmitter at different frequencies can better distinguish the acoustic signals.

In addition to variations to the configuration of the acoustic sensor itself, the use of acoustic receivers, such as microphones, can allow for a number of other features to be implemented in the device. For example, the acoustic signals received by the acoustic receivers can contain at least in part motor noise. The acoustic signals can be analyzed to determine a fault condition in the motor. Motor faults which can be detected can include but are not limited to bearing faults, such as those caused by water ingress and/or general wear and tear, impeller impact on the blower housing, an imbalanced impeller, and the like.

The detected acoustic signals can first be filtered to remove any noise that does not relate to motor noise, including but not limited to noise generated by the flow of air through the airflow path, the patient's body, formation of bubbles in the humidification chamber, and/or from the patient interface such as leaks. The non-motor related noises may be filtered out via additional noise reduction techniques. Alternatively, such filtering may be undertaken as a consequence of analysis of the acoustic signal. During determination of a fault condition the ultrasonic sensors or any other sensors may be turned off to lower any background noise.

The acoustic signals can be spectrally analyzed to determine whether a frequency component indicative of a fault exists. Each fault may have a separate spectral peak corresponding with a specific fault condition. The detected acoustic signals may be analyzed to determine a specific fault condition. The analysis may be based on a frequency or range of frequencies present in the signal that is above a threshold. The magnitude of the threshold can be determined from a baseline signal amplitude, or the amplitude at some other frequency, or where the shape of the signal, normalised for amplitude, is compared against a template known to correspond to a particular fault type. Other ways of determining the threshold frequency can be used based on the disclosure herein.

The specific fault condition detection can also be based on an amplitude of the acoustic signal at a frequency or a range of frequencies. The amplitude or amplitude relationship information between different fault conditions may be stored in memory, such as the memory 624 shown in FIG. 19B, for each specific fault condition. For example, this technique may be used to distinguish between two or more fault conditions which vary in response to motor speed, and as such would show as a similar frequency in the acoustic signal. In this case as the fault conditions would appear at the same frequency or range of frequencies, the two or more fault conditions may be distinguishable by their respective amplitudes (for example peak or root mean square ("RMS") amplitude).

Some motor fault conditions may be related to or correlatable with the motor speed. For example, if the impeller is impacting on the blower housing at every revolution, the spectral analysis of the acoustic signal will show a peak at or near the frequency of the motor speed. The impeller impacting on the housing may also have a larger amplitude than an imbalanced impeller, although both fault conditions would generate a noise at or near the frequency of the motor speed.

The motor speed may be varied during a fault detection operation to provide indication of a fault condition. As described above, the motor speed may be related to the portion of the signal generated as a consequence of the fault. Therefore, as the motor speed is varied, a corresponding portion of the detected signal caused by or relating to the fault condition may also vary. Correspondence between the variation in motor speed and a peak in a portion of the signal received by the acoustic receiver may be indicative of a motor fault or a group of motor faults. [0148] Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A respiratory assistance system configured to provide a flow of gases generated by a blower to a patient to deliver high-flow therapy to the patient, the system comprising:
    a first acoustic transmitter positioned at a first position in or near a gases flow path, the first acoustic transmitter configured to transmit a first acoustic signal;
    a second acoustic transmitter positioned at a second position in or near the gases flow path, the second acoustic transmitter configured to transmit a second acoustic signal; and
    one or more acoustic receivers positioned in the gases flow path between the first position and the second position and being located between and spaced from the first and second acoustic transmitters at a first sufficient distance so as to mitigate near-field effects, said one or more acoustic receivers being located substantially coaxially with the first acoustic transmitter and the second acoustic transmitter, the one or more acoustic receivers configured to directly receive the first and the second acoustic signals, each of the one or more acoustic receivers comprising a microphone,
    wherein the first and second acoustic transmitters and the one or more acoustic receivers are in electrical communication with a hardware processor configured to determine one or more characteristics of the gases flow based on the first and second acoustic signals received by the one or more acoustic receivers.

2. The respiratory assistance system of claim 1, wherein the one or more acoustic receivers are two acoustic receivers.

3. The respiratory assistance system of claim 2, wherein one acoustic receiver is downstream of another acoustic receiver.

4. The respiratory assistance system of claim 3, wherein the two acoustic receivers are spaced apart by a second sufficient distance to improve flow sensitivity, and each of the two acoustic receivers is spaced from each of the first and second acoustic transmitters by at least the first sufficient distance so as to mitigate near-field effects.

5. The respiratory assistance system of claim 1, wherein the first and second acoustic transmitters face each other along the gases flow path so that acoustic signals produced by each acoustic transmitter are directed toward the other acoustic transmitter.

6. The respiratory assistance system of claim 1, wherein the first and second acoustic transmitters are a matched pair of acoustic transmitters.

7. The respiratory assistance system of claim 1, wherein the one or more characteristics of the gases flow comprise one or more of a gases concentration or a gases flow rate.

8. The respiratory assistance system of claim 7, wherein the gases concentration comprises an oxygen concentration, a carbon dioxide concentration, or a heliox concentration.

9. The respiratory assistance system of claim 7, wherein the hardware processor is further configured to:
    determine the gases concentration based on at least one of the first or second acoustic signals; and/or
    determine the gases flow rate based on both the first and second acoustic signals.

10. The respiratory assistance system of claim 1, wherein the hardware processor is configured to estimate a temperature of the one or more acoustic receivers using a measured temperature of gases in the flow path.

11. The respiratory assistance system of claim 1, comprising one or more of a temperature sensor, a pressure sensor, a humidity sensor, or a flow rate sensor, wherein the hardware processor is configured to be in communication with the one or more of the temperature sensor, the pressure sensor, the humidity sensor, or the flow rate sensor and to use outputs of the one or more of the temperature sensor, the pressure sensor, the humidity sensor, or the flow rate sensor to determine the one or more characteristics of the gases flow.

12. The respiratory assistance system of claim 11, wherein the flow rate sensor is a heated temperature sensing element.

13. The respiratory assistance system of claim 11, wherein the processor is configured to compute or adjust a calibration parameter of the first and second acoustic transmitters or the one or more acoustic receivers based on a flow rate measured by the flow rate sensor.

14. The respiratory assistance system of claim 11, wherein the hardware processor is configured to use outputs of the one or more of the temperature sensor, the pressure sensor, the humidity sensor, or the flow rate sensor to provide corrections to determination of the one or more characteristics of the gases flow.

15. The respiratory assistance system of claim 1, wherein the gases flow path between the first position and the second position comprises a curved flow path.

16. The respiratory assistance system of claim 15, wherein the gases flow path between the first position and the second position comprises a portion of the flow path having a straight flow path.

17. The respiratory assistance system of claim 1, wherein the first and second acoustic transmitters are ultrasonic transmitters.

18. The respiratory assistance system of claim 1, further comprising the blower.

19. The respiratory assistance system of claim 18, wherein the blower is configured to provide the high flow therapy to the patient.

20. The respiratory assistance system of claim 18, wherein the blower, the first and second acoustic transmitters, and the one or more acoustic receivers are comprised within a non-removable sensor module or blower/sensor module.

21. The respiratory assistance system of claim 1, wherein said one or more acoustic receivers are located substantially at a midline of a width of the gases flow path.

22. The respiratory assistance system of claim 1, wherein the hardware processor is further configured to:
    determine time of flight measurements of the acoustic signals between the first transmitter and the at least one receiver, and between the second transmitter and the at least one receiver; and
    determine the one or more characteristics of the gases flow based at least in part on the time of flight measurements.

23. The respiratory assistance system of claim 1, wherein the hardware processor is configured to perform cross-correlation of the first and/or the second acoustic signals received respectively by the microphones.

* * * * *